US008635027B2

(12) United States Patent
Smythe et al.

(10) Patent No.: US 8,635,027 B2
(45) Date of Patent: Jan. 21, 2014

(54) COMMON PROTEIN SURFACE SHAPES AND USES THEREFOR

(75) Inventors: Mark Leslie Smythe, Bardon (AU);
Tran Trung Tran, Daisy Hill (AU);
Darryn Bryant, St. Lucia (AU);
Stephen Long, Graceville (AU); Peter Adams, Chandler (AU)

(73) Assignee: The University of Queensland, Brisbane, Queensland (AU)

( * ) Notice: Subject to any disclaimer, the term of this patent is extended or adjusted under 35 U.S.C. 154(b) by 766 days.

(21) Appl. No.: 12/542,427

(22) Filed: Aug. 17, 2009

(65) Prior Publication Data

US 2009/0318311 A1 Dec. 24, 2009

Related U.S. Application Data

(63) Continuation of application No. 10/503,655, filed as application No. PCT/AU03/00137 on Feb. 10, 2003, now abandoned.

(30) Foreign Application Priority Data

Feb. 8, 2002 (AU) .................................. PS0397

(51) Int. Cl.
*G01N 33/50* (2006.01)
(52) U.S. Cl.
USPC ........................................................ 702/19
(58) Field of Classification Search
None
See application file for complete search history.

(56) References Cited

U.S. PATENT DOCUMENTS 6,631,332 B2 * 10/2003 Skolnick et al. ................ 702/19
7,092,825 B1    8/2006 Smythe et al.

FOREIGN PATENT DOCUMENTS

| WO | WO 00/23474 |   | 4/2000 |
|----|-------------|---|--------|
| WO | WO/00/23474 | * | 4/2000 |
| WO | WO 01/37147 |   | 5/2001 |
| WO | WO 01/98457 |   | 12/2001 |

OTHER PUBLICATIONS

Ferre et al., "Protein surface similarities: a survey of methods to describe and compare protein surfaces," Cellular and Molecular Life Sciences, 2000, 57, pp. 1970-1977.*
Gabb et al., "Modelling Protein Docking using Shape Complementarity, Electrostatics and Biochemical Information," *J. Mol. Biol.*, 1997, pp. 106-120, vol. 272.
Peters et al., "The Automatic Search for Ligand Binding Sites in Proteins of Known Three-dimensional Structure Using only Geometric Criteria," *J. Mol. Biol.*, 1996, pp. 201-213, vol. 256.
Ritchie, D. et al., "Parametric Protein Shape Recognition," *Ph.D Thesis*, Sep. 1998, http://www.csd.abdn.ac.uk/~dritchie/.
Schneider et al., "Virtual screening and fast automated docking methods," *DDT*, Jan. 2002, vol. 7, No. 1.
Seidl et al., "Solvent Accessible Surface Representation in Database System for Protein Docking," *Proc. of 3rd Int. Conf. on Intelligent Systems for Molecular Biology* (*ISMB '95*), 1995.
International Search Report issued on Mar. 6, 2003, in application No. PCT/AU03/00137.
Office Action issued on Mar. 17, 2009, by the Examiner in U.S. Appl. No. 10/503,655 (US 2005-0154533).
Office Action issued on Apr. 10, 2008, by the Examiner in U.S. Appl. No. 10/503,655 (US 2005-0154533).
Office Action issued on May 8, 2007, by the Examiner in U.S. Appl. No. 10/503,655 (US 2005-0154533).
Office Action issued on Sep. 7, 2006, by the Examiner in U.S. Appl. No. 10/503,655 (US 2005-0154533).

* cited by examiner

*Primary Examiner* — Jason Sims
(74) *Attorney, Agent, or Firm* — Foley & Lardner LLP

(57) ABSTRACT

A method of determining common three-dimensional structural features of protein surfaces is provided, as is use of representations of these common structures in molecular database searching and in designing focused molecular libraries. The method is particularly concerned with the analysis and representation of protein surfaces such as b-turns, loops and contact surfaces. In one form, the method identifies common locations and orientations of amino acid side-chains, simplified as Cα-Cβ vectors. In another form, the method identifies common regions of surface charge represented by grid points in three-dimensional space. Further provided are common three dimensional structural features of proteins that can be used to search molecular databases for the purposes of identifying molecules that match these common three dimensional structural features. The common three dimensional structural features can also be used to focus de novo molecular generation to produce libraries containing molecules that have these common three dimensional structural features. Libraries of these structurally-related molecules may then be produced for the purposes of drug discovery.

23 Claims, 41 Drawing Sheets

(a)          (b)          (c)

Figure 1:
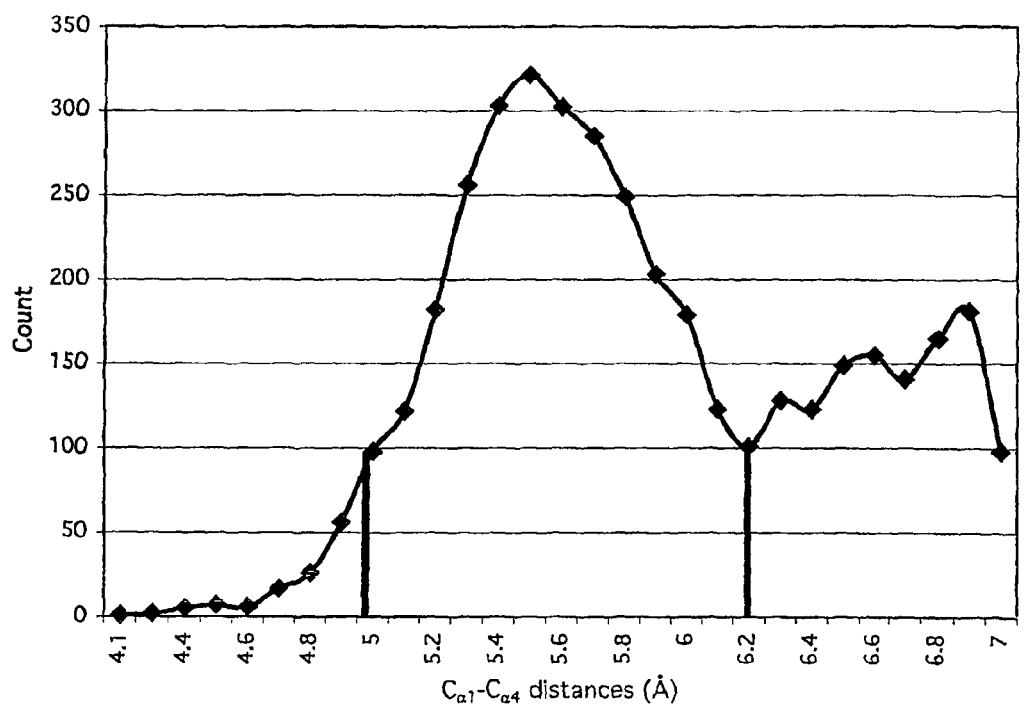

Figure 18.

> $T$ = number of chains in data set.
> For $i = 1...T$
>   While (a motif can still be constructed)
>     Construct motif
>     Calculate and store all $N(N-1)/2$ bowtie distances for that motif
>     Discard any motif with a bowtie distance greater than 25Å
>     Find the shortest bowtie base (tail to tail) length for each motif
>   Sort each motif in the chain in ascending order with respect to the short base length.
> For $i = 1 ... T$  // chain $i$
>   $F$ = number of motifs in chain i
>   For $j = 1 ... F$  // motif $j$
>     $S$ = shortest base distance in motif $j$ in chain $i$
>     $p = 1$  // points to the position in chain $i$ where the search should begin
>     For $k = i ... T$  // chain $k$
>       $G$ = number of motifs in chain $k$
>       $l = p$  // motif $l$
>       $R$ = shortest base distance of motif $l$ in chain $k$
>       If ($R$ >= $S$-TOL)
>         $p = l$  // change where search should start for next motif $l$
>         While ($R$ <= $S$+TOL)
>           If (there exits a rotation of motif $l$ such that every bowtie length of motif $j$ is equal within tolerance)
>             Record match against motif $l$ (if $i \ne k$) and motif $j$
>           $l = l+1$  // collect next motif in chain $k$
>           If ($l > G$) // if the end of chain $k$ has been reached
>             break while loop
>       Else $l = l+1$
> Send counters of motifs that record more than an appropriate matching frequency to an output file.

Figure 19.

```
Define family tolerance TOL
N = number of motifs in dataset
For i = 1...N  // motif i
  Tag motif i as a possible peak
For i = 1...N // motif i
  For j = 1...N  // motif j
    If (motif i matches motif j within TOL)
      If (the matching frequency of motif i is greater than the matching frequency of
         motif j)
        Remove tag from motif j
      Else remove tag from motif i
```

Figure 20.

```
Select a distance tolerance OTOL.
Select the k most frequent peak motifs to be seed points for each cluster.
N = number of motifs in dataset.
For i = 1 ... k   // motif i (seed points)
  For j = 1 ... N  // motif j
    If (motif i matches motif j within OTOL)
      Assign motif j to cluster i
```

Figure 22.

```
Select a distance tolerance GTOL.
Select the k most frequent peak motifs to be the seed points for each
cluster.
N = number of motifs in dataset.
For i = 1 ... k  // motif i (seed point)
  For j = 1 ... N  // motif j
    If (motif j is already in cluster i)
       continue.
    If (motif j matches any motif in cluster i within GTOL)
       Assign motif j to cluster i
       j = 1
```

Figure 24.

```
Select OTOL and GTOL.
Select the k most frequent peak motifs to be the seed points for each
cluster.
N = number of motifs in dataset.
For i = 1 ... k // motif i (seed point)
   For j = 1 ... N // motif j
      If (motif j is already in cluster i)
         continue.
      If (motif j matches any motif in cluster i within GTOL) and
         (motif j matches motif i within OTOL)
         Assign motif j to cluster i
         j = 1.
```

Figure 25.

> Select a greedy tolerance GTOL and a sealevel SL.
> Select the $k$ most frequent peak motifs to be the seed points for each cluster.
> $N$ = number of motifs in dataset.
> For $i = 1 \ldots k$ // motif $i$ (seed point)
>   For $j = 1 \ldots N$ // motif $j$
>     If (motif $j$ is already in cluster $i$)
>       continue.
>     If (motif $j$ matches any motif in cluster $i$ within GTOL) and
>       (the matching frequency of motif $j$ is greater than SL)
>       Assign motif $j$ to cluster $i$
>       $j = 1$.

Figure 28.

> Select a global tolerance RMSD value.
> Select the $k$ most frequent peak motifs to be the seed points for each cluster.
> $N$ = number of motifs in dataset.
> For $i = 1 \ldots k$  // motif $i$ (seed point)
>   For $j = 1 \ldots N$  // motif $j$
>     If (motif $i$ matches motif $j$ within RMSD)
>       Assign motif $j$ to cluster $i$.

Figure 35.

```
Create patch motifs of size M
Create a $K_M$ (complete) graph using 3D coordinate points as vertices. The edges of this
graph have weight equal to the distance between the vertices For each molecule i in the dataset
  For each patch j in the molecule i
    For each molecule k in the dataset (not i)
      For each patch l in the molecule k
        If (patch j match patch l within tolerance)
            and (the charges of the vertices matches within tolerance)
          Record a match against patch l and patch j.
```

Figure 36.

```
N = Initial size of patch = 3
DTOL = maximum distance between two points in a patch
For for each molecule i in the dataset
    For for each combination of size N of molecule i
        If (distance between all the points in the patch < DTOL )
            Add the patch to the patch list
```

Figure 37.

> For each molecule *i in the dataset*
>
>   For each (N-1) combination of (N-1)-patch
>
>     If (distance between all the points in all the (N-1) (N-1)-patch < DTOL )
>         Add the patch to the N-patch list

COMMON PROTEIN SURFACE SHAPES AND USES THEREFOR

FIELD OF THE INVENTION

THIS INVENTION relates to a method of determining common three-dimensional structural features of proteins and use of representations of these common structures in molecular database searching, in molecular engineering and in designing focussed molecular libraries. More particularly, this invention relates to the identification and representation of protein surfaces such as β-turns, loops and contact surfaces and the determination of grid points describing surface charge, or the determination of common locations and orientations of amino acid side-chains, simplified as Cα-Cβ vectors. These protein surfaces are typically involved in interactions with other molecules such as other proteins, nucleic acids, metal ions, antigens, drugs and toxins although without limitation thereto. This invention therefore provides common three-dimensional structural features that can be used to search molecular databases for the purposes of identifying molecules that match these common three dimensional structural features. The common three dimensional structural features can also be used to engineer de novo molecules or molecular libraries that have one or more common three dimensional structural features. Molecules and molecular libraries may be useful for the purposes of drug discovery.

BACKGROUND OF THE INVENTION

The chemical diversity possible amongst the suspected $10^{180}$ possible drug-like molecules is immense, and a given combinatorial library can only hope to capture a tiny fraction of this diversity space. Molecular library design strategies use chemoinformatic techniques to select a diverse set of molecules for library synthesis. The molecular selection process involves the calculation of the chemical characteristics of each member of the library, using hundreds of chemical descriptors. It is therefore possible to derive a "diverse" library, where the molecules differ from each other as much as possible in descriptor space, or a "focussed" library, where the molecules are similar in descriptor space to a known active. With hundreds of potential descriptors it is difficult to know which descriptors are important or essential for describing biological activity. These approaches consequently optimise libraries in the chemical universe but do not identify molecules that could modulate biological function.

It is becoming evident that the synthesis of large combinatorial libraries makes sense only if guided by sound library design principles. It is generally accepted that focussing libraries can lead to a 10-100 fold increase in the discovery of "hits" (i.e candidate or lead molecules).

A significant number of pharmaceutical targets involve the mimicking or inhibition of protein interactions with other molecules. With the rapid advance of the human genome project, it is likely that many more protein interaction targets will be identified.

Proteins are amino acid polymers that fold into a globular structure. This globular structure, in general, has a hydrophobic interior. The structure of proteins is defined by the polymeric nature of the backbone and includes secondary structure elements such as helices, sheets, loops and turns. Whilst the description of protein structure by the nature of its polymeric backbone (its "skeleton") is useful for comparing one protein to another, it is not useful when describing the structural elements of various molecular recognition events of proteins. This is because molecular recognition is a surface phenomenon and proteins use large flat surface areas ranging from 1150 to 4660 Å$^2$, comprising on average 211 atoms from 52 amino acid residues. These binding surfaces may be continuous (such as β-turns and loops), or discontinuous surfaces that comprise 1-11 segments (where a segment is separated by at least 5 amino acid residues and can be from a different secondary structure) with an average of 5 segments per interface.

OBJECT OF THE INVENTION

The present inventors have realized that by creating focussed libraries of compounds that mimic common structural elements of protein surfaces, the likelihood of that library containing a molecule that mimics or inhibits a protein-molecule interaction will be enhanced.

It is therefore an object of the invention to identify common elements of protein surfaces.

It is also an object of the invention to provide a method to identify or to de novo engineer one or more molecules that match common elements of protein surfaces.

SUMMARY OF THE INVENTION

The present invention is therefore broadly directed to the identification of common, protein surface elements as descriptors of protein surfaces for use in molecular design, engineering and screening.

In a first aspect, the invention provides a method of producing a description of a common three-dimensional protein surface shape including the steps of:

(i) identifying a three-dimensional surface shape of each of a plurality of proteins; and (ii) creating one or more descriptors wherein each said descriptor represents a common surface shape of two or more proteins of said plurality of proteins.

In one embodiment, the three three-dimensional surface shape is identified as respective amino acid side-chain locations and orientations of two or more amino acids of each said protein.

According to this embodiment, at step (ii) each said descriptor represents a common location and orientation of the respective amino acid side chains.

Preferably, each amino acid side chain used to produce said descriptor is simplified as a $C_\alpha$-$C_\beta$ vector.

In another embodiment, the three three-dimensional surface shape is identified as a surface charge distribution of each said protein.

According to this embodiment, at step (ii) each said descriptor represents a common charged surface region of two or more proteins of said plurality of proteins.

Preferably, each charged surface region is represented by at least four grid points.

According to the invention, said two or more amino acids form at least part of a structural feature of each of said two or more proteins.

Preferably, said structural feature is, or comprises, a β-turn, a loop or a contact surface.

In a second aspect, the invention provides a method of identifying one or more molecules having a common three-dimensional protein surface shape, said method including the steps of:

(i) creating a query using one or more descriptors that each represent a common three-dimensional protein surface shape; and (ii) using said query to search a database and thereby identify one or more entries in said database that correspond to one or more molecules that each match said descriptor.

In one embodiment, at step (i), the descriptor represents a common amino acid side-chain location and orientation of two or more amino acids of each of two or more proteins.

In another embodiment, at step (i), the descriptor represents a common protein surface charge shape of two or more proteins.

In yet another embodiment, the query comprises:

(a) a descriptor that represents a common amino acid side-chain location and orientation of two or more amino acids of each of two or more proteins; and (b) a descriptor that represents a common protein surface charge shape of said two or more proteins.

Suitably, according to the second aspect, said query is used to search a computer-searchable database comprising a plurality of entries.

Preferably, each amino acid side chain used to produce said descriptor is simplified as a Cα-Cβ vector.

Preferably, for the purposes of database searching, Cα-Cβ vectors and/or surface charge grid points are represented as a distance matrix.

In a third aspect, the invention provides a method of creating a library of molecules including the steps of:

(i) searching a database to identify one or more entries corresponding to one or more molecules that each match a common protein surface shape; and.

(ii) using at least one of the one or more molecules identified at step (i) to create a library of molecules.

In a particular embodiment, this third-mentioned aspect includes the step of creating a library of molecules from the one or more molecules identified as step (ii).

Said library of molecules may be a "virtual" library or a synthetic chemical library.

In a fourth aspect, the invention provides a method of engineering one or more molecules including the steps of:

(i) creating one or more descriptors that each represent a common three-dimensional protein surface shape; and (ii) engineering one or more molecules that respectively comprise one or more structural features according to the or each descriptor in (i).

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE FIGURES AND TABLES

FIG. 1. Distribution of $c_{\alpha 1}$-$c_{\alpha 4}$ distances of all four residues segments that are not helical nor β-sheets and that are found in high resolution and non-homologous structure in Protein Data Bank[31].

Figure 2:
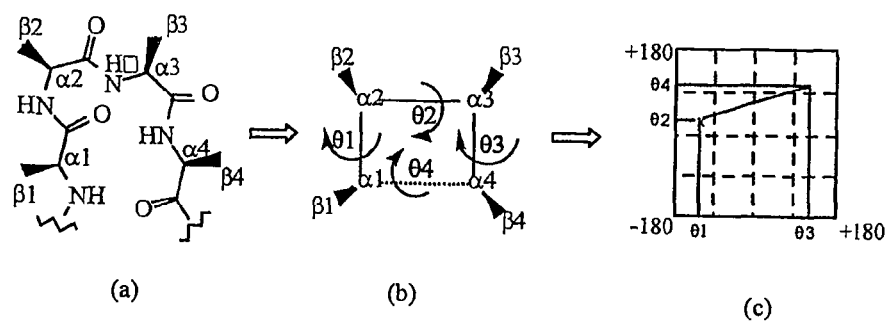

FIG. 2. a) Each β-turn is represented by four $C_\alpha$-$C_\beta$ vectors highlighted by the dark triangle. b) To aid visualization of the spatial arrangement of the turn after clustering, the four torsional angles θ1, θ2, θ3 and θ4 are used as approximation to the 24 distances. c) The four torsional angles are plotted as a vector from (θ1, θ2) (represented by the symbol 'x') to (θ3, θ4).

Figure 3:
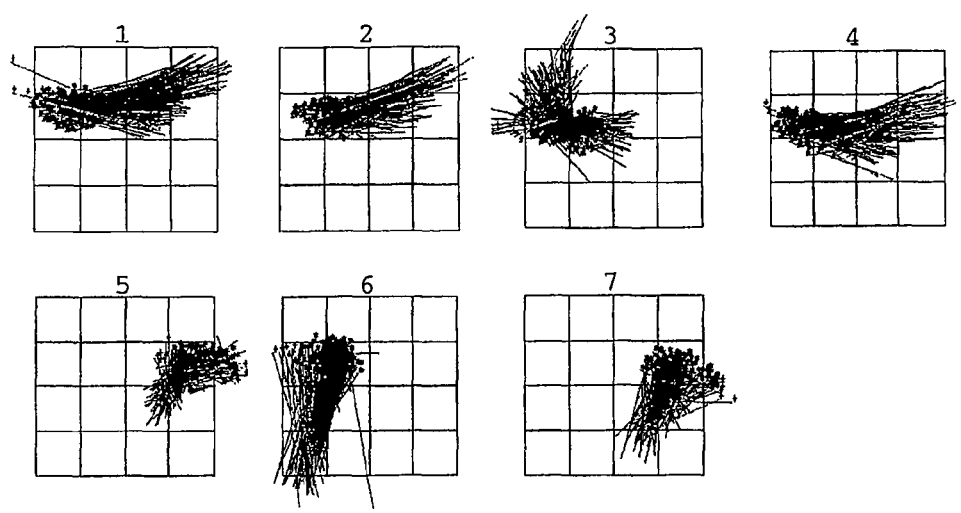

FIG. 3. Vector plot of the seven clusters obtained from the $k^{th}$ nearest neighbor cluster and the filtered nearest centroid sorting algorithms. A threshold of 0.65 RMSD was used.

Figure 4:
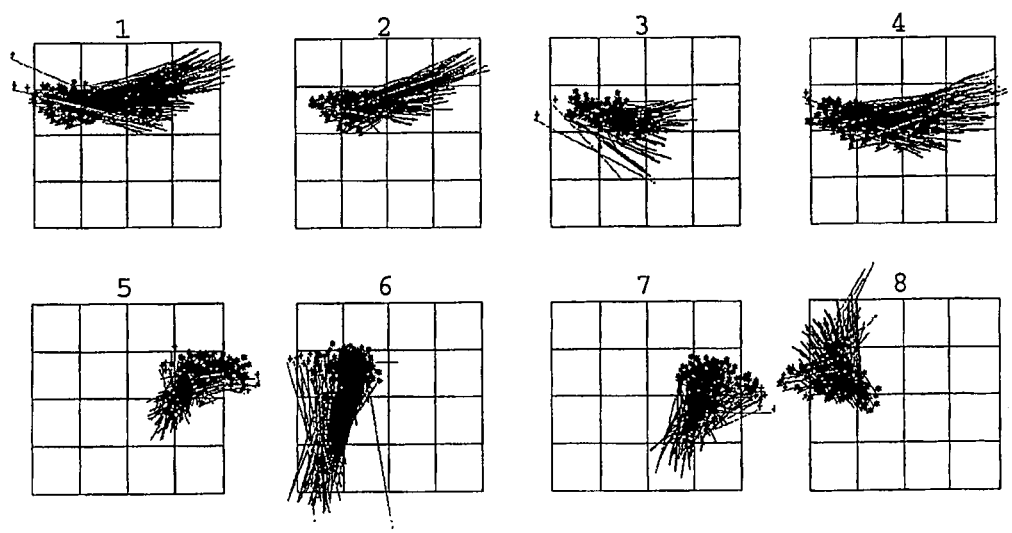

FIG. 4. Vector plots of the eight clusters formed from the clustering algorithm and explicit division of cluster three into two clusters.

Figure 5:
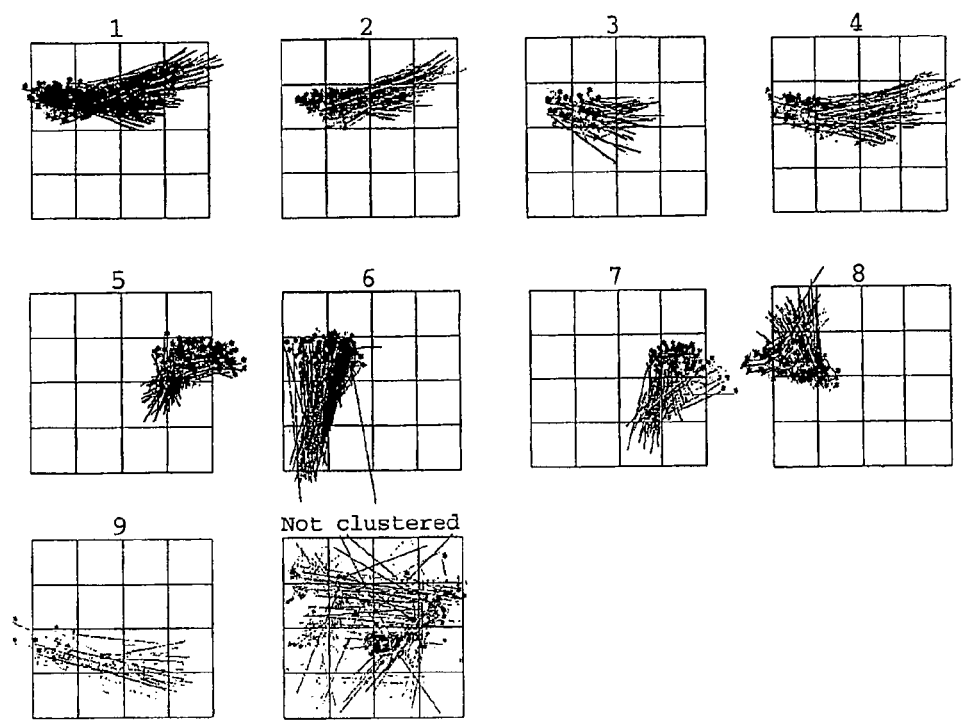

FIG. 5. Vector plots of the nine clusters formed from the clustering algorithm and explicit division of cluster three into two clusters and inclusion of the average structure of type I' in the initial seed. The last graph represents the conformations that were rejected and the first nine graphs represents the nine clusters.

Figure 6:

FIG. 6. The β-turns within each of the nine clusters were superimposed onto the cluster's mean structure.

Figure 7:
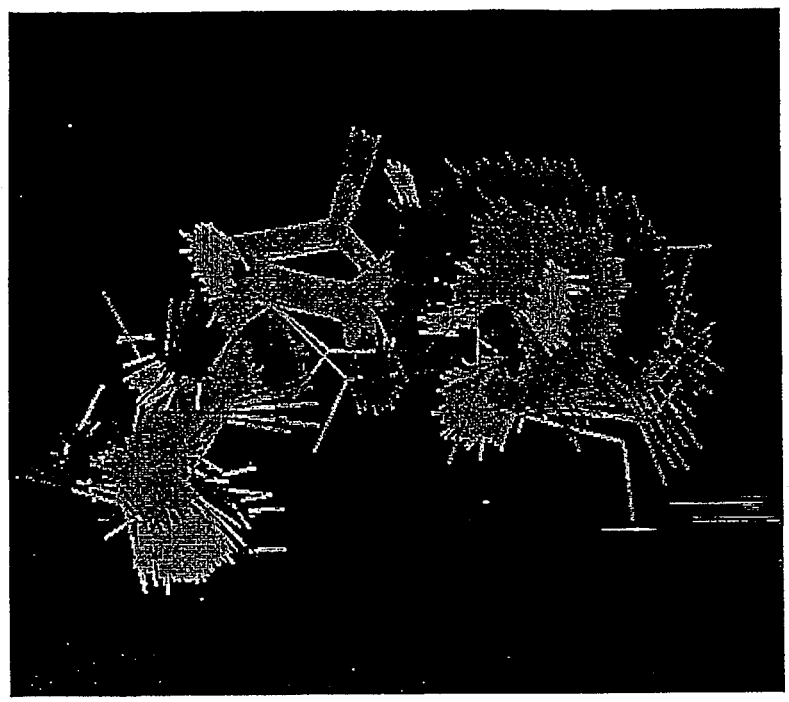

FIG. 7. Top view of the β-turns structures in cluster two superimposed onto its mean structure. The figure shows that the backbone structures can vary significantly even-though the $c_\alpha$-$c_\beta$ vectors are distributed uniformly.

Figure 8:
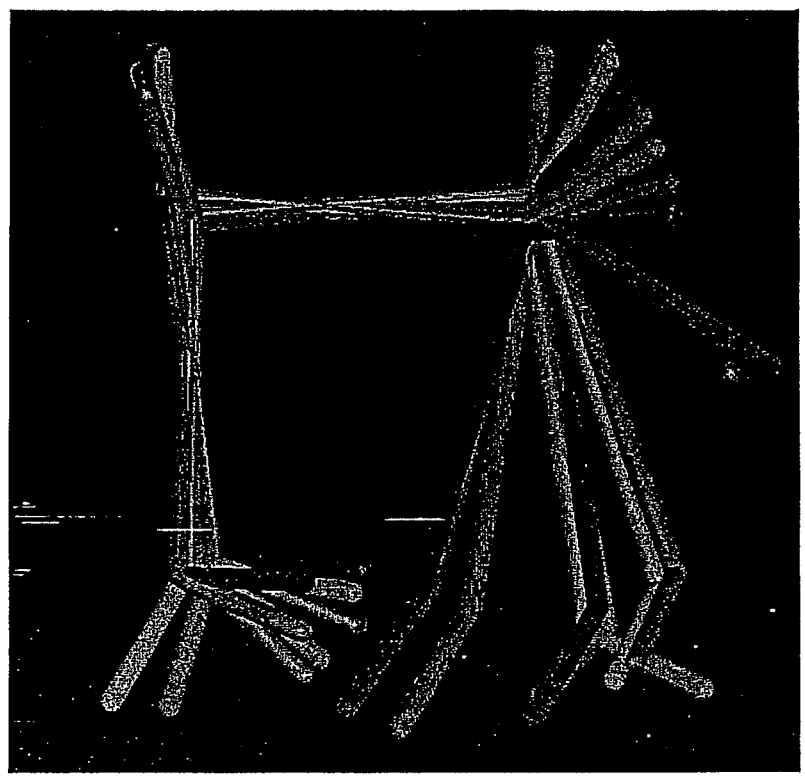

FIG. 8. Superimposition of the mean structures of the nine clusters. The superimposition is based on the three atoms $c_{\alpha 1}$ $c_{\alpha 2}$ and $c_{\alpha 3}$.

Figure 9:
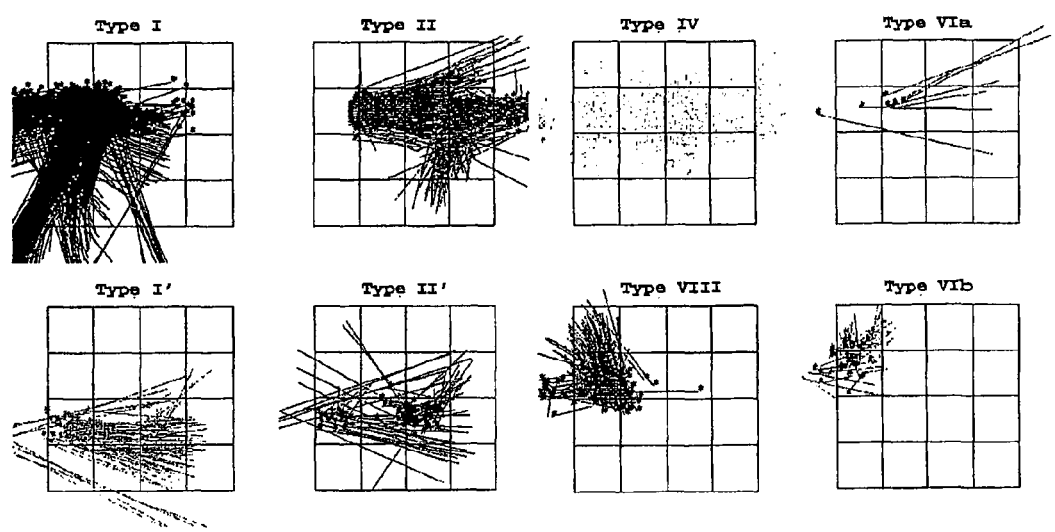

FIG. 9. Vector plots of the β-turns in each of the nine types of β-turns defined by Hutchinson and Thornton[25]. The order of the plots are: type I, II, I', N, II', VIa1, VIa2, VIII and VIb.

Figure 10:
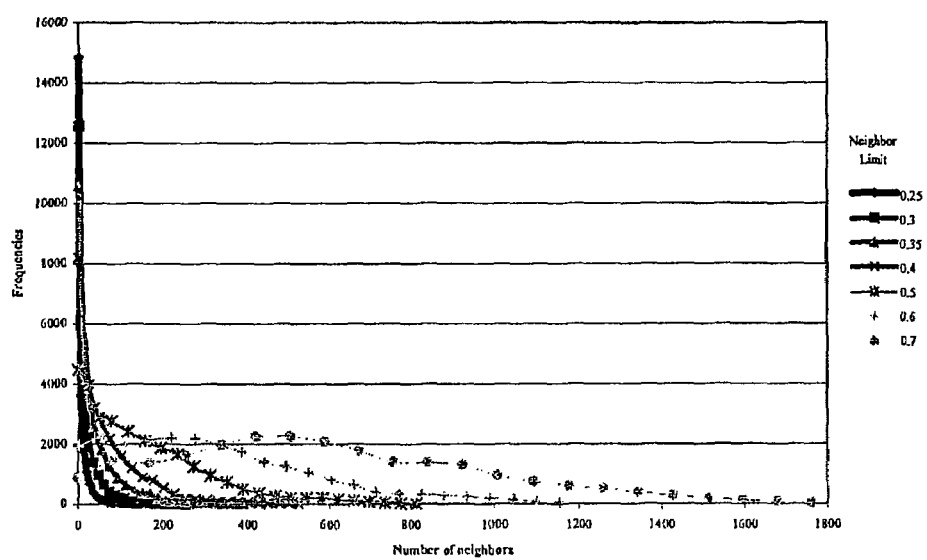

FIG. 10. Number of neighboring loops versus its frequencies for various values of NEIGHBOR_LIMIT.

Figure 11:
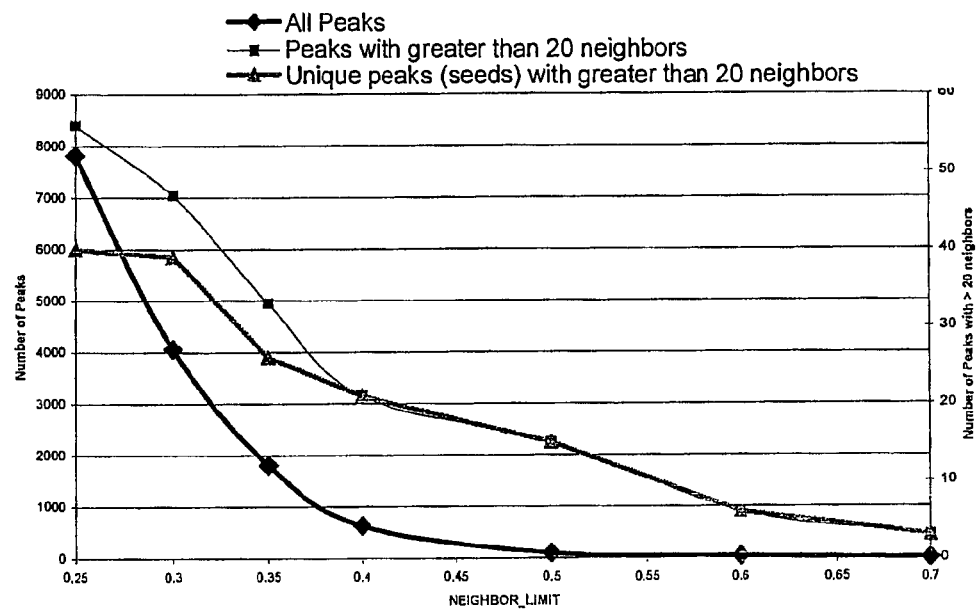

FIG. 11. Plot of (1) number of peaks, (2) number of peaks with greater than twenty neighbors and (3) number of unique peaks with greater than twenty neighbors as a function of NEIGHBOR_LIMIT.

Figure 12:
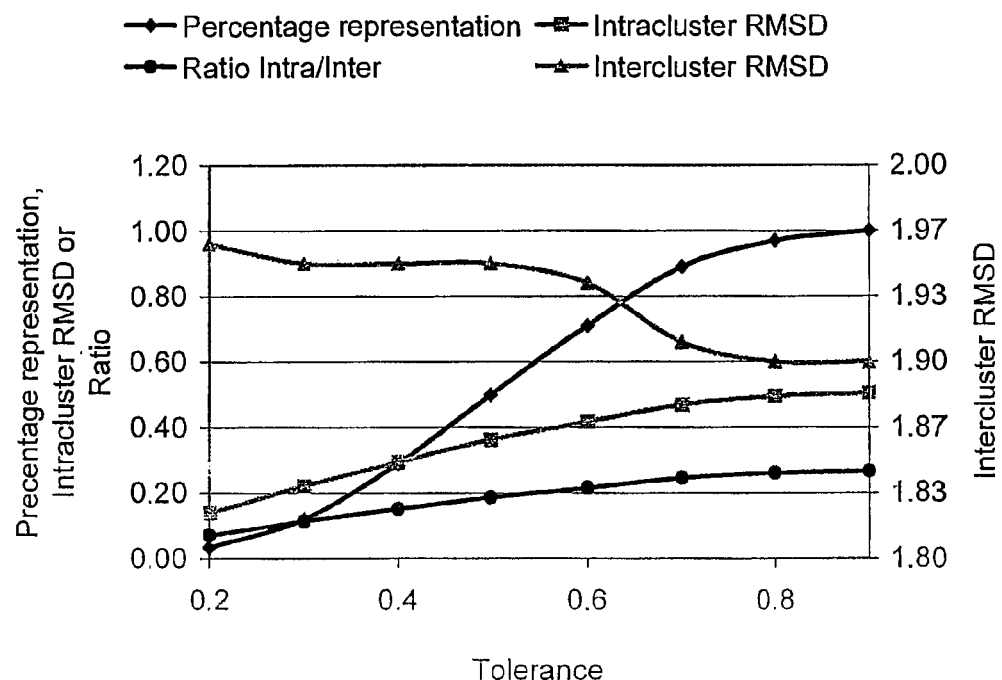

FIG. 12. Filtered centroid sorting algorithm was used with various TOLERANCE to obtain the 39 clusters. The percentage representation, the intracluster RMSD, the intercluster RMSD and the ratio of the latter two are calculated and plotted as a function of TOLERANCE.

Figure 13:
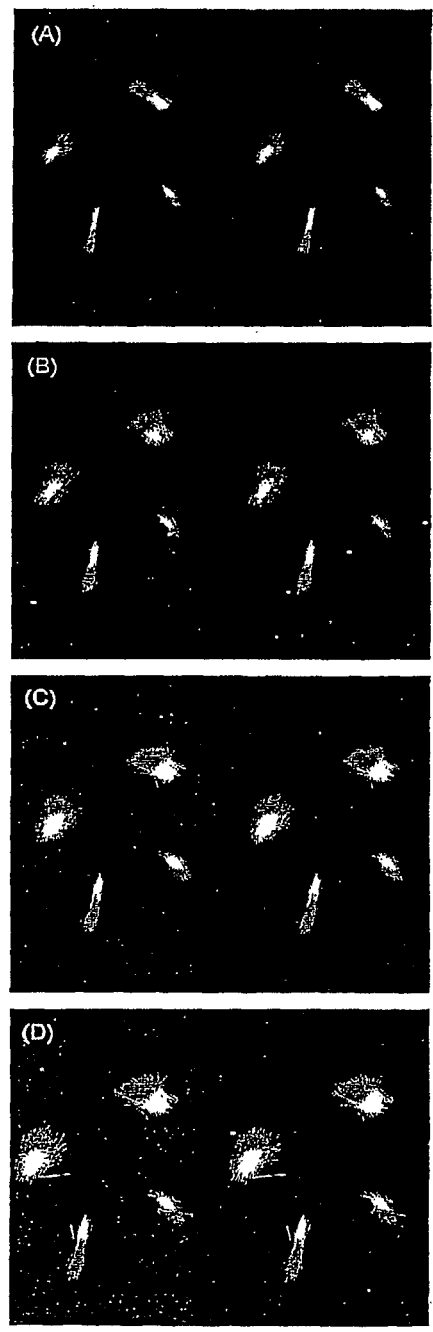

FIG. 13. The loops are assigned to one of the 39 seeds using various TOLERANCEs in the filtered centroid sorting algorithm. The resulting loops in cluster one are superimposed and displayed in stereo view to show the effect of the choice of the tolerance value. Each line connects the position of the $c_\alpha$ atom in white and the position of the $c_\beta$ atom in gray. TOLERANCE=A) 0.3, B) 0.5, C) 0.7 AND D) 0.9.

Figure 14:
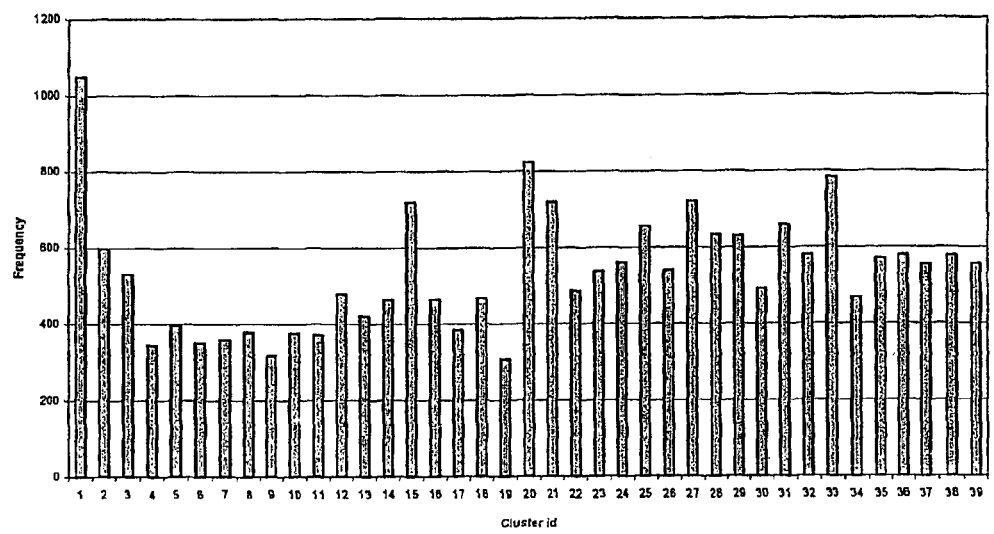

FIG. 14. Histogram of the number of loop in each of the 39 clusters.

Figure 15:
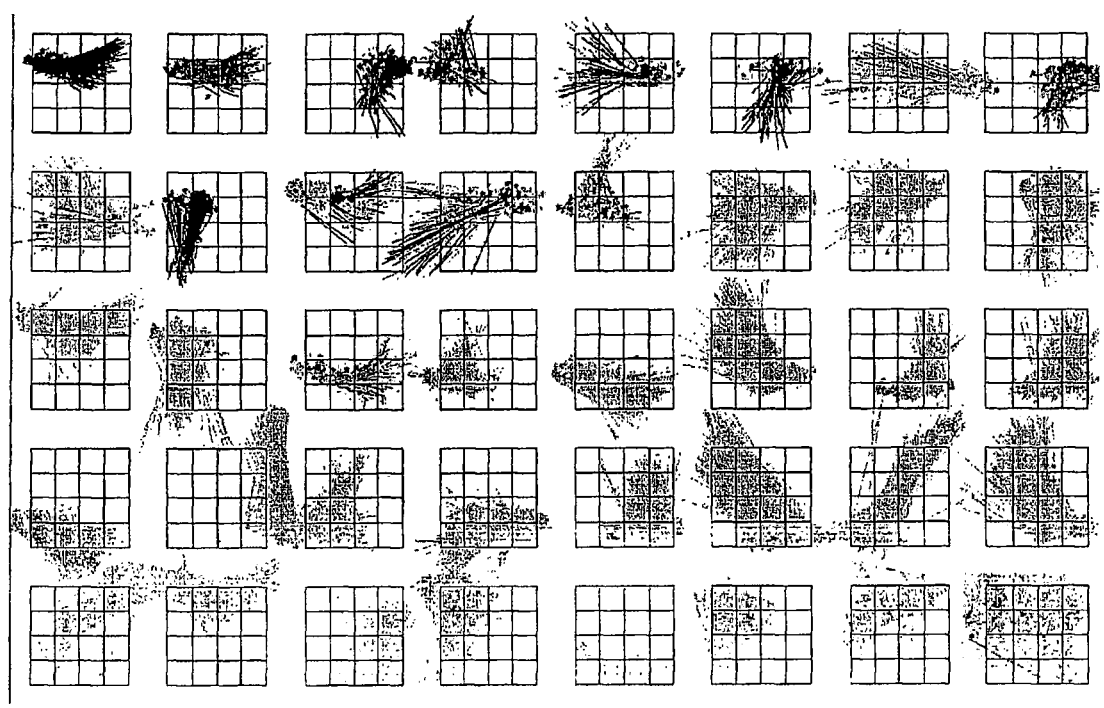

FIG. 15. Vector plots of the 39 clusters, with cluster number starting from one and counting across a row before going to the next row. The last cluster, cluster 40, represents all the loops that have not been clustered according to our filtered centroid sorting algorithm.

Figure 16:
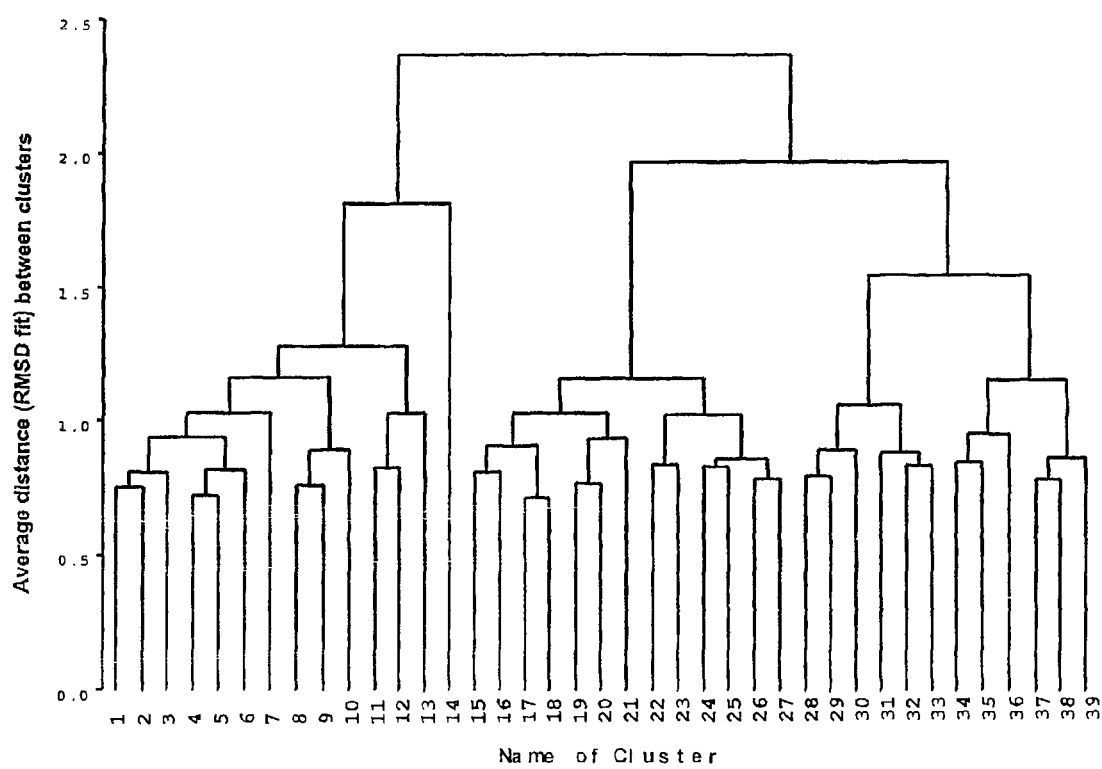

FIG. 16. Tree diagram of obtained from average linkage clustering of the 39 clusters.

Figure 17:
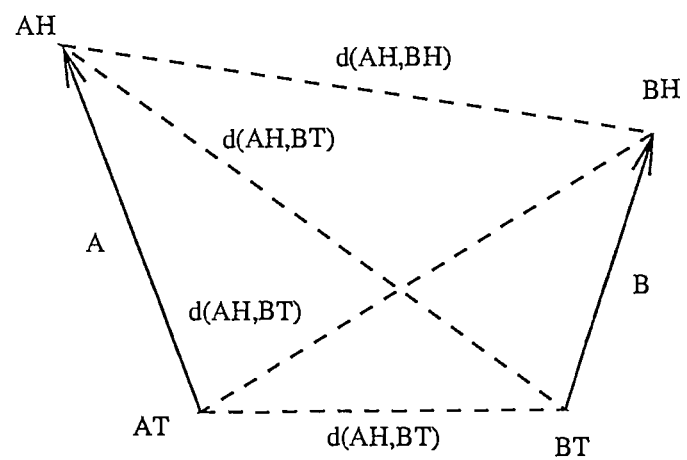

FIG. 17. An example of a bowtie. The function d(x,y) represents the euclidian distance between point x and point y. (H=Head, T=Tail).

FIG. 18. Algorithm for finding matching frequency of motifs.

FIG. 19. Algorithm for finding peak motifs.

FIG. 20. One-pass algorithm for clustering motifs.

Figure 21:
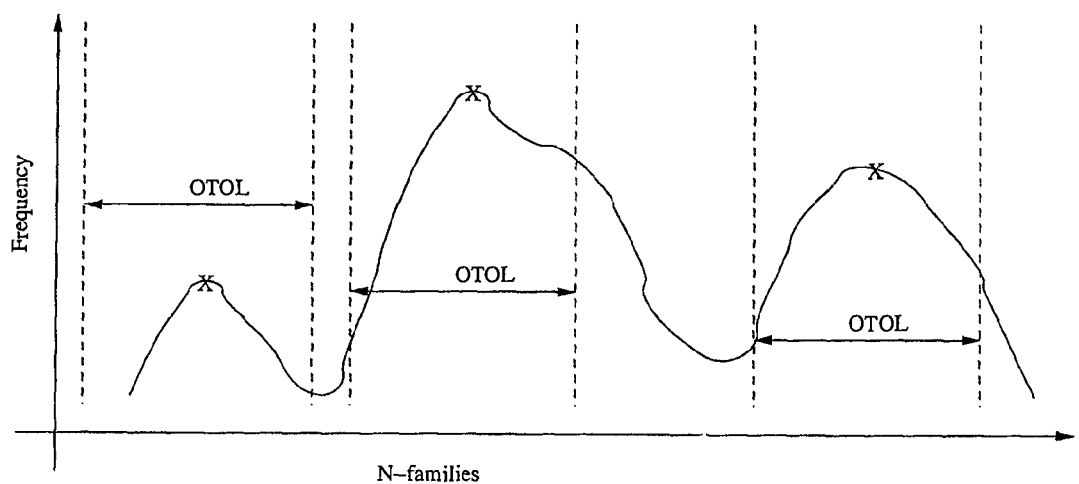

FIG. 21. The span of the one-pass algorithm.

FIG. 22. The greedy algorithm for clustering motifs.

Figure 23:
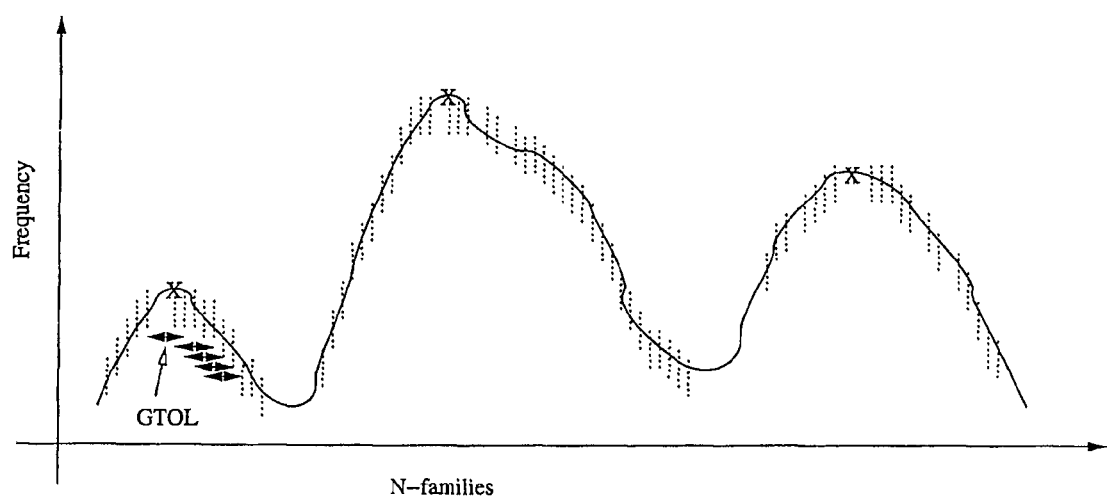

FIG. 23. The span of the greedy algorithm for clustering motifs.

FIG. 24. The combined one-pass and greedy algorithm for clustering motifs.

FIG. 25. The greedy algorithm with sealevel for clustering motifs.

Figure 26:
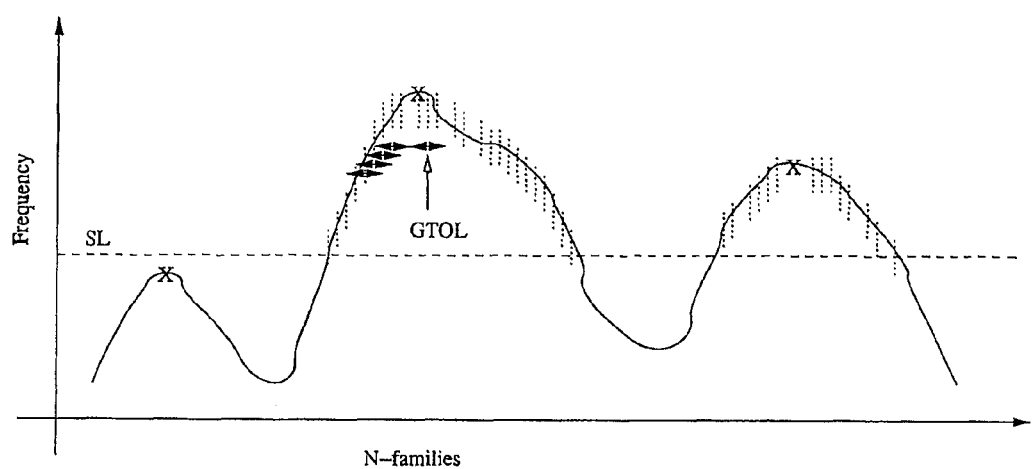

FIG. 26. The span of the greedy algorithm with sealevel.

Figure 27:
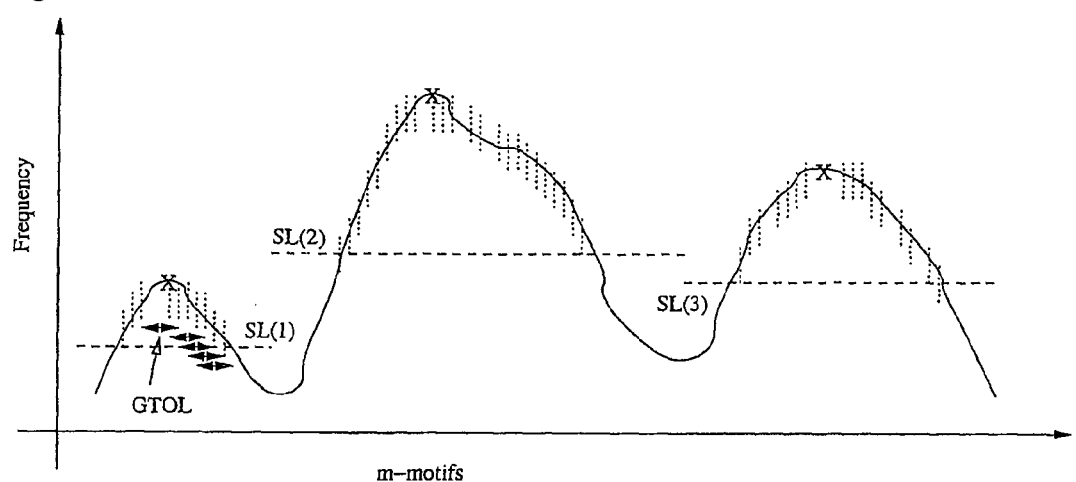

FIG. 27. Adaptive sealevel applied in combination with the greedy algorithm.

FIG. 28. The one-pass algorithm with RMSD tolerance.

Figure 29:
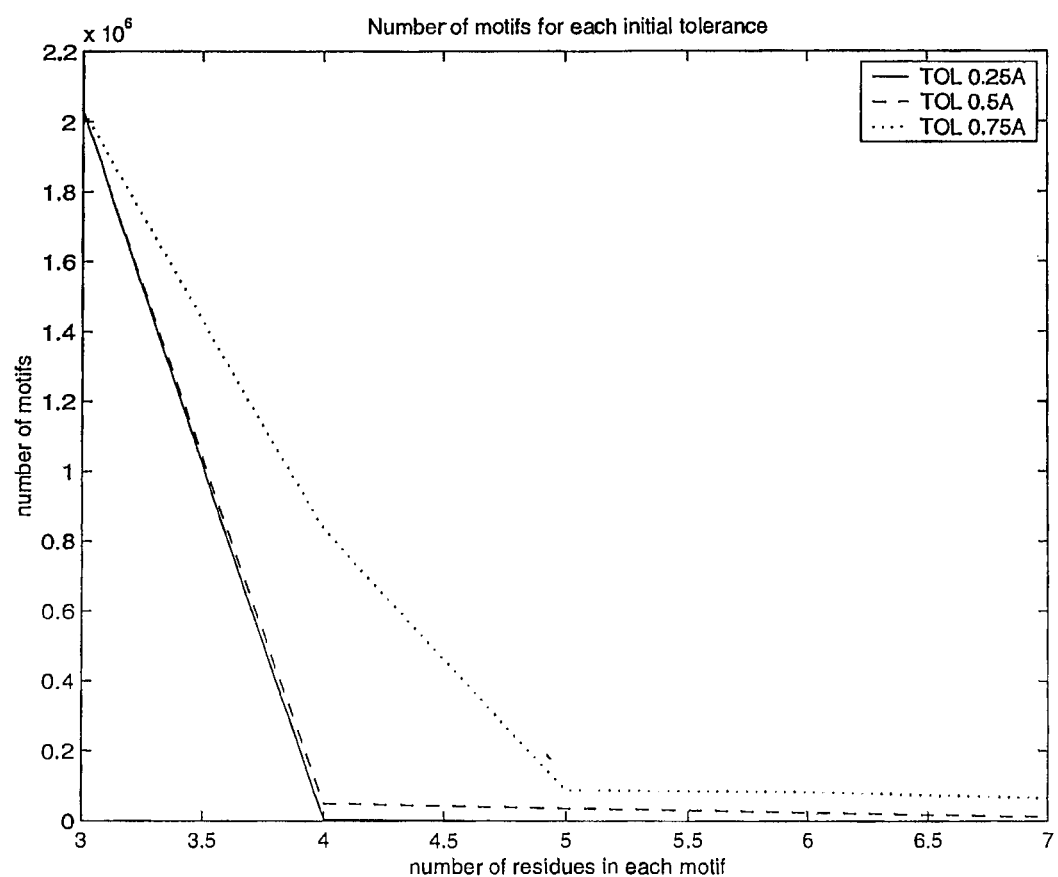

FIG. 29. Number of motifs verses size of motifs.

Figure 30:
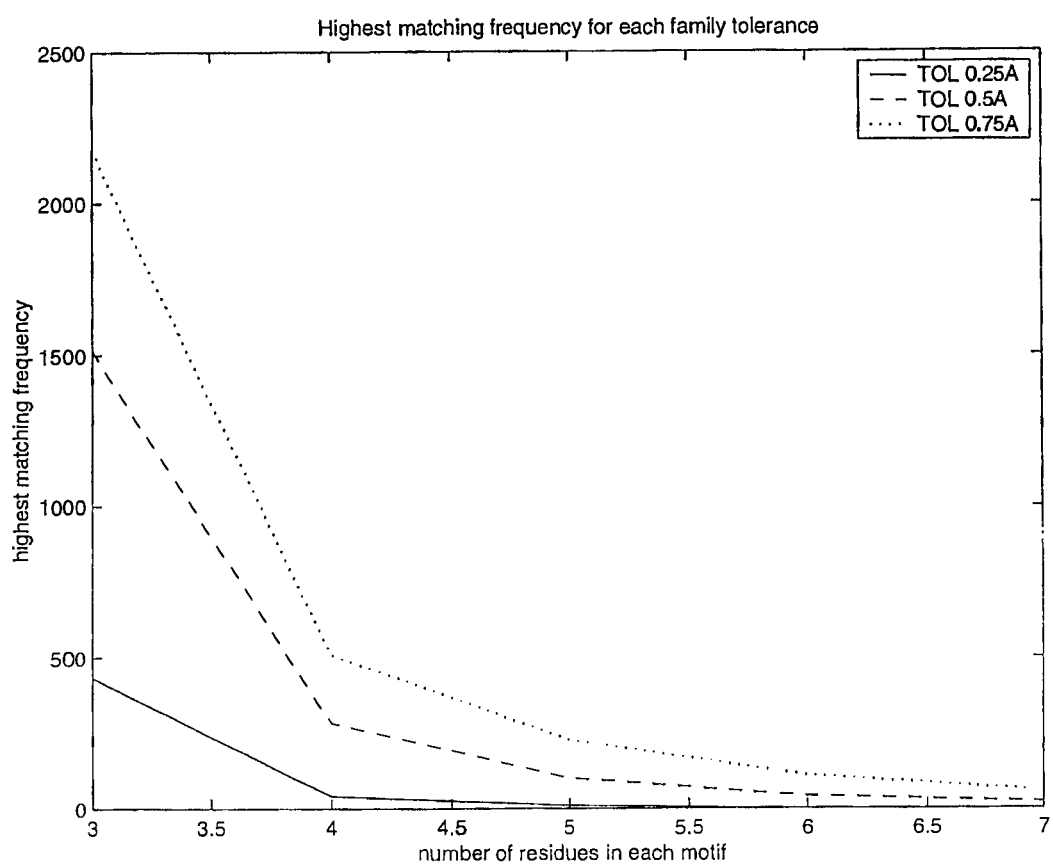

FIG. 30. Highest matching frequency for each family tolerance.

Figure 31:
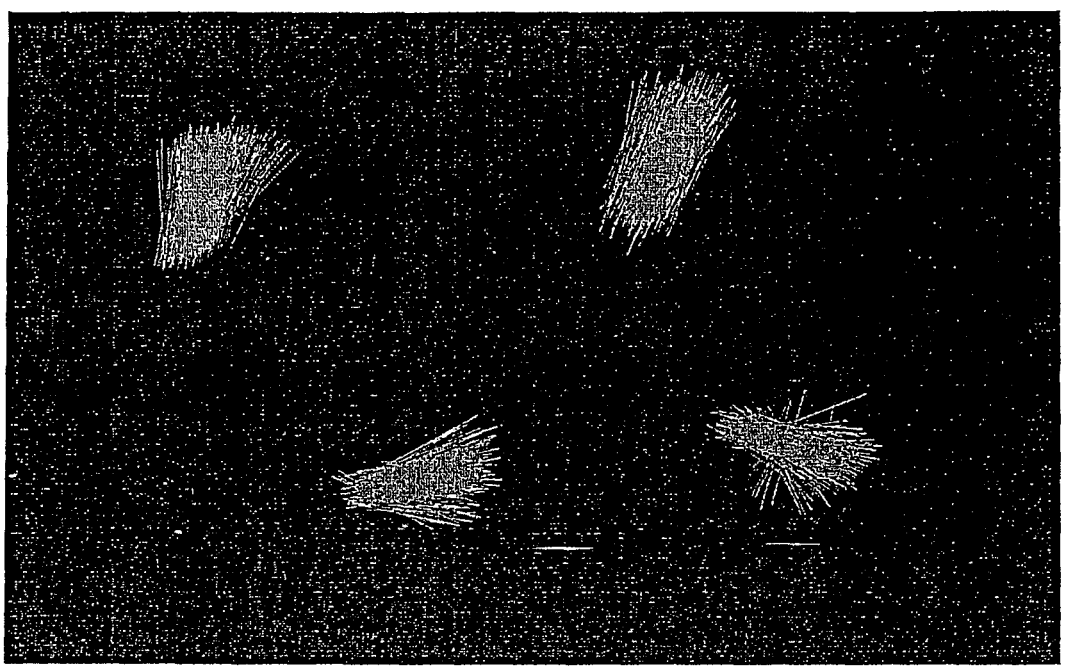

FIG. 31. Representative 4-motif C29.

Figure 32:

FIG. 32. Representative 5-motif C30.

Figure 33:
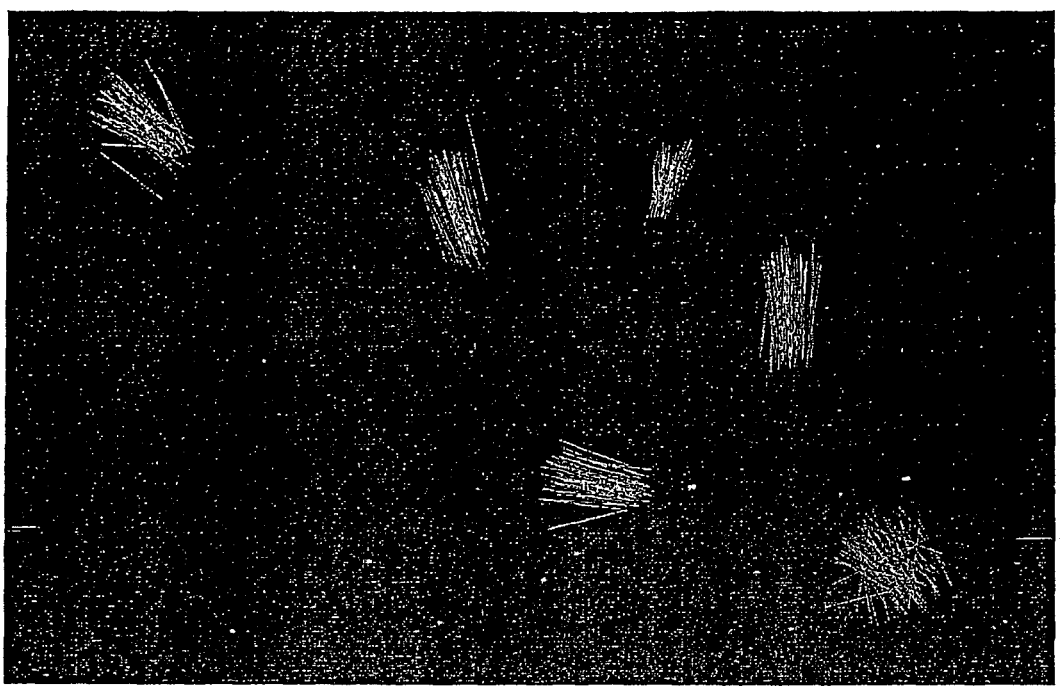

FIG. 33. Representative 6-motif C1.

Figure 34:
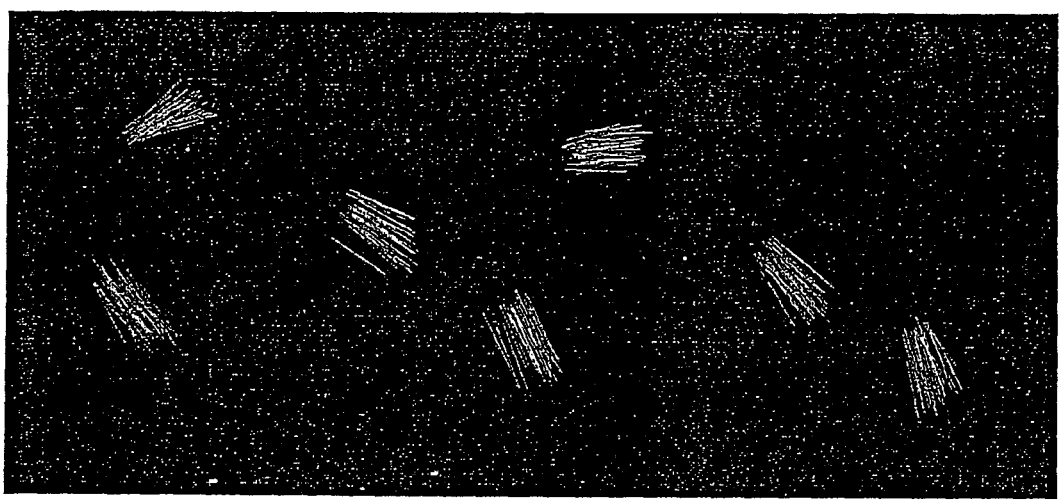

FIG. 34. Representative 7-motif C10.

FIG. 35. Pseudo-code for finding the matching frequency of surface patches.

FIG. 36. Pseudo-code for initial patch creation.

FIG. 37. Pseudo-code for the creation of higher order N-patches.

Figure 38:
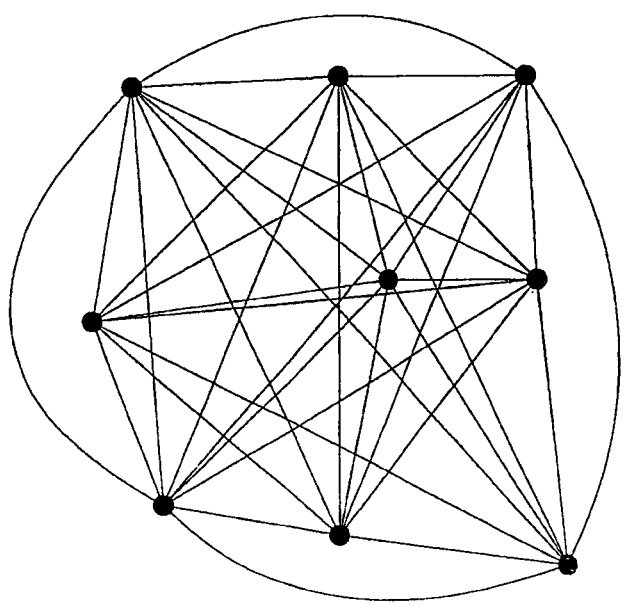

FIG. 38. The complete graph $K_9$ for a 9-patch.

FIG. 39. a) Some scaffolds that match the common β-turns motifs, b) Some scaffold that match the common loop motifs, and c) A scaffold that match a common six-residue protein-protein interaction surface. The common motifs of the queries are shown in thicker lines in section a, b and c.

Table 1. RMSD matrix of the results obtained from filtered centroid sorting refinement of the 7 clusters formed from the fourth cycle of the $k^{th}$-nearest neighbor clustering algorithm.

Table 2. RMSD matrix of the eight clusters formed from clustering algorithm and explicit division of cluster three into two clusters.

Table 3. RMSD matrix of the nine clusters formed from clustering algorithm, explicit division of cluster three into two clusters and explicit inclusion of the mean of type I' in the initial seeds.

Table 4. Comparison of the unique peaks obtained using a NEIGHBOR_LIMIT of 0.3 with the unique peaks obtained using higher NEIGHOUR_LIMIT of 0.4, 0.5, 0.6 and 0.7. [1]The unique-peak number obtained using NEIGHBOR_LIMIT of 0.3 that is most similar to the unique peak obtained using higher NEIGHBOR_LIMIT. [2]The unique-peak number obtained using the higher NEIGHBOR_LIMIT that is shown in the header. [3]The RMSD value from the superimposition of the unique-peaks obtained using the NEIGHBOR_LIMIT of 0.3 and obtained using the corresponding higher NEIGHBOR_LIMIT.

Table 5. RMSD matrix of the 39 clusters. All the loops of cluster x (row x) are superimposed to the peak structures of cluster y (column y) and the resulting average RMSD obtained is shown in row x and column y. Since the average RMSD for row x, column y is very similar to that of row y, column x, the two values are averaged and place in row x and column y where x is greater or equal to y. The intracluster RMSD are highlighted by background shading. The average intercluster RMSD that is within 0.2 from the highest intracluster RMSD of 0.56 are also highlighted by background shading.

Table 6. Summary of results for 4-residue motifs.

Table 7. RMSD values for clustering of 4-residue motifs for initial families TOL 0.75 and inter TOL 0.5 with sealevel 0.25 times the peak.

Table 8. Summary of results for 5-residue motifs.

Table 9. RMSD values for clustering of 5-residue motifs for initial families TOL 0.75 and inter TOL 0.7 with sealevel 0.125 times the peak.

Table 10. Summary of results for 6-residue motifs.

Table 11. RMSD values for clustering of 6-residue motifs for initial families TOL 0.75 and inter TOL 0.7 with sealevel 0.125 times the peak.

Table 12. Summary of results for 7-residue motifs.

Table 13. RMSD values for clustering of 7-residue motifs for initial families TOL 0.75 and inter TOL 0.9 with sealevel 0.125 times the peak.

Table 14. The secondary structure classifications as made by DSSP.

Table 15. The secondary structure of the original clusters for 4-residue motifs.

Table 16. The secondary structure of the original clusters for 5-residue motifs.

Table 17. The secondary structure of the original clusters for 6-residue motifs.

Table 18. The secondary structure of the original clusters for 7-residue motifs.

Table 19. The proportion of motifs not spanned by a single α-helix.

Table 20. The classification of the best 30 seeds of secondary structure not spanned by a single α-helix.

Table 21. Summary of results for the non-single α-helix seeds.

Table 22. RMSD values for clustering of 4-residue motifs for non-single-α-helix seeds greedy tolerance 0.5 Å with sealevel 0.25 times the peak matching frequency.

Table 23. The secondary structure of the non-single-α-helix clusters clusters for 4-residue motifs.

Table 24. The proportion of motifs in the non-single-α-helix clusters that do not contain a single α-helix.

Table 25. The secondary structure of the non-single-α-helix clusters for 7-residue motifs.

Table 26. The (x, y, z) coordinate of the mean structure of the $5^{th}$-least-common cluster of the β-turns, loops and surface motifs.

DETAILED DESCRIPTION OF THE INVENTION

The present invention describes the clustering of charged protein surface patches or regions, and the clustering of side chains of continuous and discontinuous surfaces of proteins into distinct motifs. These motifs are used as "descriptors" to design molecules that mimic specific, common protein shapes. This is achieved by using these common protein motifs as a screen in a virtual screening of a virtual library and in de novo molecular design and engineering. This approach results in the discovery of molecules that mimic common protein shapes. The synthesis of individual molecules or libraries of molecules that mimic protein shapes will result in the discovery of biologically active molecules that are capable of modulating protein function. In this respect these motifs or descriptors are used to select molecules from the vast chemical universe that match common protein shapes.

In order to define the common structural features of proteins used in molecular recognition, the present inventors have derived a new classification system to describe protein structure, based on the location and orientation of side chains, and based on the shape of the charged protein surface patches or regions, such as in protein-protein interaction regions. In particular the present inventors have focussed on defining the side chain arrangements of β-turns and loops, as these are primarily responsible for molecular recognition, as well as the side chain arrangements of contact surfaces.

Therefore, the present invention provides the identification of common protein motifs and the use of these as descriptors in molecular design. Libraries of molecules that mimic protein shapes should be valuable for the discovery of biologically active molecules using high throughput screening methodologies. These libraries would form the foundation for the discovery of novel drugs.

As used herein, by "protein" is meant an amino acid polymer. Amino acids may be D- or L-amino acids, natural and non-natural amino acids as are well understood in the art.

Chemically modified and derivatized amino acids are also contemplated according to the invention, as are well understood in the art.

A "peptide" is a protein having less than fifty (50) amino acids.

A "polypeptide" is a protein having fifty (50) or more amino acids.

As used herein, a "protein surface shape" is any three-dimensional property or feature of a protein surface, such as may be described according to amino acid side chain location and orientation or by surface charge distribution.

In one particular embodiment, the property or feature is a three-dimensional side-chain location and orientation of each of two or more amino acids of a protein.

In another particular embodiment, the property or feature is a three-dimensional charge distribution of one or more surface regions of a protein.

Suitably, the protein surface shape is of, comprises or derived from, a structural feature of a protein. Such a structural feature may, for example, be a contact surface that interacts with another protein or other molecule such as a nucleic acid, nucleotide or nucleoside (e.g. ATP or GTP) carbohydrate, glycoprotein, lipid, glycolipid or small organic molecule (e.g. a drug or toxin) without limitation thereto. Therefore, for the purposes of exemplification, a domain may be a ligand-binding domain of a receptor, a DNA-binding domain of a transcription factor, an ATP-binding domain of a protein kinase, chaperonin or other protein folding and/or translocation enzyme, a receptor dimerization domain or other protein interaction domains such as SH2, SH3 and PDB domains, although the skilled person will appreciate that the present invention is not limited to these particular examples.

Structural features of proteins may include loops, β-turns or other contact surfaces, helical regions, extended regions and other protein domains.

Preferred structural features are in the form of loops, β-turns or other contact surfaces More preferred structural features are loops and contact surfaces.

As used herein, "contact surfaces" are protein surfaces having amino acid residues that contact or interact with another molecule, such as another protein. An example of a contact surface is the ligand-binding surface of a cytokine receptor, although without limitation thereto.

Contact surfaces may be composed of one or more discontinuous and/or continuous surfaces.

By "discontinuous protein surface" is meant a protein surface wherein amino acid residues are non-contiguous or exist in discontinuous groups of contiguous amino acid residues.

In this regard, it will be appreciated that β-turns and loops are examples of a "continuous protein surface". That is, a protein surface that comprises a contiguous sequence of amino acids.

According to the invention, it is preferred that the location and orientation in 3D space of each amino acid side-chain is simplified as a Cα-Cβ vector.

In one embodiment, a "descriptor" is a representation of common, or at least topographically related, amino acid side-chain locations and orientations in 3D space derived from two or more amino acids of each of two or more proteins. Typically, a descriptor corresponds to a cluster of Cα-Cβ vectors obtained from two or more β-turns, loops, protein contact surfaces, helices or other structural features. Clusters are essentially groupings of β-turns, loops or protein contact surfaces with common 3D topography. Clusters may be created by any algorithm that compares similarity and/or dissimilarity between constituent Cα-Cβ vectors of β-turns, loops or protein contact surfaces. Examples of clustering algorithms are provided in detail hereinafter.

In another embodiment, a "descriptor" is a representation of one or more common, three-dimensional distributions of charge across one or more surface regions of two or more proteins.

According to this embodiment, it is preferred that said descriptor represents four or more grid points.

Preferably, respective grid points are 0.2 to 2.0 angstrom apart in three-dimensional (3D) space.

In particular embodiments, respective grid points may be 0.2, 0.5, 1.0, 1.2, 1.5 or 2.0 angstrom apart in three-dimensional (3D) space.

It will also be appreciated that grid point dimensions may be modified within the ranges recited above according as desired. For example, protein surface regions that contribute significantly to protein-protein interaction may be represented by relatively tighter, less spaced-apart grid points. Conversely, protein surface regions that have less contribution to protein-protein interaction may be represented by relatively losser, more spaced-apart grid points.

It will further be appreciated that in particular embodiments, descriptors of common surface shape may be in the form of "average" surface shape, inclusive of "mean", "median" and "mode" surface shape.

Preferably, the common surface shape is a "mean" surface shape.

As already described hereinbefore, a side-chain location and orientation in 3D space, preferably simplified as a Cα-Cβ vector, is required of at least two amino acids of each said β-turn, loop or contact surface.

In one embodiment, side-chain location and orientation of four β-turn or loop amino acids is required.

In another embodiment, side-chain location and orientation of at least three amino acids is required for a contact surface.

In particular embodiments, four, five, six or seven amino acid side-chain locations and orientations are required for a contact surface.

In some cases, descriptors are produced from protein structural information extracted from a source database such as the Protein Data Bank. In such cases, it is preferred that only non-homologous protein chains with relatively low homology (e.g. no greater than 25%) to other proteins are used. This reduces biased sampling caused by the presence in the source database of multiple structures that are minor variants of each other.

In other cases, descriptors may be produced from protein structural information produced de novo, or from X-ray crystallographic or NMR determinations of protein 3D structure.

In light of the foregoing, it will be appreciated that the invention provides classification of proteins according to common amino acid side-chain locations and orientations to thereby produce a representation of common spatial elements of protein surfaces.

As will be described in more detail hereinafter, the present inventors to date have identified at least 9 β-turn, 39 loop and 240 protein contact surface shapes that occur with high frequency and may be useful in molecular database screening and library design.

For the purposes of database searching, a number of options are available for suitable representation of Cα-Cβ vectors, whether as a database entry or as a query:—

(A) as a distance matrix;
(B) as a dihedral angle (δ) formed between respective Cα-Cβ vectors;

(C) as angles $a_1$ and $a_2$ formed between respective Cα-Cβ vectors.

Explanations of these representations are provided in Lauri & Bartlett[56] and International Publication WO 00/23474.

A preferred representation of Cα-Cβ vectors is as a distance matrix.

It will also be appreciated that a preferred representation of surface charge grid points is as a distance matrix.

A computer-searchable database may be an existing database such as the Protein Data Bank, Cambridge Structural Database, Brookhaven Database or may be a database constructed de novo. For the purpose of database searching, entries may be in the form of representations of proteins, peptides or other organic molecules. It is preferred that entries in searchable protein databases are in the form of charged surface or Cα-Cβ simplifications of constituent amino acid side chains. In cases where the searchable database comprises non-protein organic molecules (such as the Cambridge Structural Database), entries may typically be represented according to charge surface or 3D coordinate of particular atoms or groups of atoms (such as particular carbon, nitrogen and oxygen atoms, for example).

Suitably, a computer program is used for database searching.

Preferably, said computer program is the VECTRIX program, as described in International Publication WO 00/23474.

It will therefore be appreciated that the database searching method of the invention is capable of identifying one or more molecules, or portions of said molecules, that mimic common protein surface shapes. These molecules may then be used to construct virtual or synthetic chemical libraries that have been focussed by selecting molecules that are more likely to mimic the common protein surface shapes.

So that the invention may be more properly understood and put into practical effect, the skilled person is directed to the following non-limiting examples.

EXAMPLES

1 The Clustering of β-Turns 1.1 Background

Protein structure comprises stretches of secondary structure (helices or β-sheets) that are joined by turns, which enable a reversal in chain direction. These turns are normally positioned on the surfaces of proteins and allow the formation of the globular protein interior[1]. β-turns[2-4] are more common than the tighter coiled γ-turns and the looser coiled α-turns and have been defined as four residue segments of polypeptides in which the distance between $c_{\alpha i}$ and $c_{\alpha i+3}$ is less than 7 Å, and that the central residues are not helical[5]. β-turns encompass 25% of residues in proteins[6], are important for protein and peptide function[2,7-9], and are an important driving force in protein folding[2,10,11]. Consequently, there have been numerous studies on the design and development of β-turn mimetics[7,12-22].

Despite the importance of side chain spatial arrangement in molecular recognition, the conformations of β-turns are currently classified in terms of the main chain dihedral angles, φ and ψ[3,5,23-25]. Although this classification of β-turns has been extremely useful and has been used widely to design peptidomimetics, it makes very little functional sense. Each type of β-turn in the current classification can have two or more clusters of side chain spatial arrangement, and different types of β-turns can have the same side chain spatial arrangement.

There have been two reports on the classification of β-turns based on the arrangements of the side chains.[26] Whilst the β descriptor of Ball et al[27] defines some global structural characteristics of the turns, it is clearly an oversimplification, as it only considers two of the possible four side chain positions and used only a small data set of 154 experimentally derived β-turns. Garland and Dean[28,29] have found common motifs for four subsets of. β-turns, $c_\alpha$ atom doublets, $c_\alpha$ atom triplets, $c_\alpha$-$c_\beta$ vectors doublets and $c_\alpha$-$c_\beta$ vectors triplets by hierarchical clustering the conformations of side chains. However, the clustering was not based on experimental data, but was based on all possible permutations of selecting doublets or triplets out of each of the eleven idealized β-turn types. Furthermore, it is not necessary to explicitly identify subsets of the β-turns for mimicry as have done by Garland and Dean[28,29]. This is because it is possible to derive these subsets from the whole β-turn using more sophisticated searching algorithms[30] then considered by Garland and Dean.

1.2 Method 1.2.1 β-Turns Clustering 1.2.1.1 Extraction of β-Turns from Protein Data Bank (PDB)

A high resolution and non-redundant database of β-turns are required for the determination of common β-turn motifs that exist in proteins. To ensure high quality data, only high-resolution structures with a resolution of ≤2 Å and an R factor ≤20% were extracted from the 1997 release of the Protein Data Bank[31]. Furthermore, to eliminate the biased sampling in the PDB caused by the presence of multiple structures that are minor variations of a particular protein chain, only non-homologous protein chains with ≤25% homology with other protein chains were used. The distribution of the $c_{\alpha 1}$-$c_{\alpha 4}$ distances of the resulting 3984 four-residue segments that are not helical nor n-sheets is plotted in FIG. 1 and a major peak is observed at $c_{\alpha 1}$-$c_{\alpha 4}$ distances of 5.5 Å. In 1973, Lewis[24] concluded that β-turns have $c_{\alpha 1}$-$c_{\alpha 4}$ distance of ≤7 Å based on the distribution of the $c_{\alpha 1}$-$c_{\alpha 4}$ distances of only eight X-ray diffraction determined structures. To remove any possible biases caused by noisy data, the outliners of the major peak at 5.5 Å were removed by eliminating the turns with $c_{\alpha 1}$-$c_{\alpha 4}$ distance of less than 5 Å or greater than 6.2 Å, resulting in 2675 β-turns in the database.

1.2.1.2 Representation of Data

The present inventors motivations for clustering using $c_\alpha$-$c_\beta$ vectors are several fold. The $c_\alpha$-$c_\beta$ vector describes the initiation of the side chain geometry, and is well defined experimentally as it is anchored to the backbone. This is in contrast to the more flexible penultimate side chain atoms. Importantly, most mimetic strategies involve anchoring $c_\alpha$-$c_\beta$ bonds to a non-peptidic scaffold, the extra atoms of the side chain providing a degree of flexibility in molecular recognition. We therefore consider that clustering according to $c_\alpha$-$c_\alpha$ vectors is functionally significant, when the aim is to use the motifs identified to design molecules that match specific motifs.

Each of the 20 naturally-occurring amino acids, except for glycine, posses a $c_\alpha$-$c_\beta$ vector due to the covalent bond between the central a carbon and the β carbon of the side chain. For β-turns that contains a glycine, the glycine residue was mutated to alanine to generate the required $c_\alpha$-$c_\beta$ vector. This was achieved by superimposing an ideal alanine structure onto the n, $c_\alpha$ and c' atoms of the glycine residue.

An important advance in database searching has been made by representing 3D structures in terms of the relationship between atoms located in distance space, rather than Cartesian space[30,32]. A location in distance space is defined by distances between atoms, expressed in the form of a distance matrix. Distance matrices are therefore coordinate independent, and comparisons between distance matrices can be made without restriction to a particular frame of reference, such as is required using Cartesian coordinates. It is important to emphasize that an arrangement of atoms and its mirror image are described by identical distance matrices. A root mean squared deviation (RMSD) can be used to alleviate this ambiguity. The four $c_\alpha$-$c_\beta$ vectors of each β-turn are represented by a distance matrix rather than a Cartesian coordinate system. Since there are four pairs of distances between each pair of $c_\alpha$-$c_\beta$ vectors ($c_{\alpha1}$-$c_{\alpha2}$, $c_{\alpha1}$-$c_{\beta2}$, $c_{\beta1}$-$c_{\alpha2}$ and $c_{\beta1}$-$c_{\beta2}$) and there are six possible pairs of $c_\alpha$-$c_\beta$ vectors (1-2, 1-3, 1-4, 2-3, 2-4 and 3-4), then 24 distances are required to represent the 3D topography of a β-turn. The distances between $c_{\alpha i}$-$c_{\beta i}$ were not included because these bonded distances are relatively invariant between β-turns when compared to the non-bonded distances used.

1.2.1.3 $k^{th}$-Nearest Neighbor

The $k^{th}$-nearest neighbor clustering algorithm[33,34] employed here for clustering of β-turns is basically a simple-linkage clustering algorithm[35] in which every member is initially assigned to a different cluster and clusters are subsequently merged if the minimum distance between a member of a cluster and a member of another cluster is less than some threshold. The $k^{th}$-nearest neighbor clustering algorithm[33,34] differs from simple-linkage clustering algorithm in that the distance between members is replaced by a dissimilarity measure defined below.

$d_k(x)$ is defined as the Euclidian distance from observation x to the $k^{th}$ nearest observation. $v_k(x)$ is defined as the volume enclosed by the sphere, centering at observation x and having a radius of $d_k(x)$. The density at observation x, f(x), is defined as $k/v_k(x)/N$ where N is the total number of observations. The dissimilarity measure between observations $x_i$ and $x_j$, $D(x_i, x_j)$, can be calculated from the following definitions. First, $x_i$ and $x_j$ are said to be adjacent if the Euclidean distance between the two points is less than $d_k(x_i)$ or $d_k(x_j)$. If the observation $x_i$ and observation $x_j$ are not adjacent, then the dissimilarity measure, $D(x_i, x_j)$, is set to infinity. Otherwise, $D(x_i, x_j)$ is defined as the average of the inverse of the density, i.e. $D(x_i, x_j)=(1/f(x_i)+1/f(x_j))/2$. Clustering should group together regions of high density separated by regions of low density. Effectively, by defining the dissimilarity measure as the inverse of the density, this algorithm first groups together adjacent points or clusters that have high-density.

The $k^{th}$-nearest neighbor algorithm from the commercially available SAS/STAT program[36] was used to cluster the distance matrices representing the topography of the $c_\alpha$-$c_\beta$ vectors of the β-turns. The option 'k' is called the smoothing parameter. A small value of 'k' produces jagged density estimates and large numbers of clusters, and a large value of 'k' produces smooth density estimates and fewer clusters. A 'k' value of two was used because only a rough estimate of clusters is required here. The clusters obtained here are used as initial seeds for the filtered nearest centroid-sorting algorithm described below.

1.2.1.4 Filtered Nearest Centroid Sorting Clustering Algorithm

The nearest centroid sorting clustering algorithm by Forgy[37,38] requires a prior estimate of some initial seeds. The algorithm assigns each observation to the nearest initial seed to form temporary clusters. The seeds are then replaced by the means of the temporary clusters and the process is repeated until no further changes occur in the clusters. After the $k^{th}$ nearest neighbor clustering of the β-turns, a modified form of the 'nearest centroid sorting algorithm[37], filtered nearest centroid sorting clustering algorithm was used to refine the clustering. This method superimposes observations in Cartesian coordinate space and thus removes the mirror image problem inherited from the distance matrix representation in the $k^{th}$ nearest mean clustering algorithm. The reasons for this two-stage clustering process are: 1) Hierarchical clustering based on RMSD could not be used in the first place because the number of observations is larger than the limit set by the SAS/STAT program[36] and 2) Faster and leaner approximation methods, such as nearest centroid sorting[37,38] or K-means clustering algorithm[39] could not be used without prior estimate of initial seeds.

The filtered nearest centroid sorting algorithm is basically the same as the nearest centroid sorting algorithm except that if the minimum RMSD of a β-turn to the mean structures is above some definable threshold, then the turn is considered too remote and therefore not assigned to the temporary clusters. In latter iterations, these unassigned turns are superimposed onto the new mean structures of the new temporary clusters and if the minimum RMSD is below the threshold, then they are assigned to the new temporary cluster. The aim of this filtering is to remove the turns that are very different from the mean structures, so as not to bias the mean. Furthermore, 100% of the β-turns do not need to be clustered, only a major proportion is required. The filtered nearest centroid-sorting algorithm was implemented in a C++ program entitled "fncsa_cluster_analysis.cpp".

1.2.2 Cluster Analysis 1.2.2.1 Vector Plots of β-Turns

It is difficult to visualise the 24 distances that represent the topography of a β-turn. A vector plot is used to aid the visualization by approximating the 24 distances with four torsional angles θ1, θ2, θ3 and θ4 (see FIG. 2). θ1 is defined as the torsional angle between $c_{\beta1}$, $c_{\alpha1}$, $c_{\alpha2}$ and $c_\beta$. θ2 is defined as the torsional angle between $c_{\beta2}$, $c_{\alpha2}$, $c_{\alpha3}$ and $c_{\beta3}$; θ3 is defined as the torsional angle between $c_{\beta3}$, $c_{\alpha3}$, $c_{\alpha4}$ and $c_{\beta4}$; and θ4 is defined as the torsional angle between $c_{\beta1}$, $c_{\alpha1}$, $c_{\alpha4}$ and $c_{\beta4}$. Since the distances between adjacent $c_\alpha$ atoms in a β-turn are relatively constant due to the nature of the peptide bond, the four torsional angles should represent the essential conformational feature of a β-turn. The four torsional angles are plotted as a vector from (θ1, θ2) (represented by the symbol 'x') to (θ3, θ4). Effectively, this plot approximates the 24 distances of β-turns to four torsional angles (θ1, θ2, θ3 and θ4), which are plotted as a vector on a 2D graph. The torsional angles are periodic. A value of x is equivalent to x-360, x+360 and so on. To remove the graphing problem associated with the periodic nature of the torsional angles, each torsional value is transformed into a period that is closest to the torsional angles of the first β-turn.

1.2.2.2 Visualizing β-Turn Clusters

Another method to visualize the clusters of β-turns is to superimpose the 3D structures of all the turns in a cluster. Superimposition is performed from the four $c_\alpha$-$c_\beta$ vectors of a β-turn to the four $c_\alpha$-$c_\beta$ vectors of the mean structure of the cluster. For glycine, the $c_\alpha$-$c_\beta$ vector is obtained by superimposing a standard alanine residue to the n, $c_\alpha$ and c' atoms of the backbone of the glycine residue. The "fncsa_cluster_analysis.cpp" program outputs the coordinates of the superimposed structures in a multi-structure pdb file format which is visualised using the program InsightII of Molecular Simulation Inc.

There are a few steps in the calculation of the mean of a cluster in Cartesian coordinate space. Firstly, an initial mean structure for a cluster is set to be the first β-turn that does not have glycine or proline residue. Then each β-turn is superimposed to this temporary mean structure based on the coordinates of the $c_\alpha$-$c_\beta$ vectors. After the superimposition, a new temporary mean structure is computed by averaging the x, y and z coordinates. The latter two steps are repeated until successive mean structures differ by less than some arbitrary threshold.

1.2.2.3 Calculation of the RMSD Matrix of all the Clusters

RMSD matrix is calculated to examine the performance of the clustering by assessing the dissimilarity within and between clusters. Each cluster is compared with every other cluster so that the row and column number of the matrix represents the cluster number. The value in a cell at row x and column y represents the mean RMSD when all the β-turns in cluster x is superimposed to the mean structure of cluster y. The diagonal of the matrix with row x and column x represents intra-cluster RMSD while the other cells represents inter-cluster RMSD. Values in row x and column y are not necessarily similar to values in row y and column x because the former represent the mean RMSD of the β-turns in cluster x superimposed onto the mean structure of cluster y and the latter represent the mean RMSD of the β-turns in cluster y superimposed onto the mean structure of cluster x. However, the two numbers are very similar.

1.3 Results
1.3.1 Clustering

The $k^{th}$ nearest neighbor cluster algorithm was used to cluster the 2675 β-turns in the database. The mean structure (seed) of each of the outputted 570 clusters was calculated by averaging each of the 24 distances representing the topography of β-turns. In the second cycle, $k^{th}$ nearest clustering was performed on these 570 seeds and 117 seeds were obtained. The third cycle of $k^{th}$ nearest clustering produced 25 seeds and the fourth cycle produced 7 seeds. Both the 7 and 25 seeds were examined in more detail prior to the selection of final β-turn clusters.

To determine a reasonable value for the threshold used in the filtered nearest centroid sorting algorithm, the seven seeds obtained from the $k^{th}$ nearest neighbor clustering were refined using filtered centroid sorting algorithm with four different threshold values, an RMSD of 0.6, 0.65, 0.7 and infinity (no threshold at all). The results show that the lower the threshold, the higher the percentage of β-turns that are rejected (not assigned to a cluster). The percentages of rejection for the four threshold values are 19%, 14%, 8% and 0% respectively. The RMSD matrices of the results were calculated and the average of the mean inter-cluster RMSD are 1.05, 0.95, 1.03 and 1.15 respectively. Ideally, one would like clusters to differ as much as possible, and hence have a high inter-cluster RMSD. The mean inter-cluster RMSD was lowered in going from a threshold of infinity to 0.7 and to 0.65, however it got higher in going from 0.65 to 0.6. The average of the mean intra-cluster RMSD are 0.36, 0.36, 0.40 and 0.44 respectively. In this instance, low intra-cluster RMSD are favored, therefore emphasizing that the observations in each cluster are similar. There were improvements in the intra-cluster RMSD in going from a threshold of infinity to 0.7 and from 0.7 to 0.65. However there was no improvement in going from a threshold of 0.65 to 0.6. As a compromise of the conflicting interest of percentage rejection, inter-cluster RMSD and intra-cluster RMSD, a filter threshold of 0.65 was chosen.

To determine if the 25 seeds from the third cycle or the 7 seeds from the fourth cycle of the $k^{th}$ nearest neighbor clustering best represent the side chain spatial arrangements of β-turns, both the results were subjected to the filtered centroid sorting algorithm followed by the calculation of the RMSD matrix. The RMSD matrix for the 7-clusters is shown in Table 1. The Clustering process aims to define clusters that have low intra-cluster RMSD separated by high inter-cluster RMSD. For the 25 clusters, the average of the mean intra-cluster RMSD is 0.31, the average of the mean inter-cluster RMSD is 1.11 and the maximum mean intra-cluster RMSD is 0.42. For the 7 clusters (Table 1), the average of the mean intra-cluster RMSD is 0.36, the average of the mean inter-cluster RMSD is 0.95 and the maximum mean intra-cluster RMSD is slightly higher, 0.49. The results show that the clustering into the 7 clusters is not as good as the clustering into the 25 clusters, the intra-cluster RMSD was larger (0.36 compared to 0.31) and the inter-cluster was smaller (0.95 compared to 1.11). However, since this is not a drastic difference and the 7-clusters still give reasonable intra-cluster RMSD, the more tractable 7-clusters result was preferred over the 25-cluster result.

1.3.2 Refinement of the Clustering

Vector graphs, as described in the method section, were used to visualize the seven-cluster result (FIG. 3). The figure shows that all the clusters except for cluster three have a reasonable uniform distribution from a single mode. Cluster three, however, seems to have two modes. One mode with θ4≥70° and the other mode with θ4<70°. Furthermore, the RMSD matrix in Table 1 shows that cluster three has the most varied intra-cluster RMSD of 0.49. To determine if cluster three should remain as one cluster or should be divided into two clusters, a practical step was used in which cluster three was divided into two clusters (one cluster with θ4≥70° and another cluster with θ4<70°) and the new result assessed by comparison with the original result. The resulting eight clusters were refined once more using the filtered nearest centroid-sorting algorithm. The RMSD matrix and the vector plot for the new eight clusters were calculated and the results are shown in Table 2 and FIG. 4 respectively. In dividing cluster three into two clusters, the mean intra-cluster RMSD has not changed significantly (from 0.36 to 0.35), the maximum intra-cluster RMSD improved from 0.49 to 0.43, the minimum intra-cluster RMSD improved from 0.31 to 0.29, the mean inter-cluster has changed from 0.95 to 0.93 and finally the percentage of turns represented by the clusters remained the same at 86%. The vector plot in FIG. 4 shows that the β-turns in each cluster distribute within a narrow range about a single mode. These results suggested that the eight clusters system is a better representation of β-turn motifs compared to the seven clusters system.

It was observed that type I' β-turns were not included in any of the eight clusters, they were rejected in the filtered nearest centroid sorting clustering because their RMSD with the mean of the eight clusters were more than the threshold of 0.65. This reflects a weakness in the $k^{th}$ nearest mean algorithm as it does not identify a seed near the low frequency type I' β-turns. Since FIG. 9 indicates that there is a cluster near the type I' β-turns, the mean of the type I' was calculated and the result was included together with the other eight initial seeds for the filtered nearest centroid sorting clustering. The RMSD matrix and the vector plot for the new nine clusters were calculated and the results are shown in Table 3 and FIG. 5 respectively. By the addition of the type I' average structure into the initial seeds, the mean intra-cluster RMSD has not changed significantly (from 0.35 to 0.36), the minimum and maximum intra-cluster RMSD remained the same, the mean inter-cluster worsen (from 1.25 to 1.1) and the percentage of β-turns classified improved from 86% to 90%. The vector plots in FIG. 5 shows that the β-turns in each cluster distribute within a narrow range about a single mode. These results suggest that the nine clusters system is a reasonable representation of β-turn motifs.

1.3.3 Mean Structures

The final nine-cluster result was also visualized by superimposing each β-turn in the clusters onto the clusters' mean structure (FIG. 6). The visual result is consistent with the mean intra-cluster RMSD value of each cluster in Table 3.

The cluster with the least amount of $c_\alpha$-$c_\beta$ vector spread (cluster 2, FIG. 6) corresponds to the smallest mean intra-cluster RMSD. It is interesting to note that the backbone structure can vary significantly although the $c_\alpha$-$c_\beta$ vectors are uniform within a cluster. A top view of the most uniform cluster, cluster 2 for example, shows that different backbone conformations can have similar $c_\alpha$-$c_\beta$ vector spatial arrangement (FIG. 7). In this instance, type I and type II β-turns are presenting the same $c_\alpha$-$c_\beta$ vector spatial arrangement. To appreciate the difference between the clusters, the mean structures of each cluster were superimposed based on the $c_{\alpha 1}$, $c_{\alpha}$ and $c_o$ atoms. The result of this superimposition is displayed in FIG. 8. The lowest inter-cluster RMSD (0.59) in FIG. 3 is between cluster 2 and cluster 4. The result in FIG. 8 also demonstrates that cluster 2 (red) and cluster 4 (green) are most similar and furthermore, provides a visual aid to understanding the meaning of an inter-cluster RMSD value of 0.59. The highest inter-cluster RMSD (2.38) exists between cluster 6 and 9 (Table 3). The result in FIG. 8 also demonstrates that cluster 6 (dark blue) and cluster 9 (grey) differ significantly.

The mean members of each cluster then become a query in a database searching strategy. This is described in more detail in Section 4.

2 Clustering of Loops of Proteins

2.1 Background

Loops are defined as any continuous amino acid sequence that joins secondary structural elements (helices and sheets). Consequently, loops are a superset of β-turns since there is no restriction on $c_{\alpha 1}$-$c_{\alpha 4}$ distances (as described above). Loops often play an important function as exemplified by their roles in ligand binding[40], DNA-binding[41], binding to protein toxin[42], forming enzyme active sites[43], binding of metal ions[44], binding of antigens by immunoglobulins[45], binding of mononucleotides[46] and binding of protein substrates by serine proteases[47]. Identifying common loops motifs, then using these as queries in virtual screening of virtual library strategies will provide a novel and powerful strategy for the design and synthesis of bioactive molecules.

2.2 Methods and Results

2.2.1 Extraction of Loops from Protein Data Bank

A database of loops was created by first extracting well refined (resolution of ≤2.0 Å and R-factor ≤20%) and non-homologous (≤25%) protein chains[48,49] from the 1999 release of the Protein Data Bank[31]. The program STRIDE[50] was then used to identify secondary structural elements (helices and sheets) of these chains. The linking regions, defined as the remaining residues that link these secondary structural elements or the protein terminus, were used for further analysis. The linking regions that consisted of four or more amino acid residues were divided into four residue segments, resulting in a total of 23650 four-residue loops. 319 of those loops were rejected because the distance between backbone atoms n, $c_\alpha$ and c' was not appropriate (≤0.8 or ≥2.0 Å). Each of the remaining 23331 loops was then simplified into four $c_\alpha$-$c_\beta$ vectors (FIG. 2a). Our motivations for clustering using $c_\alpha$-$c_\beta$ vectors are several fold. The $c_\alpha$-$c_\beta$ vector describes the initiation of the side chain geometry, and is well defined experimentally as it is anchored to the backbone. This is in contrast to the more flexible penultimate atoms in the side chain. Furthermore, most mimetic strategies involve anchoring $c_\alpha$-$c_\beta$ bonds to a non-peptidic scaffold, the extra atoms of the side chain provides a degree of flexibility in molecular recognition. We therefore consider that clustering according to $c_\alpha$-$c_\beta$ vectors is functionally significant[51], especially when the identified common motifs are used to direct peptidomimetic development.

2.2.2 Systematic Identification of Highly Populated Conformations (Seeds)

The present inventors have identified the appropriate seed points in order to cluster the loops of proteins. In this section the present inventors describe a process for identifying these seeds. By comparing each of the 23331 loops with all the other loops, all of the similar loops ("neighbors") having a RMSD value of less than a constant, NEIGHBOR_LIMIT, were identified and counted for each loop. A plot of the number of neighboring loops versus its frequency (the number of times this number of neighbors was found) using various NEIGHBOR_LIMIT is shown in FIG. 10. For most values of NEIGHBOR_LIMIT, as the number of neighboring loops increases, the frequency decreases and as the number of neighboring loops decreases, the frequency increases. However, with large NEIGHBOR_LIMIT (0.6 and 0.7), the frequency maximum is located between 200 to 600 neighboring loops instead of locating near the lower number of neighboring loops. This means that for large NEIGHBOR_LIMIT, it is more frequent to have 200 to 600 neighbors rather than 0-100 neighbors. The figure also shows the maximum number of neighboring loops for a particular NEIGHBOR_LIMIT, thereby giving an indication to the similarity between the loops. For example, the maximum number of neighboring loops is 1763 with NEIGHBOR_LIMIT of 0.7, 526 with NEIGHBOR_LIMIT of 0.4 and 146 with NEIGHBOR_LIMIT of 0.25.

Now that the number of neighboring loops has been determined for each loop, the next step was to identify (given a specific loop and its neighbors) the loop that has the largest number of neighbors (a peak). That is, the loop is marked as a peak if all the neighboring loops have lower or equal number of neighboring loops. The number of peaks for various NEIGHBOR_LIMIT is shown in FIG. 11. The figure shows that the number of peaks varied from 7818 to 13 as the NEIGHBOR_LIMIT varied from 0.25 to 0.7. However, since peaks with the number of neighbors of less than an arbitrarily chosen low SEA_LEVEL of 20 are not interesting as they are not significantly populated, the plot also shows the number of peaks with greater than the SEA_LEVEL number of neighbors. The number of peaks with greater than the SEA_LEVEL of 20 ranges from 56 to 3, decreasing with increasing NEIGHBOR_LIMIT.

Since some peaks can be quite similar to each other, filtering was performed to identify a set of unique peaks to represent the data. Two peaks are considered not sufficiently unique if the fraction of shared loops between the two peaks exceeds an OVERLAP_LIMIT value that was set to 20% of the total number of loops in the two peaks. From peaks with the largest number of neighbors to peaks with the lowest number of neighbors, the peaks were filtered out if they are not sufficiently unique when compared with all the previous chosen unique peaks. This definition, which is based on the fraction of overlap, is more discerning than a definition that is based on the RMSD distance between the average structures of the peak. FIG. 11 also shows the number of unique peaks as a function of NEIGHBOR_LIMIT. For NEIGHBOR_LIMIT of 0.4 and above, all the peaks were unique. However, for NEIGHBOR_LIMIT of less than 0.4, not all the peaks were unique.

As to the choice of the value for NEIGHBOR_LIMIT, the general principle is that the larger the NEIGHBOR_LIMIT value, the more the data is "generalized". We seek to find the largest generalization without the loss of the number of unique peaks with greater than 20 neighbors (SEA_LEVEL=20). FIG. 11 shows that the number of unique peaks with greater than twenty neighbors ranges from 3 to 40, decreasing with increasing NEIGHBOR_LIMIT value. When increasing NEIGHBOUR_LIMIT from 0.25 to 0.3, FIG. 11 illustrates that there is no significant reduction in the number of unique peaks. This contrasts to every other increase in NEIGHBOUR_LIMIT. Consequently a NEIGHBOUR_LIMIT of 0.3 retains the number of unique peaks whilst increasing the "generalization" of the data.

To examine the implication of the choice of 0.3 for NEIGHBOR_LIMIT, we determined whether the unique peaks obtained using a higher NEIGHBOR_LIMIT are a subset of those obtained using the lower NEIGHBOR_LIMIT of 0.3. For example, if the unique peaks for the NEIGHBOUR_LIMIT of 0.4 are a subset (are similar to) the unique peaks found for the NEIGHBOR_LIMIT of 0.3 then we would expect to find structurally similar unique peaks in both datasets. To do this, we systematically pair each of the unique peaks obtained using a higher NEIGHBOR_LIMIT with the most structurally similar unique peak obtained using a NEIGHBOR_LIMIT of 0.3. The results of pairing the 39 unique peaks obtained by using a NEIGHBOR_LIMIT of 0.3 with all the unique peaks obtained by using higher NEIGHBOR_LIMIT of 0.4, 0.5, 0.6 and 0.7 are shown in Table 4. The RMSD between the pairs of unique peaks for all comparisons ranged from 0.0 to 0.88. There are a significant number of peaks between datasets that have an RMSD of less then 0.3. This illustrates that in going to a higher NEIGHBOR_LIMIT similar unique peaks are found when compared to the unique peaks identified from the 0.3 NEIGHBOR_LIMIT. This is particularly true for unique peaks with high frequency. As you go down the rows of the table, the frequency of the unique peak decreases. As can be seen for low frequency unique peaks the structural match between the datasets can sometimes be poor. We conclude that the choice of a NEIGHBOR_LIMIT of 0.3 is a reasonable compromise between "generalization" and accuracy (number of unique peaks) and the resulting unique motifs are used as seeds for further clustering.

2.2.3 Filtered Centroid Sorting Clustering

After the systematic identification of unique peaks with greater than twenty neighbors, the filtered nearest centroid sorting algorithm described in section 1.2.1.4 was utilized to refine the clustering. The 39 unique peaks with greater than twenty neighbors were used as initial seeds for our filtered centroid sorting algorithm using various TOLERANCE. The percentage of data clustered, the average intracluster-RMSD, the average intercluster RMSD and the ratio of the latter two are plotted as a function of the TOLERANCE in FIG. 12. The figure shows that as the TOLERANCE increases, the percentage of data clustered and the intra-inter-RMSD ratio increases. At a TOLERANCE of 0.3, the percentage of data clustered, the average intracluster RMSD, the average intercluster RMSD and ratio of the latter two are 12%, 0.22, 0.95 and 0.11, respectively; at a TOLERANCE of 0.6 RMSD they are 71%, 0.42, 1.94 and 0.21, respectively; and at a TOLERANCE of 0.9, they are 100%, 0.51, 1.90 and 0.27, respectively. Therefore, there are opposing forces in the choice of tolerance. Higher tolerance is favored because of the greater percentage of data clustered, but is disfavored because of the higher intra to inter cluster RMSD ratio. Lower tolerance is favored because of the lower intra to inter cluster RMSD ratio but is disfavored because of the lower percentage of data clustered. From a mimetics perspective, it is more important to have a reasonable intracluster similarity (intra cluster RMSD) than to have high percentage clustered. To aid in the choice of intracluster RMSD and indirectly the choice of TOLERANCE, a plot of all the loops in cluster one formulated using various tolerances are shown in FIG. 13. The figure shows that with an average intracluster RMSD of 0.47, which corresponds with a TOLERANCE of 0.7 and 89% of the data clustered, the members in the cluster are sufficiently similar for loop mimetic purpose. The numbers of loops in each of the 39 clusters obtained using a tolerance of 0.7 is plotted in FIG. 14. The least populated cluster has 307 loops and the most populated cluster have 1048 loops.

2.2.4 Vector Plots of Loops

The vector graphs, as described in 1.2.2.1, for all the 39 clusters (FIG. 15) shows that the loops within a cluster have reasonably similar conformations.

2.2.5 Calculation of the RMSD Matrix of all the Clusters

An RMSD matrix is calculated to examine the performance of the clustering, by assessing the similarity within and dissimilarity between clusters (Section 1.2.2.3). The RMSD matrix, showing the average intra- and inter-clusters RMSD for all the 39 clusters, is shown in Table 5. The average intracluster RMSD of 0.47 and the vector graphs for all the clusters in FIG. 15 show that the loops within a cluster have similar conformations. The loops between clusters are dissimilar as the average intercluster RMSD is 1.91.

2.2.6 Average Linkage Clustering Algorithm

Based on the above mentioned RMSD matrix, we applied the average linkage clustering algorithm[36,52,53] to determine the structural relationship between the 39 clusters. In the average linkage clustering algorithm,[36,52,53] each structure is initially assigned to its own cluster of size one. Subsequently, clusters are merged if the average distance between all the structures in the two clusters fall within some threshold. The resulting hierarchical tree, obtained by applying the average linkage-clustering algorithm on the 39 clusters, is shown in FIG. 16. All the cluster numbers used in this paper follow the order from left to right of this hierarchical tree.

2.2.7 Distinct Clusters

Whilst each cluster contains a unique set of loops (no loops are in more then one cluster), do the 39 clusters represent overlapping-variation from a continuous spread or do they represent distinct clusters that do not overlap in hyperspace? To answer this question, we defined that two clusters are 'distinct' if the most frequent eighty-percent of the data in one cluster does not overlap with the most frequent eighty-percent of the data in the other cluster. The overlaps were computed for each of the following thirty-two descriptors of the loop conformation. Each $c_\alpha$-$c_\beta$ vector pair has four distances ($c_{\alpha 1}$-$c_{\alpha 2}$, $c_{\alpha 1}$-$c_{\beta 2}$, $c_{\beta 1}$-$c_{\alpha 2}$, $c_{\beta 2}$-$c_{\beta 2}$), so the six possible $c_\alpha$-$c_\beta$ vector pairs (1-2,1-3, 1-4, 2-3, 2-4, 3-4) of the four $c_\alpha$-$c_\beta$ vectors in a loop results in 24 distance descriptors. Furthermore, we also utilized all the possible six torsional angle descriptors between the four $c_\alpha$-$c_\beta$ vector and two torsional descriptors $c_{\alpha 2}$-$c_{\alpha 2}$-$c_{\alpha 3}$-$c_{\alpha 4}$ and $c_{\beta 2}$-$c_{\beta 2}$-$c_{\beta 3}$-$c_{\beta 4}$. Distinctions were made based on each of those thirty-two descriptors.

The maximum and minimum values which delineate the most frequent eighty percent of each distribution was not computed using the mean plus and minus some standard deviation because some of the spreads were not always a 'Normal' distribution. The maximum and minimum was computed by first 'binning' the data with respect to each of the thirty-two descriptors mentioned earlier. Then, the bins for each descriptor were sorted based on the frequency, from most frequent to least frequent. As the program traverses down the bins, the maximum and minimum of the descriptor are stored. The traversal is stopped when the program has traversed through at least eighty percent of the data. Consequently, the stored maximum and minimum represent the values that delineate the top eighty percentage of the distribution. This method of finding maximum and minimum works well with single peak distributions, For distributions with two or more peaks, the spread covered by the maximum and minimum are over-estimated. In such case, the determination of distinct is under-estimated.

For a particular descriptor, if the maximum and minimum of cluster X overlap with those of cluster Y, then cluster X and cluster Y is considered to be overlapping. On the other hand, if the maximum and minimum of cluster X does not overlap with the maximum and minimum of cluster Y, then cluster X is considered to be distinct from cluster Y. This analysis shows that 737 out of a total of 741 combinations (99%) of clusters are distinct. Since the analysis was based on individual descriptors, those non-distinct clusters could be overlapping or distinct if the analysis was extended to include combinations of the descriptors. These common protein loop motifs we have identified can now be used in database searching strategies to identify molecules that match the shape of these motifs. This is described in more detail in section 5

3 The Clustering of Protein Contact Surfaces

3.1 Background

The protein contact surfaces are comprised of a continuos sequence of amino acid residues as well as discontinuous sequences of amino acid residues. In the previous two sections, we have clustered the continuous loops of protein binding sites. In this section, we describe the clustering of the side chains of protein contact surfaces.

3.2 Method

3.2.1 Definition of Residues in Protein-Protein Interfaces

At least four criteria have been used in the literature to define residues that are involved in protein-protein interfaces. Two residues in two different chains are considered to be in the protein-protein interface if (1) their $c_\alpha$ atoms are less than 9.0 Å apart or (2) any atoms in one residue is within 5 Å of any atom of the other residue or (3) the distance between any atom of one residue to any atom within the other residue is less than the sum of their corresponding van der Waals radii plus 0.5 Å and (4) the van der Waals energy between the residues is less than −0.5 kcal/mol. The results are quite uniform between the four criteria[54]. Criterion three is used here. Furthermore, when the number of residues in an interface is less than 10, the interface is rejected because there is a high probability that this protein-protein interaction is a result of crystal packing.

3.2.2 Non-Redundant Dataset

Tsai[54] have scanned 2814 PDB entries from the September 1994 release of the PDB database[31] and found 1629 two-chain interfaces. Out of the 1629 two-chain interfaces, Tsai et al[54] have extracted 351 non-redundant families through the usage of structural comparison algorithm, measure of similarity and clustering of the structures into families (http://protein3d.ncifcrf.gov/tsai/frame/dataset.html).

A c++ program, p-p_interface.cpp was written to extract the coordinates of the $c_\alpha$-$c_\beta$ vectors of the residues in the protein-protein interface. For Glycine residues, the coordinates of the $c_\beta$ atom was obtained by superimposing the n, $c_\alpha$ and c' atoms of an ideal alanine onto the n, $c_\alpha$ and c' atoms of the glycine. Non-Glycine residues without $c_\beta$ atom coordinates were not included in the dataset. The 350 non-redundant families gave rise to 700 protein chains that consist of up to 150 residues that form contact in a single chain. This results in a very large dataset. For example, to identify common motifs from groups of 3-residues (this is the smallest size we would consider from a mimetic perspective) there would be as many as $$700 \times \binom{150}{3} = 385910000$$

residue comparisons. Most clustering algorithms are too computationally expensive for such a large problem. Consequently, we have developed new approaches to tackle the clustering of protein contact surfaces.

3.2.3 Identification of Seeds for Clustering.

Identifying common structures in protein contact surfaces is a significant challenge. The first step in determining the matching frequency of a group of residues is to develop a method to compare them. The large size of the database excludes the root mean squared deviation (RMSD) algorithm which is computationally expensive. A simpler method commonly used in chemical and biological situations is distance geometry comparisons.

The simplicity of this distance geometry method allows for rapid geometrical comparisons. However, distance geometry comparisons do not return a value of how closely related two geometries are (like an RMSD value) but instead return a match if their distances are the same within a certain tolerance. The geometric relationship between two residues can be represented by four "bowtie" distances (FIG. 17). The tolerance, TOL, represents the maximum allowed difference accepted between these distances to record a match. So two groups of residues {A,B} and {COD} (FIG. 17) are matched within TOL if and only if $$|d(A_H,B_H)-d(C_H,D_H)| \leq TOL \text{ and}$$

$$|d(A_H,B_T)-d(C_H,D_T)| \leq TOL \text{ and}$$

$$|d(A_T,B_H)-d(C_T,D_H)| \leq TOL \text{ and}$$

$$|d(A_T,B_T)-d(C_T,D_T)| \leq TOL$$

where d(x,y) is the Euclidean distance between the points x and y in three dimensional space. Typically $TOL \in [0.2, 1.0]$ Å.

The extension to groups of more than 2 residues is simple. The general rule is that a bowtie must be formed between each two-residue combination within the group. A group of size N contains exactly $\binom{N}{2}$ bowties. To check to see if two groups of N residues are matched, every possible rotation ($\binom{N}{2}$ in all) of the groups (or every bowtie-bowtie comparison) can be considered. For example, two groups of 3 residues {A,B,C} and {D,E,F} contain 6 possible residue matchups $$\{A,B,C\} \leftrightarrow \{D,E,F\}$$

$$\{A,B,C\} \leftrightarrow \{D,F,E\}$$

$$\{A,B,C\} \leftrightarrow \{E,D,F\}$$

$$\{A,B,C\} \leftrightarrow \{E,F,D\}$$

$$\{A,B,C\} \leftrightarrow \{F,D,E\}$$

$$\{A,B,C\} \leftrightarrow \{F,E,D\}$$

So these two 3-motifs are matched if $$(\{A,B\} \leftrightarrow \{D,E\} \text{ and} \{A,C\} \leftrightarrow \{D,F\} \text{ and}$$
$$\{B,C\} \leftrightarrow \{E,F\}) \text{ or}$$

$$(\{A,B\} \leftrightarrow \{D,F\} \text{ and} \{A,C\} \leftrightarrow \{D,E\} \text{ and}$$
$$\{B,C\} \leftrightarrow \{F,E\}) \text{ or}$$

$$(\{A,B\} \leftrightarrow \{E,D\} \text{ and} \quad \{A,C\} \leftrightarrow \{E,F\} \text{ and}$$
$$\{B,C\} \leftrightarrow \{D,F\}) \text{ or}$$

$(\{A,B\} \leftrightarrow \{E,F\}$ and $\{A,C\} \leftrightarrow \{E,D\}$ and
$\{B,C\} \leftrightarrow \{F,D\})$ or $(\{A,B\} \leftrightarrow \{F,D\}$ and $\{A,C\} \leftrightarrow \{F,E\}$ and
$\{B,C\} \leftrightarrow \{D,E\})$ or $(\{A,B\} \leftrightarrow \{F,E\}$ and $\{A,C\} \leftrightarrow \{F,D\}$ and
$\{B,C\} \leftrightarrow \{E,D\})$ or where $\{A,B\} \leftrightarrow \{D,E\}$ denotes that motifs $\{A,B\}$ and $\{D,E\}$ are equal within tolerance.

3.2.4 Extracting Matching Frequency of Motifs

To extract the most common motifs from the dataset, each motif is compared against all others. The set of all motifs that match a particular motif, within a tolerance called family tolerance (TOL), is referred to as the family of that motif. The cardinality of that family is the matching frequency for that motif. The common motifs with high matching frequencies are those that make good candidates for seed points.

Pseudo-code for the generic algorithm for determining the matching frequency for each motif is given in FIG. 18. This algorithm generates all motifs and their bowtie distances and then exhaustively compares each against all in the data set.

Initially, 3-motifs were formed by simply considering every feasible combination of 3 residues within each chain. However, the set of feasible motifs excludes ones that contain any bowtie distance greater than 25 Å, as we are only interested in common surface patches of this size. Although a very large data set is produced, it is still manageable for this algorithm. The data set produced for 4-motifs formed this way is too large. Using information from 3-motifs the size of the data set for 4-motifs can be greatly reduced. Every 4-motif is formed by 4 3-motifs. For example, the group $\{A,B,C,D\}$ is formed by the 4 groups $\{A,B,C\}$, $\{A,B,D\}$, $\{A,C,D\}$ and $\{B,C,D\}$. If any of these motifs of 3 did not frequently occur in the database then there is no chance of the motif $\{A,B,C,D\}$ being a highly common motif either. This greatly reduces the size of the data set and is essential for the construction of higher order groups. The same method is used for higher order motifs.

3.2.5 Finding the Peak Matching Frequencies

Now that the number of matching frequency has been determined for each motif, the next step was to identify the motifs with 'peak' number of matching frequency. A motif is marked as a peak if all the other motif within the family of the motif have lower or equal matching frequency. The algorithm for searching for peaks in the data set is given in FIG. 19. Initially the algorithm tags every motif as a peak. Subsequently, for every motif, A, in the data set, if any motif within the family of the motif A have a lower matching frequency, it is tagged as non-peak.

3.2.6 Algorithms for Clustering Motifs

The objective of clustering methods, in this section, is to retrieve all related motifs about some peak motifs, with the proviso that not all motifs in the data set need be clustered.

The simplest method for clustering motifs is a reverse scan of the data set as for the original matching algorithm. This method passes through the data set once accepting into the cluster every motif that is matched. This procedure is very similar to the PAM non-hierarchical method[55]. This algorithm is called the one pass algorithm and is outlined in FIG. 20. The span of the one-pass algorithm for a landscape of motifs is illustrated in FIG. 21. There is also an assumption that all hills are symmetric about their peak motif. The tolerance, OTOL, assumes that the width of each hill is identical. The entire hill is rarely collected because the range of the tolerance is constant throughout the algorithm. There is a possibility that some motifs collected belong to a different hill.

An algorithm that in part overcomes these difficulties is the greedy algorithm (FIG. 22). This algorithm is very similar to the single linkage hierarchical method. Each cluster is initialised as a seed point. Motifs are added to each cluster if they match any motif within the current cluster within tolerance. The algorithm moves down each peak until no other motifs in the data set match any motif within the cluster. This span is illustrated in FIG. 23. A flaw of the greedy algorithm is that it continues to collect motifs until no others exist that match those in the cluster (within GTOL). There is a danger of collecting motifs that belong to another peak (if GTOL is too large) or not collecting enough (if GTOL is too small). There is also no guarantee that the distribution of motifs down each hill is consistent or even. There is also a possibility that the algorithm may not halt until every motif in the database is collected if GTOL is overly large.

A simple method of overcoming this problem is to apply an additional tolerance to the greedy algorithm. The combined one pass and greedy algorithm applies a one-pass tolerance, OTOL, to the greedy algorithm to limit its span. It applies the additional constraint that every motif in each cluster has to be within OTOL of the seed motif. This algorithm is outlined in FIG. 24.

A tolerance, 'sealevel', with respect to the matching frequency (rather than its geometry) of a motif is also effective in restricting the span of the greedy algorithm. All motifs with matching frequency below the sea level are discarded from the data set. FIG. 25 shows how a sea level is applied to the single linkage algorithm. An illustration of the possible span of the algorithm is given in FIG. 26. However, selecting the correct sealevel is not always easy. If set too low it will have little effect in restricting the span of the algorithm. If set too high some peaks (and hills) will be excluded from the data set altogether. As an illustration, the first peak from the left in FIG. 26 has been totally excluded from the data set and the third peak has been restricted more so than the second. Unless all peaks are about the same height the application of a sea level will handicap some hills more than others.

To overcome this problem the sea level for each peak can be set adaptively as shown in FIG. 27. This is a more appropriate method for restricting the span of the algorithm. Each sea level can be scaled according to the frequency of the peak motif.

All methods discussed in this section can be altered for superimposition of motifs onto the seed motif. FIG. 28 shows how this adjustment is made to the PAM method. Although this new tolerance minimised the RMSD value for each cluster, it has no physical significance in terms of collecting the peak for each seed. These algorithms are slightly more expensive than their distance geometry counterparts.

3.2.7 Secondary Structure Analysis

The analysis of the secondary structure of each residue in the motifs was conducted using the DSSP (Dictionary of Protein Secondary Structure) software[4]. This software has been utilized widely throughout the literature for the classification of protein shapes into formal secondary structure. Given the 3D coordinates of residues within a protein, DSSP classifies the shape based on its refined expert system. There are 8 different secondary structure classifications considered by DS SP. They are described in Table 14 together with the abbreviations that will be adopted in this paper. The classification 'no assignment' refers to shapes that do not fit any of the other classifications defined.

3.3 Clustering Results
3.3.1 Determining the Seed Points

The first step to determine the seed points for clustering was to calculate the matching frequency of each 3-motif in the dataset. This was the highest order of motif that was computationally feasible. An exhaustive combination of 3-motifs produced 9,215,424 motifs as opposed to 197,712,949 4-motifs.

Three family tolerances (TOL) of 0.25, 0.5 and 0.75 Å were chosen based on a number of sample calculations. 0.25 Å was the lowest tolerance that produced meaningful generalisations about structure in the dataset while 0.75 Å was the highest tolerance that was computationally feasible, especially as the number of residues to be clustered increased.

Following the calculation of the matching frequencies for 3-motifs for all three TOL, the 4-motifs were constructed. As discussed previously in the method section, these motifs were constructed based on the common 3-motifs. At this point, we eliminated the uncommon motifs by removing all motifs that have a matching frequency below the matching frequency sealevel. For example, all 3-motifs with less than 30 matching frequency were excluded before 4-motifs were created. This level was selected based on trends seen in the dataset A matching frequency sealevel of 30 is insignificant when compared against the highest matching frequency (434 for TOL 0.25 Å). We also tested a matching frequency sea levels of 20 when forming 4-motifs from the 3-motifs, and found that lowering the matching frequency sealevel had no effect on the frequency of the seed points. Given the sealevels of 30 for 3-motif, 5 for 4-motif, 0 for higher order motifs, the highest matching frequency for each tolerance for each N-motif ($3 \leq N \leq 7$) is given in FIG. 30. FIG. 29 shows the number of N-motifs created. The number of motifs for larger tolerances is greater because the matching frequencies are higher and hence less of the dataset is excluded.

Following the calculation of the matching frequency for all motifs within the dataset, peak motif geometries can be extracted from the dataset (FIG. 19). From the dataset of peak motifs, the 30 motifs with the largest matching frequency were selected to be the seed points for the clustering stage. This value is kept constant for all motif sizes and tolerances. Although chosen arbitrarily, it almost always includes all unique motifs that have up to half the matching frequency of the highest value for that dataset. At the same time, there are not too many seed points as to get significant overlapping in the clusters. When only 30 seed points are selected, this overlapping only occurs when large tolerances are adopted for the clustering algorithms. In addition, a plot of a histogram of the dataset reveals that significant amount of the original data is covered by the 30 most common unique motifs.

3.3.2 The Clusters

After the determination of the seed motifs, two clustering methods were finally adopted: (1) one-pass algorithm (FIG. 20) using the same tolerance as the initial family tolerance, and with no sealevel applied. (2) Greedy algorithm with adaptive sealevel proportional to the peak (or seed) matching frequency (FIG. 27). A number of different greedy tolerances (GTOL) were applied in an attempt to achieve as large a range as possible for the tightness of the clusters. Different adaptive sealevels of 0.125, 0.25, 0.5 and 0.75 of the frequency of the seed was trailed during clustering.

The success of each clustering algorithm is determined by three pieces of information: the size of the clusters, the intracluster RMSD and the intercluster RMSD. The aim is to cluster as many motifs as possible, though the resulting clusters should contain motifs that are similar (minimise intracluster RMSD), though each cluster must differ as much as possible (increase intercluster RMSD).

Summary table for the 4-motif, 5-motif, 6-motif and 7-motif are given is given in the Table 6, 8, 10 and 12, respectively. The three different family tolerances considered, 0.25, 0.5 and 0.7, are given in the second column of each summary table. Information about the clustering for family tolerance 0.25 Å are not presented for 6-motifs or larger because the dataset was too small to extract meaningful clusters. The summary tables give the sum of the size of the clusters and the sum of the number of unique motifs within those clusters. The difference between the sum of the size of the clusters and the sum of the unique motifs in clusters give the number of motifs that occur in more than one cluster. The intracluster and intercluster RMSD are the average for each algorithm.

Table 7, 9, 11 and 13 contain the intracluster RMSD, the average RMSD of each motif in the cluster superimposed onto the average motif for that cluster (along the main diagonal), and the intercluster RMSD, the average RMSD of all motifs against the mean motif of other cluster (entries off the main diagonal). At the top of tables, the size of each cluster is presented.

The representative clusters for each N-motif is selected based on a simple criteria: select the clustering technique producing the largest amount of data, while having small intracluster RMSD and large intercluster RMSD. A small intracluster RMSD is less than 0.5 Å and a large intercluster RMSD is greater than 2.0 Å. These values were determined based on a visualisation of the resulting clusters. In addition these clusters should be relatively distinct, that is, not too many motifs occurring in more that one cluster.

The summary of results for the clustering of 4-motifs is given in Table 6. The parameters producing the largest set of clusters were the greedy method, family tolerance 0.75 Å, algorithm tolerance 0.5 Å and sealevel 0.125 of the seed matching frequency. However the average intracluster RMSD of 0.67 Å for this method is far too high. The next largest span of the dataset was achieved by the same method with sealevel 0.25 of the seed matching frequency. This method produced clusters with average intracluster RMSD of 0.51 which is much more acceptable. So the clusters produced by this method were selected as representative of the dataset for 4-motifs. The specific information about the selected 4-motif clusters is given in Table 7. The RMSD values on the main diagonal are much smaller than other values in the table. As described previously in Section 2.2.3, we anticipate using the filtered-centroid sorting algorithm to further refine the clusters identified. A picture of one of these clusters (C29) is shown in FIG. 31.

The summary of results for 5-motifs is given in Table 8. The selected representative clusters in this case were the greedy algorithm, family tolerance 0.75, greedy tolerance 0.7 Å and sealevel 0.125 of the seed matching frequency. The specific information about the selected clusters for 5-residue motifs in given in Table 9. An example of a cluster of 5-residue motifs (C30) is given in FIG. 32.

Average clustering results for 6-motifs are presented in Table 10. The selected method in this case was the greedy algorithm, family tolerance 0.75 Å, greedy tolerance 0.7 Å and sealevel 0.125 times the peak matching frequency. Specific cluster information about the methods are presented in Table 11. A representative cluster for the selected clustering algorithm C1 is given in FIG. 33.

The summary of results for 7-motifs is given in Table 12. The selected representative clusters in this case are the greedy algorithm, family tolerance 0.75 Å, greedy tolerance 0.9 Å and sealevel 0.125 of the seed matching frequency. Information about the specific clusters is presented in Table 13. An example of a visualised cluster of 7-motifs (C10) is given in FIG. 34.

3.3.3 Secondary Structure of the Clusters

An analysis of the secondary structure of the seed of each cluster was undertaken as described in the method section. The results show that all the residues of each seed were classified as α-helix except for the seed of cluster C2 of the 4-motifs where the four residues were classified as extended β-strand. There was a possibility, however, that this secondary structure classification of the seeds may not agree with the classification of the average motif of each cluster. Table 15, Table 16, Table 17 and Table 18 give the distribution of secondary structure throughout each of the 4, 5, 6, and 7-residue motif cluster, respectively. The results in these tables confirm that the secondary structures of the seeds are almost always consistent with the secondary structures of the motifs within the cluster. The only possible exception to this is cluster C2 for the 4-motifs, where only 56% of motifs have shared secondary structure with the seed. Most of the others (all α-helical) have over 90% in agreement with the seed, for all sizes of motifs.

Even if all the residues in the seeds or clusters are a-helical, the seeds or clusters do not necessarily belong to a single α-helix because the residues flanking between the residues in the motif may not be a-helical. Due to possible uncertainty with the DSSP classification, an α-helix is considered broken when flanked by two or more consecutive non a-helical residues. Table 19 records the proportion of motifs in each cluster that are not single α-helix. Except for cluster C2 of the 4-motifs (of which 99% are non-helical), almost all other motifs are single α-helix.

3.3.4 Non Single α-Helical Clusters

Given that almost all the above mentioned clusters are part of a single a-helix, we proceeded with extracting non-single α-helix clusters. The first step was to find the highest matching frequency seeds that were not single α-helix. The secondary structure of these seeds is given in Table 20. The results show that as the size of the motif increases, the secondary structure within each motif were more uniform.

Table 21 contains a summary of the clusters retrieved using a variety of methods with the new seeds. The most successful clustering methods of the previous analysis were adopted as starting points for this analysis. These results show that there is a strong trend towards clusters becoming more distinct as the size of the motif increases. For 4-residue motifs, there is significant sharing of motifs between clusters with many having quite a large intracluster RMSD. However, as the size of the motifs become larger, significantly larger tolerances can be adopted without altering the composition of the resulting clusters. The greedy tolerance could be extended to 1.1 Å for 6-residue motifs with the intracluster RMSD remaining very low. This is in contrast to the highest tolerance of 0.7 Å that could be adopted for the original set of seeds.

The criteria for the selection of representative clusters for each size of motif was the same as for the previous clustering study: to select the largest clusters possible, while keeping the intracluster RMSD low (less than approximately 0.5 Å) and the intercluster RMSD high (greater than 2.0 Å). RMSD comparisons between these resulting clusters for 4-residue motifs, is presented in Table 22.

Table 23 presents the distribution of different types of secondary structures for the new 4-residue motif clusters. Even though the seeds of each of these clusters are classified as 'not a single α-helix', a large proportion of motifs within three clusters are α-helix. Table 24 presents the proportion of motifs in each of the new clusters that are not a single α-helix. Less than 20% of motifs of cluster C5, C17 and C25 are not a single α-helix and more than 90% of residues of these clusters are classified as α-helix. Clusters that have a high proportion of motifs with no assignment to formal secondary structure, such as C2, C3, C4, C7, C10, C12 and C16 have relatively small size (the largest has just 26 members) and relatively low intracluster RMSD. Within this group, the average intracluster RMSD is 0.28 Å as opposed to the average intracluster RMSD of 0.52 Å for the entire set.

This relationship remains consistent for larger sizes of motifs too. Table 25 presents the distribution of secondary structure classifications for 7-residue motifs. Only clusters C1, C2 and C3 have motifs whose component residues are not entirely classified 'no assignment'. These three clusters have average intracluster RMSD of 0.41 Å which is much larger than the average intracluster RMSD for the entire set of 0.26 Å. This correlation suggests these clusters that contain motifs with no formal secondary structure assignment, have shape that is highly unique to any other motifs in the dataset.

4 Clustering of Surface Patches

The basic algorithm for the clustering of surface patches is similar to that for clustering discontinuous protein surfaces. Firstly, snapshots of the protein surface, called patch motifs, is generated. A patch motif containing N grid points is referred to as an N-patch. The smallest patch size that will be considered in this study is the 3-patch. The algorithm for the construction of 3-patches is given in FIG. 36.

FIG. 35 describe the algorithm for determining the matching frequency of each patch motif. Again, an RMSD superimposition of these motifs is too computationally expensive because of the size and the number of patches. A distance matrix is constructed so that the shape of the patches can be easily compared. This distance matrix is calculated for an N-patch by creating a complete graph $K_N$ whose vertices are the grid points and edges are weighted by the Euclidian distance between each pair of vertices. An illustration of a complete graph $K_9$ constructed for a 9-patch is given in FIG. 38.

A total of N! comparisons are required to determine if two N-patches are equal in shape. Every vertex-vertex match-up needs to be considered. This is a very expensive calculation computationally. If N=4, for example, 24 orientations with 144 edge distance comparisons, need to be attempted in order to determine if two patches do not have matching geometric structure. If N=9, the number of orientations becomes 362880 with 13 063 680 distance comparisons! A number of improvements need to be made to make this problem feasible, A number of quick and simple comparisons can be made between pairs of patches before an exhaustive check should take place. This is to improve the computational feasibility of the problem. The first is to compare the charges of each grid point before comparing distances. If the charges don't match within the charge tolerance, there is no need to check if the edge distances match. This is a much easier calculation. Another is to check if the longest and shortest edge distances of the pair of patches match. If they don't then the geometric structure of the patches is different. Finally, there may be some distances of the distance matrix that remain constant for all patches because of the way the grid was originally constructed. This may remove the need to consider certain orientations of patches when being compared.

The N+1-patches will be constructed based on N-patches in similar manner to the higher order motif build-up procedure for the discontinuous surfaces described earlier. Patches that are less than a defined matching frequency sealevel will be removed from the dataset. This reduces the number of redundant higher order patches that will be created. The algorithm for the creation of higher order patches is given in FIG. 37. In this algorithm, each new N-patch is created from (N−1) (N−1)-patches.

Once the matching frequency is determined, seeds and clusters can be obtained as described in the previous sections.

5 Scaffolds

As described above, the present inventors have clustered the side chain positions of β-turns, loops and protein contact surfaces. This has resulted in the identification of 9, 39 and 240 highly populated motifs for β-turns, loops and protein contact surfaces, respectively. As an example, the coordinate of the $5^{th}$ least popular cluster of all these motifs are given in Table 26. These motifs define common spatial elements of protein surfaces. Our objective is to use these motifs to design libraries of molecules. Consequently, these motifs are used as biological descriptors in library design, and the resulting libraries will mimic common protein shapes. In high throughput screening, such libraries will be a valuable resource for the development of new lead compounds.

Figure 39A:
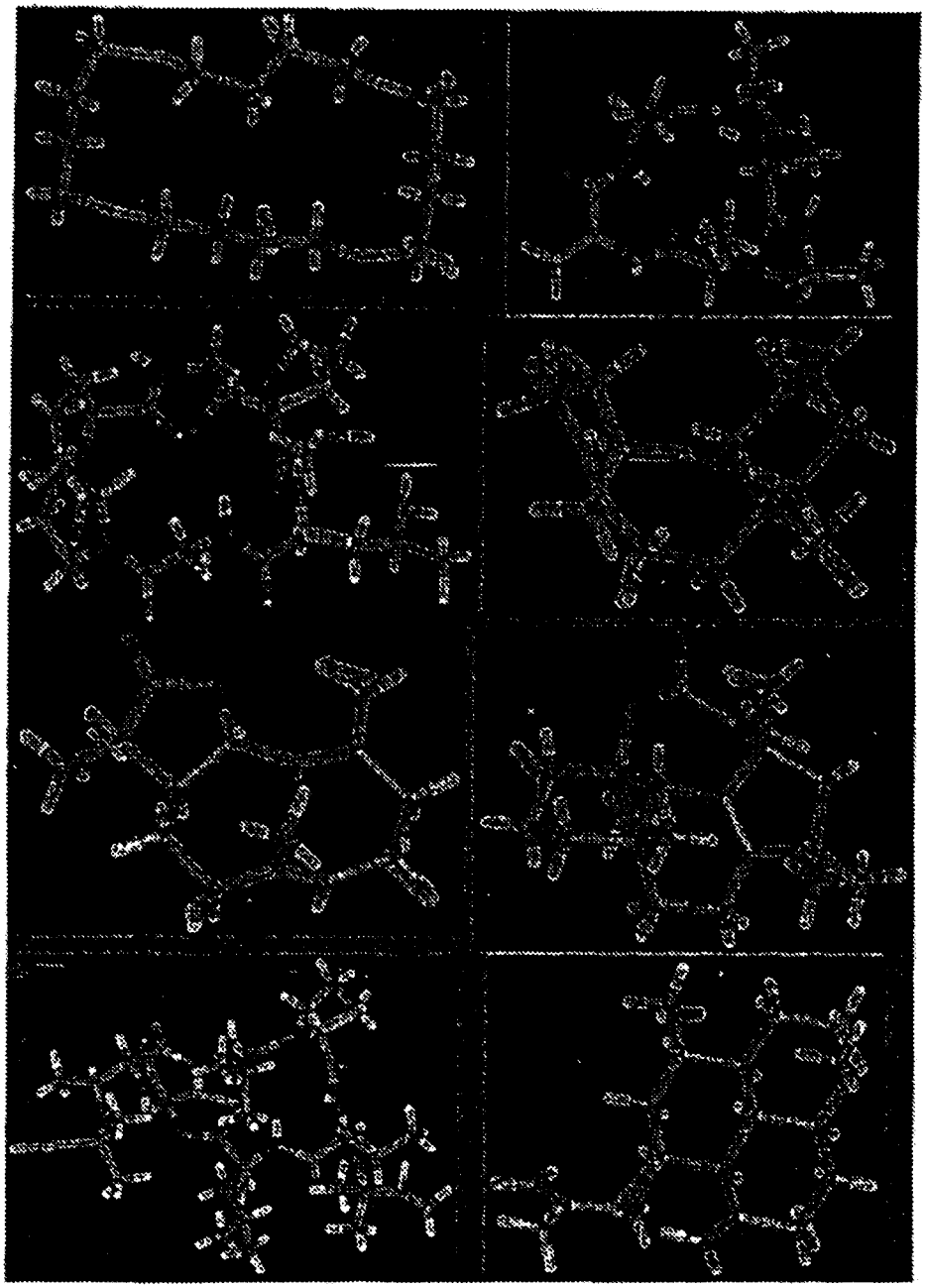
Figure 39B:
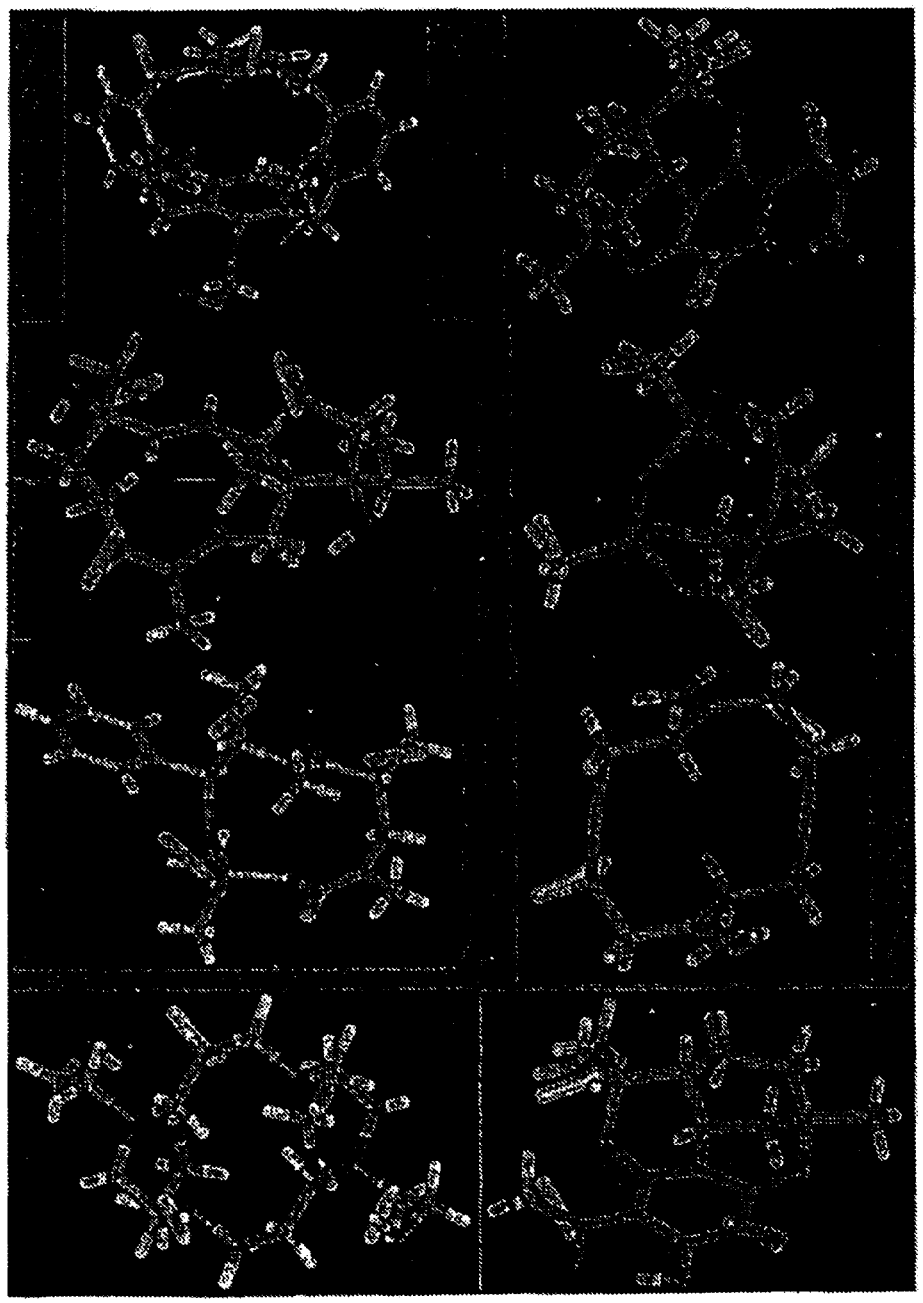
Figure 39C:
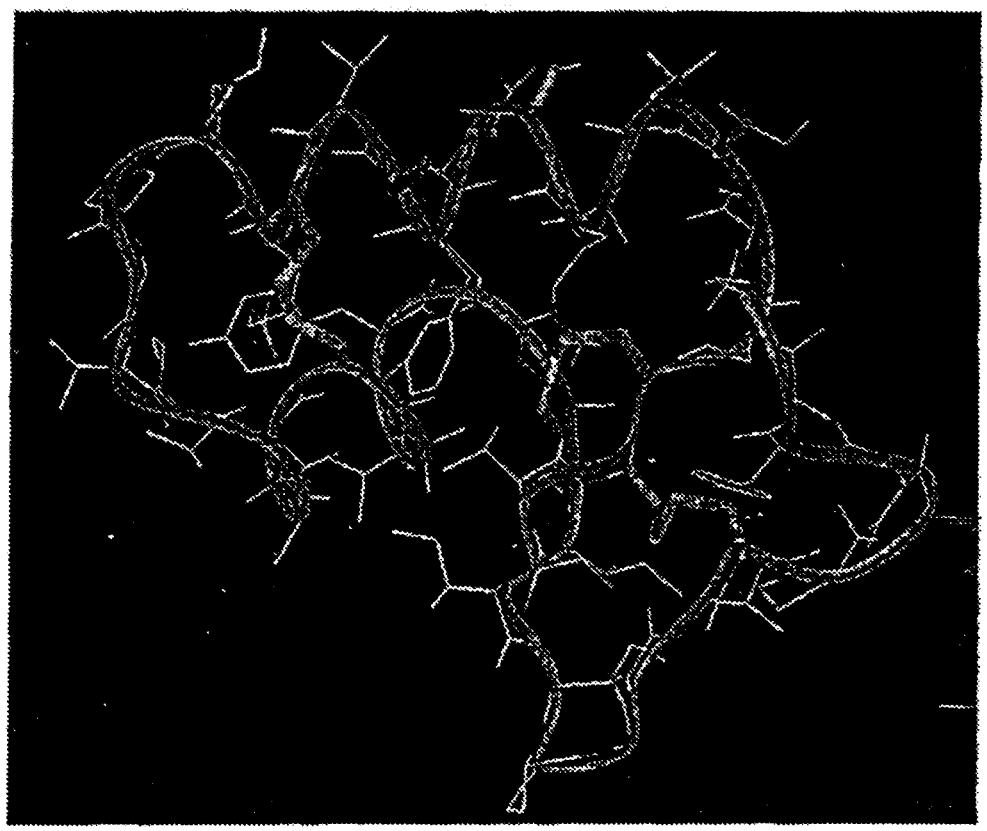

To this end, the present inventors have used a subset of the motifs and have screened the virtual library of molecules derived from the Cambridge Structural Database to identify molecules that match the spatial elements of the motifs. Our in house virtual-screening of virtual-library program, VECTRIX, was used to search the database. FIG. 39a shows some of the scaffolds that match the β-turn conformations, FIG. 39b shows some of the scaffolds that match the common loop conformations, and FIG. 39c shows a scaffold that match a common six-residues protein-protein interaction surface.

As illustrated in FIG. 39, molecules are identified that match the shape of the common motifs. This information will lead to the design of molecules that match common protein shapes.

Throughout this specification, the aim has been to describe the preferred embodiments of the invention without limiting the invention to any one embodiment or specific collection of features. Various changes and modifications may be made to the embodiments described and illustrated herein without departing from the broad spirit and scope of the invention.

All computer programs, algorithms, patent and scientific literature referred to in this specification are incorporated herein by reference in their entirety.

REFERENCES

1) Rose, G. D.; Young, W. B. *Nature* 1983, 304, 654-657.
2) Rose, G. D.; Gierasch, L. M.; Smith, J. A. *Adv. Protein. Chem.* 1985, 37, 1-109.
3) Wilmot, C. M.; Thornton, J. M. *Protein engineering* 1990, 3(6), 479-493.
4) Kabsch, W.; Sander, C. *Biopolymers* 1983, 22, 2577-2637.
5) Richardson, J. S. *Adv. Protein. Chem.* 1981, 34, 167-339.
6) Wilmot, C. M.; Thornton, J. M. *J. Mol. Biol.* 1988, 203, 221-232.
7) Freidinger, R. M.; Veber, D. F.; Perlow, D. S.; Brooks, J. R. *Science* 1980, 210, 656-658.
8) Li, S. Z.; Lee, J. H.; Lee, W.; Yoon, C. J.; Baik, J. H.; Lim. S. K. *Eur. J. Biochem.* 1999, 265, 430-440.
9) Andrianov, A. M. *Molecular Biology* 1999, 33, 534-538.
10) Smith, J. A.; Pease, L. G. *CRC Crit. Rev. Biochem.* 1980, 8, 315-399.
11) Mutter, M. *TIBS* 1988, 13, 260-265.
12) Ball, J. B.; Alewood, P. F. *Journal of Molecular Recognition* 1990, 3, 55-56.
13) Tran, T. T.; Treutlein, H. R.; Burgess, A. W. *J. Comput. Chem.* 2001, 22, 1010-1025.
14) Douglas, A. J.; Mulholland, G.; Walker, B.; Guthrie, D. J. S.; Elmore, D. T.; Murphy, R. F. *Biochem. Soc. Trans.* 1988, 16, 175-176.
15) Li, W.; Burgess, K. *Tetrahedron Lett.* 1999, 40, 6527-6530.
16) Halab, L.; Lubell, W. D. *Journal of organic chemistry* 1999, 64, 3312-3321.
17) Terrett, N. *Drug Discovery Today* 1999, 4, 141-141.
18) Rosenquist, S.; Souers, A. J.; Virgilio, A. A.; Schurer, S. S.; Ellman, J. A. *Abstracts of papers of the American chemical society* 1999 1999, 217, 212
19) Gardner, R. R.; Liang, G. B.; Gellman, S. H. *J. Am. Chem. Soc.* 1999, 121, 1806-1816.
20) Mer, G.; Kellenberger, E.; Lefevre, J. F. *J. Mol. Biol.* 1998, 281, 235-240.
21) Lombardi, A.; D'Auria, G.; Maglio, O.; Nastri, F.; Quartara, L.; Pedone, C.; Pavone, V. *J. Am. Chem. Soc.* 1998, 120, 5879-5886.,
22) Fink, B. E.; Kym, P. R.; Katzenellenbogen, J. A. *J. Am. Chem. Soc.* 1998, 120, 4334-4344.
23) Venkatachalam, C. M. *Biopolymers* 1968, 6, 1425-1436.
24) Lewis, P. N.; Momany, F. A.; Scheraga, H. A. *Biochim Biophys Acta* 1973, 303, 211-229.
25) Hutchinson, E. G.; Thornton, J. M. *Protein Science* 1994, 3, 22-7-2216.
26) Ball, J. B.; Hughes, R. A.; Alewood, P. F.; Andrews, P. R. *Tetrahedron* 1993, 49, 3467-3478.
27) Ball, J. B.; Andrews, P. R.; Alewood, P. F.; Hughes, R. A. *Federation of European Biochemical Societies* 1990, 273, 15-16.
28) Garland, S. L.; Dean, P. M. *J. Comput.-Aided Mol. Design* 1999, 13, 469-483.
29) Garland, S. L.; Dean, P. M. *J. Comput.-Aided Mol. Design* 1999, 13, 485-498.
30) Ho, C. M.; Marshall, G. R. *J. Comput.-Aided Mol. Design* 1993, 185, 3-22.
31) Berstein, F. C.; Koetzle, T. F.; Williams, G. J. B.; Edgar, F.; Meyer, J.; Brice, M. D.; Kennard, O.; Shimanouchi, T.; Tasumi, M. *J. Mol. Biol.* 1977, 112, 535-542.
32) Jakes, S. E.; Willett, P. *Journal of Molecular Graphics* 1986, 4, 12
33) Wong, M. A.; Lane, T. *J. R. Statist. Soc. B* 1983, 45, 362-368.
34) Wong, A.; Lane, T. *J. R. Statist. Soc. B* 1983, 45, 362-368.
35) Tsai, C.-J.; Lin, S. L.; Wolfson, Hi.; Nussinov, R. *Protein Science* 1997, 6, 53-64.
36) AnonymousSAS/STAT User's guide, Volume 1, *ANOVA-FREQ, Version 6*; 1999;

37) Anderberg, M. R. *Cluster analysis for applications*; Academic Press: New York and London, 1973;

38) Forgy, E. W. *Biometrics* 1965, 21, 768

39) MacQueen, J. B. *Proc. Symp. Math. Statist. and Probability* 1967, 1, 281-297.

40) Joseph, D.; Petsko, G. A.; Karplus, M. *Science* 1990, 249, 1425-1428.

41) Jones, S.; van Heyningen, P.; Berman, H. M.; Thornton, J. M. *J. Mol. Biol.* 1999, 287, 877-896.

42) Wu, S. J.; Dean, D. H. *J. Mol. Biol.* 1996, 255, 628-640.

43) Wlodawer, A.; Miller, M.; Jakolski, M.; Sathyanarayana, B. K.; Baldwin, E.; Weber, I. T.; Selk, L. M.; Clawson, L.; Schneider, J.; Kent, S. B. H. *Science* 1989, 245, 616-621.

44) Lu, Y.; Valentine, J. S. *Curr. Opin. Struct. Biol.* 1997, 7, 495-500.

45) Bajorath, J.; Sheriff, S. *Proteins* 2001, 24, 152-157.

46) Kinoshita, K.; Sadanami, K.; Kidera, A.; Gō, N. *Protein engineering* 1999, 12, 11-14.

47) Perona, J. J.; Craik, C. S. *Protein Science* 1995, 4, 337-360.

48) Hobohm, U.; Scharf, M.; Schneider, R.; Sander, C. *Protein Science* 1992, 1, 409-417.

49) Hobohm, U.; Sander, C. *Protein Science* 1994, 3, 522

50) Frishman, D.; Argos, P. *Proteins: structure, function and genetics* 1995, 23, 566-579.

51) Damewood, J. R. In Lipkowitz, K. B., Boyd, D. B., Eds.; VCH Publishers: New York, 1996; pp 1-79.

52) Sokal, R. R.; Michener, C. D. *University of Kansas Science Bulletin* 1958, 38, 1409-1438.

53) Manly, B. F. J. *Multivariate statistical method, A primer*; Chapman & Hall: London, 1994;

54) Tsai, C.-J.; Lin, S. L.; Wolfson, H. J.; Nussinov, R. *J. Mol. Biol.* 1996, 260, 604-620.

55) Kaufman, L.; Rousseeuw, P. J., John Wiley and Sons Publisher: New York, 1990.

56) Lauri & Bartlett J. *Comp. Aid. Mol. Des.* 1994, 8 5

TABLE 1

| Cluster | 1 | 2 | 3 | 4 | 5 | 6 | 7 |
|---|---|---|---|---|---|---|---|
| 1 | 0.32 | 0.70 | 0.78 | 1.10 | 0.71 | 0.84 | 1.39 |
| 2 | 0.70 | 0.31 | 0.65 | 0.60 | 0.63 | 1.09 | 0.93 |
| 3 | 0.85 | 0.75 | 0.49 | 0.86 | 0.79 | 0.99 | 1.10 |
| 4 | 1.12 | 0.64 | 0.81 | 0.38 | 0.82 | 1.47 | 0.67 |
| 5 | 0.72 | 0.66 | 0.72 | 0.81 | 0.35 | 1.15 | 0.89 |
| 6 | 0.84 | 1.09 | 0.93 | 1.46 | 1.14 | 0.31 | 1.69 |
| 7 | 1.40 | 0.95 | 1.05 | 0.67 | 0.90 | 1.70 | 0.38 |

TABLE 2

| Cluster | 1 | 2 | 3 | 4 | 5 | 6 | 7 | 8 |
|---|---|---|---|---|---|---|---|---|
| 1 | 0.32 | 0.70 | 0.87 | 1.09 | 0.71 | 0.84 | 1.39 | 0.80 |
| 2 | 0.69 | 0.29 | 0.70 | 0.59 | 0.64 | 1.09 | 0.94 | 0.71 |
| 3 | 0.89 | 0.74 | 0.39 | 0.81 | 0.84 | 1.06 | 1.06 | 0.75 |
| 4 | 1.11 | 0.62 | 0.80 | 0.36 | 0.80 | 1.47 | 0.66 | 0.87 |
| 5 | 0.71 | 0.66 | 0.82 | 0.80 | 0.34 | 1.16 | 0.89 | 0.72 |
| 6 | 0.84 | 1.09 | 1.04 | 1.46 | 1.15 | 0.31 | 1.69 | 0.94 |
| 7 | 1.40 | 0.96 | 1.05 | 0.67 | 0.90 | 1.70 | 0.38 | 1.09 |
| 8 | 0.84 | 0.77 | 0.77 | 0.89 | 0.76 | 0.97 | 1.10 | 0.43 |

TABLE 3

| Cluster | 1 | 2 | 3 | 4 | 5 | 6 | 7 | 8 | 9 |
|---|---|---|---|---|---|---|---|---|---|
| 1 | 0.32 | 0.70 | 0.86 | 1.09 | 0.71 | 0.84 | 1.39 | 0.79 | 2.14 |
| 2 | 0.69 | 0.29 | 0.70 | 0.59 | 0.64 | 1.09 | 0.93 | 0.71 | 1.67 |
| 3 | 0.88 | 0.74 | 0.39 | 0.81 | 0.84 | 1.06 | 1.06 | 0.76 | 1.61 |
| 4 | 1.10 | 0.62 | 0.80 | 0.36 | 0.81 | 1.47 | 0.67 | 0.87 | 1.24 |
| 5 | 0.71 | 0.66 | 0.82 | 0.80 | 0.34 | 1.16 | 0.88 | 0.72 | 1.76 |
| 6 | 0.84 | 1.09 | 1.04 | 1.46 | 1.15 | 0.30 | 1.69 | 0.93 | 2.37 |
| 7 | 1.40 | 0.96 | 1.05 | 0.67 | 0.89 | 1.70 | 0.38 | 1.09 | 1.09 |
| 8 | 0.83 | 0.77 | 0.77 | 0.90 | 0.76 | 0.96 | 1.10 | 0.43 | 1.77 |
| 9 | 2.15 | 1.69 | 1.61 | 1.24 | 1.77 | 2.38 | 1.10 | 1.77 | 0.43 |

TABLE 4

| 0.3[1] | 0.4[2] | RMSD[3] | 0.3[1] | 0.5[2] | RMSD[3] | 0.3[1] | 0.6[2] | RMSD[3] | 0.3[1] | 0.7[2] | RMSD[3] |
|---|---|---|---|---|---|---|---|---|---|---|---|
| 4 | 1 | 0.11 | 4 | 1 | 0.15 | 2 | 1 | 0.39 | 9 | 1 | 0.51 |
| 2 | 2 | 0.42 | 2 | 2 | 0.34 | 4 | 2 | 0.26 | 4 | 2 | 0.22 |
| 5 | 3 | 0.15 | 5 | 3 | 0.17 | 16 | 3 | 0.21 | 16 | 3 | 0.21 |
| 3 | 4 | 0.30 | 12 | 4 | 0.64 | 12 | 4 | 0.64 | Aver | | 0.31 |
| 6 | 5 | 0.15 | 4 | 5 | 0.27 | 16 | 5 | 0.00 | | | |
| 12 | 6 | 0.64 | 3 | 6 | 0.30 | 37 | 6 | 0.57 | | | |
| 11 | 7 | 0.29 | 13 | 7 | 0.21 | Aver | | 0.34 | | | |
| 4 | 8 | 0.12 | 14 | 8 | 0.22 | | | | | | |
| 10 | 9 | 0.00 | 10 | 9 | 0.14 | | | | | | |
| 14 | 10 | 0.26 | 1 | 10 | 0.12 | | | | | | |
| 13 | 11 | 0.36 | 31 | 11 | 0.21 | | | | | | |
| 17 | 12 | 0.21 | 37 | 12 | 0.60 | | | | | | |
| 27 | 13 | 0.06 | 37 | 13 | 0.20 | | | | | | |
| 31 | 14 | 0.21 | 37 | 14 | 0.72 | | | | | | |
| 29 | 15 | 0.15 | 35 | 15 | 0.88 | | | | | | |
| 37 | 16 | 0.42 | Aver | | 0.34 | | | | | | |
| 37 | 17 | 0.45 | | | | | | | | | |
| 19 | 18 | 0.71 | | | | | | | | | |
| 19 | 19 | 0.80 | | | | | | | | | |
| 2 | 20 | 0.80 | | | | | | | | | |
| 16 | 21 | 0.78 | | | | | | | | | |
| Aver | | 0.35 | | | | | | | | | |

TABLE 5

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|---|---|---|---|---|---|---|---|---|---|---|---|---|---|---|---|---|---|---|---|
| 1 | 0.39 | 0.75 | 0.81 | 0.79 | 1.09 | 1.25 | 1.36 | 0.88 | 0.85 | 1.06 | 1.25 | 1.40 | 1.85 | 2.08 | 2.67 | 2.80 | 3.07 | 3.19 | 3.10 | 2.69 | 3.37 | 3.02 | 2.93 | 3.22 | 3.05 | 3.07 | 3.29 | 1.99 | 1.66 | 1.66 | 2.20 | 1.59 | 1.66 | 2.51 | 2.65 | 2.50 | 2.83 | 3.24 | 3.18 |
| 2 | | 0.49 | 0.80 | 0.82 | 0.95 | 0.90 | 1.18 | 0.84 | 1.02 | 1.00 | 0.93 | 0.97 | 1.45 | 1.85 | 2.31 | 2.48 | 2.73 | 2.91 | 2.77 | 2.34 | 3.06 | 2.79 | 2.71 | 2.97 | 3.09 | 3.01 | 3.14 | 1.84 | 1.65 | 1.39 | 2.14 | 1.46 | 1.74 | 2.57 | 2.65 | 2.43 | 2.78 | 3.10 | 3.12 |
| 3 | | | 0.42 | 0.75 | 0.88 | 1.02 | 0.83 | 1.26 | 1.32 | 1.23 | 1.36 | 1.18 | 1.61 | 1.48 | 2.21 | 2.32 | 2.73 | 2.79 | 2.70 | 2.27 | 3.07 | 2.58 | 2.59 | 2.87 | 3.22 | 3.03 | 3.12 | 2.23 | 1.95 | 1.76 | 2.54 | 1.92 | 2.09 | 2.88 | 2.88 | 2.78 | 3.09 | 3.20 | 3.38 |
| 4 | | | | 0.41 | 0.72 | 0.89 | 0.95 | 1.18 | 1.14 | 0.90 | 1.32 | 1.28 | 1.58 | 1.76 | 2.39 | 2.48 | 2.85 | 2.94 | 2.80 | 2.40 | 3.16 | 2.76 | 2.68 | 2.98 | 3.14 | 3.00 | 3.18 | 1.97 | 1.62 | 1.54 | 2.39 | 1.77 | 1.89 | 2.70 | 2.66 | 2.53 | 2.96 | 3.23 | 3.21 |
| 5 | | | | | 0.44 | 0.74 | 0.87 | 1.22 | 1.28 | 0.93 | 1.14 | 1.03 | 1.17 | 1.54 | 2.02 | 2.11 | 2.45 | 2.58 | 2.39 | 1.99 | 2.74 | 2.41 | 2.34 | 2.62 | 2.99 | 2.77 | 2.87 | 1.81 | 1.60 | 1.30 | 2.24 | 1.66 | 1.89 | 2.66 | 2.59 | 2.39 | 2.74 | 2.88 | 3.02 |
| 6 | | | | | | 0.47 | 1.01 | 1.22 | 1.33 | 0.88 | 1.07 | 0.96 | 0.96 | 1.63 | 1.93 | 2.09 | 2.36 | 2.53 | 2.27 | 1.83 | 2.61 | 2.39 | 2.27 | 2.57 | 2.92 | 2.70 | 2.76 | 1.67 | 1.52 | 1.11 | 2.20 | 1.59 | 1.86 | 2.58 | 2.49 | 2.28 | 2.73 | 2.84 | 2.93 |
| 7 | | | | | | | 0.52 | 1.70 | 1.76 | 1.46 | 1.57 | 1.16 | 1.44 | 1.05 | 1.81 | 1.89 | 2.38 | 2.40 | 2.33 | 1.95 | 2.78 | 2.21 | 2.28 | 2.49 | 3.01 | 2.85 | 2.83 | 2.38 | 2.15 | 1.84 | 2.77 | 2.20 | 2.43 | 3.14 | 2.99 | 2.93 | 3.10 | 2.91 | 3.27 |
| 8 | | | | | | | | 0.37 | 0.76 | 0.94 | 0.90 | 1.34 | 1.62 | 2.33 | 2.63 | 2.74 | 2.88 | 3.06 | 2.94 | 2.55 | 3.06 | 2.96 | 2.78 | 3.01 | 2.64 | 2.75 | 2.95 | 1.45 | 1.32 | 1.22 | 1.63 | 1.03 | 1.25 | 2.07 | 2.26 | 1.96 | 2.31 | 2.79 | 2.68 |
| 9 | | | | | | | | | 0.49 | 0.84 | 1.05 | 1.48 | 1.72 | 2.43 | 2.66 | 2.80 | 2.86 | 2.99 | 2.94 | 2.57 | 3.02 | 2.92 | 2.72 | 2.92 | 2.47 | 2.57 | 2.81 | 1.40 | 1.08 | 1.26 | 1.57 | 1.03 | 1.01 | 1.87 | 2.03 | 1.86 | 2.20 | 2.69 | 2.55 |
| 10 | | | | | | | | | | 0.50 | 1.06 | 1.34 | 1.34 | 2.16 | 2.39 | 2.50 | 2.71 | 2.83 | 2.63 | 2.22 | 2.83 | 2.69 | 2.45 | 2.76 | 2.58 | 2.51 | 2.75 | 1.27 | 0.96 | 0.96 | 1.77 | 1.22 | 1.30 | 2.06 | 2.02 | 1.83 | 2.38 | 2.83 | 2.57 |
| 11 | | | | | | | | | | | 0.45 | 0.82 | 1.11 | 2.08 | 2.11 | 2.32 | 2.34 | 2.64 | 2.46 | 2.11 | 2.65 | 2.67 | 2.54 | 2.73 | 2.75 | 2.77 | 2.87 | 1.33 | 1.39 | 0.91 | 1.55 | 0.91 | 1.39 | 2.18 | 2.32 | 1.92 | 2.16 | 2.55 | 2.59 |
| 12 | | | | | | | | | | | | 0.50 | 0.95 | 1.52 | 1.65 | 1.90 | 2.03 | 2.28 | 2.14 | 1.79 | 2.46 | 2.29 | 2.29 | 2.41 | 2.86 | 2.77 | 2.69 | 1.84 | 1.85 | 1.28 | 2.11 | 1.52 | 1.95 | 2.67 | 2.74 | 2.42 | 2.51 | 2.52 | 2.87 |
| 13 | | | | | | | | | | | | | 0.53 | 1.69 | 1.45 | 1.68 | 1.74 | 2.03 | 1.68 | 1.30 | 2.11 | 2.02 | 1.88 | 2.09 | 2.56 | 2.35 | 2.28 | 1.55 | 1.66 | 0.99 | 2.01 | 1.56 | 1.93 | 2.51 | 2.41 | 2.11 | 2.32 | 2.23 | 2.49 |
| 14 | | | | | | | | | | | | | | 0.56 | 1.32 | 1.31 | 1.90 | 1.78 | 1.86 | 1.62 | 1.86 | 1.54 | 1.80 | 1.89 | 2.43 | 2.36 | 2.29 | 2.84 | 2.70 | 2.33 | 3.00 | 2.67 | 2.93 | 2.96 | 2.86 | 3.18 | 2.84 | 2.42 | 2.84 |
| 15 | | | | | | | | | | | | | | | 0.43 | 0.81 | 0.79 | 0.88 | 0.89 | 0.86 | 1.34 | 1.10 | 1.20 | 1.17 | 1.74 | 1.67 | 1.42 | 2.57 | 2.61 | 2.16 | 2.42 | 2.50 | 2.71 | 2.24 | 2.22 | 2.50 | 1.93 | 1.41 | 1.90 |
| 16 | | | | | | | | | | | | | | | | 0.48 | 1.03 | 0.92 | 1.02 | 1.05 | 1.41 | 0.88 | 0.95 | 0.83 | 1.43 | 1.39 | 1.35 | 2.65 | 2.61 | 2.32 | 2.49 | 2.66 | 2.75 | 2.08 | 2.00 | 2.45 | 2.00 | 1.50 | 1.90 |
| 17 | | | | | | | | | | | | | | | | | 0.43 | 0.71 | 0.73 | 1.05 | 0.92 | 1.19 | 1.23 | 0.97 | 1.26 | 1.39 | 1.07 | 2.41 | 2.62 | 2.30 | 1.95 | 2.40 | 2.41 | 1.78 | 1.85 | 1.99 | 1.35 | 0.82 | 1.35 |
| 18 | | | | | | | | | | | | | | | | | | 0.44 | 0.80 | 1.17 | 1.09 | 0.87 | 1.06 | 0.77 | 1.03 | 1.20 | 0.87 | 2.53 | 2.58 | 2.60 | 2.02 | 2.61 | 2.41 | 1.61 | 1.66 | 1.96 | 1.45 | 0.92 | 1.38 |
| 19 | | | | | | | | | | | | | | | | | | | 0.44 | 0.76 | 0.78 | 1.04 | 0.95 | 0.95 | 1.33 | 1.22 | 0.90 | 2.50 | 2.58 | 2.29 | 2.25 | 2.65 | 2.64 | 1.89 | 1.78 | 2.08 | 1.62 | 1.07 | 1.36 |
| 20 | | | | | | | | | | | | | | | | | | | | 0.49 | 1.09 | 1.17 | 0.94 | 1.26 | 1.74 | 1.46 | 1.29 | 2.30 | 2.33 | 1.94 | 1.98 | 2.44 | 2.62 | 2.30 | 2.01 | 2.37 | 2.07 | 1.55 | 1.77 |
| 21 | | | | | | | | | | | | | | | | | | | | | 0.49 | 1.32 | 1.09 | 1.17 | 1.21 | 1.04 | 0.81 | 2.24 | 2.41 | 2.40 | 1.98 | 2.55 | 2.38 | 1.63 | 1.45 | 1.66 | 1.34 | 0.92 | 0.93 |
| 22 | | | | | | | | | | | | | | | | | | | | | | 0.41 | 0.84 | 0.86 | 1.23 | 1.10 | 1.05 | 2.66 | 2.52 | 2.61 | 2.37 | 2.83 | 2.58 | 1.81 | 1.65 | 2.15 | 1.89 | 1.44 | 1.66 |
| 23 | | | | | | | | | | | | | | | | | | | | | | | 0.51 | 0.86 | 1.25 | 0.86 | 0.98 | 2.39 | 2.24 | 2.33 | 2.45 | 2.67 | 2.46 | 1.81 | 1.46 | 2.03 | 1.94 | 1.48 | 1.53 |
| 24 | | | | | | | | | | | | | | | | | | | | | | | | 0.46 | 0.83 | 0.88 | 0.90 | 2.44 | 2.39 | 2.59 | 2.08 | 2.64 | 2.30 | 1.48 | 1.44 | 1.90 | 1.55 | 1.11 | 1.39 |
| 25 | | | | | | | | | | | | | | | | | | | | | | | | | 0.48 | 0.81 | 0.85 | 1.92 | 1.91 | 2.45 | 1.55 | 2.13 | 1.72 | 0.87 | 0.98 | 1.37 | 1.13 | 0.95 | 1.05 |
| 26 | | | | | | | | | | | | | | | | | | | | | | | | | | 0.47 | 0.78 | 1.99 | 1.91 | 2.40 | 1.90 | 2.36 | 1.96 | 1.21 | 0.88 | 1.48 | 1.49 | 1.25 | 1.08 |
| 27 | | | | | | | | | | | | | | | | | | | | | | | | | | | 0.49 | 2.11 | 2.17 | 2.55 | 1.83 | 2.44 | 2.13 | 1.30 | 1.14 | 1.50 | 1.27 | 0.89 | 0.90 |
| 28 | | | | | | | | | | | | | | | | | | | | | | | | | | | | 0.48 | 0.80 | 0.80 | 0.95 | 0.87 | 0.99 | 1.36 | 1.37 | 0.83 | 1.44 | 1.97 | 1.60 |
| 29 | | | | | | | | | | | | | | | | | | | | | | | | | | | | | 0.50 | 0.99 | 1.26 | 1.05 | 0.86 | 1.37 | 1.29 | 1.13 | 1.74 | 2.22 | 1.85 |
| 30 | | | | | | | | | | | | | | | | | | | | | | | | | | | | | | 0.47 | 1.36 | 0.93 | 1.27 | 1.90 | 1.88 | 1.44 | 1.93 | 2.39 | 2.18 |
| 31 | | | | | | | | | | | | | | | | | | | | | | | | | | | | | | | 0.46 | 0.87 | 0.89 | 1.01 | 1.39 | 0.89 | 0.89 | 1.43 | 1.36 |
| 32 | | | | | | | | | | | | | | | | | | | | | | | | | | | | | | | | 0.46 | 0.83 | 1.50 | 1.76 | 1.30 | 1.55 | 2.09 | 1.98 |
| 33 | | | | | | | | | | | | | | | | | | | | | | | | | | | | | | | | | 0.51 | 1.08 | 1.36 | 1.16 | 1.43 | 1.93 | 1.78 |
| 34 | | | | | | | | | | | | | | | | | | | | | | | | | | | | | | | | | | 0.52 | 0.85 | 0.97 | 0.95 | 1.22 | 1.11 |
| 35 | | | | | | | | | | | | | | | | | | | | | | | | | | | | | | | | | | | 0.51 | 0.94 | 1.28 | 1.42 | 1.02 |
| 36 | | | | | | | | | | | | | | | | | | | | | | | | | | | | | | | | | | | | 0.47 | 0.99 | 1.42 | 0.98 |
| 37 | | | | | | | | | | | | | | | | | | | | | | | | | | | | | | | | | | | | | 0.49 | 0.78 | 0.86 |
| 38 | | | | | | | | | | | | | | | | | | | | | | | | | | | | | | | | | | | | | | 0.46 | 0.86 |
| 39 | | | | | | | | | | | | | | | | | | | | | | | | | | | | | | | | | | | | | | | 0.52 |

TABLE 6

| Method | Family TOL (Å) | TOL (Å) | Sealevel (% peak) | $\Sigma_{i=1}^{30} |C_i|$ | Unique $\Sigma_{i=1}^{30} |C_i|$ | Avg. Intracluster RMSD | Avg. Intercluster RMSD |
|---|---|---|---|---|---|---|---|
| O | 0.25 | 0.25 | 0 | 744 | 699 | 0.16 | 2.10 |
| O | 0.5 | 0.5 | 0 | 4862 | 4862 | 0.21 | 2.26 |
| O | 0.75 | 0.75 | 0 | 8902 | 8899 | 0.27 | 2.37 |
| G | 0.25 | 0.2 | 0.125 | 2427 | 1748 | 0.16 | 2.10 |
| G | 0.25 | 0.2 | 0.25 | 1905 | 1407 | 0.16 | 2.10 |
| G | 0.25 | 0.2 | 0.5 | 812 | 626 | 0.16 | 2.10 |
| G | 0.25 | 0.2 | 0.75 | 223 | 166 | 0.23 | 2.11 |
| G | 0.25 | 0.3 | 0.125 | 3801 | 2687 | 0.18 | 2.11 |
| G | 0.25 | 0.3 | 0.25 | 2498 | 1825 | 0.17 | 2.11 |
| G | 0.25 | 0.3 | 0.5 | 954 | 709 | 0.16 | 2.10 |
| G | 0.25 | 0.3 | 0.75 | 281 | 217 | 0.22 | 2.10 |
| G | 0.25 | 0.5 | 0.125 | 3802 | 2688 | 0.18 | 2.11 |
| G | 0.25 | 0.5 | 0.25 | 2498 | 1825 | 0.17 | 2.11 |
| G | 0.25 | 0.5 | 0.5 | 956 | 711 | 0.16 | 2.10 |
| G | 0.25 | 0.5 | 0.75 | 295 | 225 | 0.21 | 2.10 |
| G | 0.5 | 0.2 | 0.125 | 2079 | 2079 | 0.19 | 2.26 |
| G | 0.5 | 0.2 | 0.25 | 2073 | 2073 | 0.19 | 2.26 |
| G | 0.5 | 0.2 | 0.5 | 1853 | 1853 | 0.18 | 2.26 |
| G | 0.5 | 0.2 | 0.75 | 1047 | 1047 | 0.17 | 2.26 |
| G | 0.5 | 0.3 | 0.125 | 7654 | 7654 | 0.23 | 2.26 |
| G | 0.5 | 0.3 | 0.25 | 6715 | 6715 | 0.22 | 2.26 |
| G | 0.5 | 0.3 | 0.5 | 4071 | 4071 | 0.19 | 2.26 |
| G | 0.5 | 0.3 | 0.75 | 1540 | 1540 | 0.16 | 2.26 |
| G | 0.5 | 0.5 | 0.125 | 10135 | 8991 | 0.29 | 2.26 |
| G | 0.5 | 0.5 | 0.25 | 7413 | 7013 | 0.26 | 2.26 |
| G | 0.5 | 0.5 | 0.5 | 4088 | 4088 | 0.19 | 2.26 |
| G | 0.5 | 0.5 | 0.75 | 1540 | 1540 | 0.16 | 0.26 |
| G | 0.75 | 0.2 | 0.125 | 1848 | 1848 | 0.21 | 2.37 |
| G | 0.75 | 0.2 | 0.25 | 1848 | 1848 | 0.21 | 2.37 |
| G | 0.75 | 0.2 | 0.5 | 1846 | 1846 | 0.21 | 2.37 |
| G | 0.75 | 0.2 | 0.75 | 1646 | 1646 | 0.21 | 2.37 |
| G | 0.75 | 0.3 | 0.125 | 8040 | 8040 | 0.25 | 2.37 |
| G | 0.75 | 0.3 | 0.25 | 7973 | 7973 | 0.25 | 2.37 |
| G | 0.75 | 0.3 | 0.5 | 7149 | 7149 | 0.24 | 2.37 |
| G | 0.75 | 0.3 | 0.75 | 4215 | 4215 | 0.21 | 2.37 |
| G | 0.75 | 0.5 | 0.125 | 33367 | 14969 | 0.07 | 2.32 |
| G | 0.75 | 0.5 | 0.25 | 19813 | 11479 | 0.51 | 2.34 |
| G | 0.75 | 0.5 | 0.5 | 9975 | 8506 | 0.31 | 2.37 |
| G | 0.75 | 0.5 | 0.75 | 4726 | 4598 | 0.23 | 2.38 |

TABLE 7

|  | Q1 | Q2 | Q3 | Q4 | Q5 | Q6 | Q7 | Q8 | Q9 | Q10 |
|---|---|---|---|---|---|---|---|---|---|---|
| Size of Cluster | 616 | 682 | 278 | 258 | 609 | 1809 | 255 | 261 | 300 | 274 |
| Q1 | 0.69 | 2.56 | 3.72 | 3.09 | 0.69 | 2.32 | 3.14 | 3.97 | 1.18 | 2.74 |
| Q2 | 2.58 | 0.01 | 1.83 | 1.78 | 2.58 | 2.54 | 1.79 | 2.23 | 2.78 | 1.99 |
| Q3 | 3.77 | 1.91 | 0.27 | 1.58 | 3.77 | 3.98 | 1.58 | 1.29 | 4.01 | 2.47 |
| Q4 | 3.00 | 1.71 | 1.59 | 0.24 | 3.06 | 3.16 | 1.05 | 1.47 | 3.42 | 1.78 |
| Q5 | 0.70 | 2.56 | 3.71 | 3.06 | 0.71 | 2.33 | 3.11 | 3.94 | 1.15 | 2.72 |
| Q6 | 2.31 | 2.45 | 3.97 | 3.24 | 2.31 | 1.13 | 3.23 | 4.11 | 2.31 | 2.80 |
| Q7 | 3.08 | 1.69 | 1.58 | 1.04 | 3.08 | 3.12 | 0.27 | 1.47 | 3.30 | 1.75 |
| Q8 | 3.97 | 2.26 | 1.30 | 1.51 | 3.97 | 4.11 | 1.49 | 0.22 | 4.23 | 2.33 |
| Q9 | 1.30 | 2.81 | 4.00 | 3.43 | 1.30 | 2.37 | 3.30 | 4.20 | 0.32 | 2.77 |
| Q10 | 2.69 | 1.88 | 2.45 | 1.77 | 2.69 | 2.64 | 1.73 | 2.26 | 2.77 | 0.25 |
| Q11 | 3.99 | 2.26 | 1.23 | 1.56 | 3.99 | 4.10 | 1.49 | 0.96 | 4.20 | 2.33 |
| Q12 | 2.45 | 1.75 | 2.33 | 1.74 | 2.45 | 2.61 | 1.65 | 3.29 | 2.80 | 1.07 |
| Q13 | 2.88 | 2.36 | 2.79 | 2.10 | 2.88 | 2.12 | 2.29 | 2.97 | 3.04 | 2.11 |
| Q14 | 2.38 | 2.58 | 4.07 | 3.06 | 2.38 | 1.10 | 2.98 | 4.14 | 2.43 | 2.77 |
| Q15 | 3.04 | 2.34 | 2.71 | 2.33 | 3.04 | 2.11 | 2.10 | 3.01 | 2.89 | 1.89 |
| Q16 | 3.26 | 2.56 | 3.25 | 2.80 | 3.26 | 2.52 | 2.76 | 3.57 | 3.41 | 2.19 |
| Q17 | 2.71 | 2.94 | 4.13 | 3.17 | 2.71 | 1.49 | 3.30 | 4.15 | 2.41 | 2.64 |
| Q18 | 2.50 | 1.14 | 1.80 | 1.39 | 2.50 | 2.83 | 1.29 | 2.12 | 2.76 | 1.97 |
| Q19 | 1.83 | 1.50 | 2.69 | 1.96 | 1.83 | 2.12 | 1.74 | 2.75 | 2.19 | 1.71 |
| Q20 | 2.03 | 1.52 | 2.66 | 1.72 | 2.03 | 2.18 | 2.01 | 2.78 | 1.91 | 1.59 |
| Q21 | 3.42 | 1.14 | 1.81 | 1.46 | 2.42 | 2.78 | 1.38 | 2.20 | 2.76 | 1.92 |
| Q22 | 2.19 | 2.47 | 3.98 | 3.07 | 2.19 | 1.09 | 3.01 | 4.23 | 2.34 | 2.78 |
| Q23 | 2.30 | 2.47 | 3.97 | 3.08 | 2.30 | 1.12 | 3.05 | 4.24 | 2.27 | 2.69 |
| Q24 | 2.83 | 1.75 | 2.58 | 1.85 | 2.83 | 2.52 | 1.95 | 2.34 | 2.78 | 1.06 |
| Q25 | 2.44 | 1.71 | 2.65 | 2.23 | 2.44 | 2.26 | 2.21 | 2.62 | 2.57 | 1.53 |
| Q26 | 3.88 | 2.17 | 1.09 | 1.42 | 3.88 | 3.94 | 1.48 | 1.26 | 4.16 | 2.11 |
| Q27 | 2.37 | 1.67 | 2.62 | 2.28 | 2.37 | 2.23 | 2.26 | 2.66 | 2.52 | 1.61 |
| Q28 | 2.14 | 1.66 | 2.80 | 2.42 | 2.14 | 2.09 | 2.30 | 2.88 | 2.13 | 1.47 |
| Q29 | 3.01 | 1.14 | 1.29 | 1.55 | 3.01 | 3.02 | 1.61 | 1.78 | 3.29 | 2.16 |

TABLE 7-continued

| | | | | | | | | | | |
|---|---|---|---|---|---|---|---|---|---|---|
| Q30 | 2.42 | 1.12 | 1.80 | 1.50 | 2.42 | 2.77 | 1.37 | 2.21 | 2.72 | 1.95 |

| | Q11 | Q12 | Q13 | Q14 | Q15 | Q16 | Q17 | Q18 | Q19 | Q20 |
|---|---|---|---|---|---|---|---|---|---|---|
| Size of Cluster | 266 | 423 | 303 | 1750 | 310 | 304 | 476 | 1262 | 345 | 340 |
| Q1 | 4.00 | 2.53 | 2.90 | 2.32 | 3.07 | 3.22 | 2.82 | 2.45 | 1.81 | 1.98 |
| Q2 | 2.23 | 1.78 | 2.34 | 2.54 | 2.33 | 2.53 | 2.98 | 1.11 | 1.45 | 1.47 |
| Q3 | 1.22 | 2.36 | 2.79 | 3.98 | 2.71 | 3.26 | 4.16 | 1.86 | 2.72 | 2.68 |
| Q4 | 1.56 | 1.84 | 2.11 | 3.16 | 2.33 | 2.81 | 3.21 | 1.49 | 1.97 | 1.73 |
| Q5 | 3.96 | 2.51 | 2.90 | 2.33 | 3.07 | 3.25 | 2.80 | 2.44 | 1.77 | 1.95 |
| Q6 | 4.14 | 2.74 | 2.28 | 1.11 | 2.19 | 2.58 | 1.52 | 2.76 | 2.12 | 2.14 |
| Q7 | 1.47 | 1.72 | 2.29 | 3.12 | 2.10 | 2.76 | 3.34 | 1.41 | 1.75 | 2.01 |
| Q8 | 0.96 | 2.36 | 2.98 | 4.12 | 3.02 | 3.61 | 4.19 | 2.19 | 2.76 | 2.84 |
| Q9 | 4.14 | 2.82 | 3.03 | 2.37 | 2.89 | 3.39 | 2.45 | 2.77 | 2.18 | 1.90 |
| Q10 | 2.28 | 1.18 | 2.12 | 2.64 | 1.89 | 2.20 | 2.66 | 1.98 | 1.72 | 1.59 |
| Q11 | 0.23 | 2.34 | 3.05 | 4.11 | 2.96 | 3.61 | 4.32 | 2.18 | 2.85 | 2.82 |
| Q12 | 2.27 | 0.56 | 1.89 | 2.61 | 2.11 | 2.17 | 2.76 | 1.83 | 1.36 | 1.60 |
| Q13 | 3.00 | 1.86 | 0.28 | 2.12 | 1.07 | 2.26 | 1.85 | 2.64 | 2.22 | 2.24 |
| Q14 | 4.11 | 2.67 | 1.92 | 1.11 | 1.89 | 2.61 | 1.30 | 2.85 | 1.96 | 2.09 |
| Q15 | 2.95 | 2.02 | 1.07 | 2.11 | 0.28 | 2.23 | 1.89 | 2.63 | 2.28 | 2.22 |
| Q16 | 3.58 | 2.22 | 2.28 | 2.52 | 2.24 | 0.29 | 2.72 | 2.88 | 2.56 | 2.59 |
| Q17 | 4.25 | 2.79 | 1.80 | 1.48 | 1.84 | 2.75 | 0.54 | 3.19 | 2.40 | 2.17 |
| Q18 | 2.12 | 1.74 | 2.71 | 2.83 | 2.70 | 2.87 | 3.30 | 0.87 | 1.43 | 1.44 |
| Q19 | 2.82 | 1.43 | 2.22 | 2.12 | 2.25 | 2.53 | 2.43 | 1.47 | 0.30 | 1.04 |
| Q20 | 2.81 | 1.66 | 2.22 | 2.18 | 2.21 | 2.58 | 2.22 | 1.46 | 1.05 | 0.28 |
| Q21 | 2.17 | 1.85 | 2.64 | 2.78 | 2.72 | 2.89 | 3.36 | 0.69 | 1.37 | 1.58 |
| Q22 | 4.20 | 2.61 | 2.21 | 1.08 | 2.21 | 2.32 | 1.71 | 2.72 | 1.96 | 2.12 |
| Q23 | 4.24 | 2.71 | 2.25 | 1.12 | 2.25 | 2.30 | 1.67 | 2.75 | 2.10 | 2.08 |
| Q24 | 2.41 | 1.51 | 1.94 | 2.53 | 1.77 | 2.39 | 2.49 | 2.06 | 1.79 | 1.56 |
| Q25 | 2.62 | 1.34 | 1.76 | 2.26 | 1.98 | 2.57 | 2.38 | 2.03 | 1.47 | 1.68 |
| Q26 | 1.21 | 2.16 | 2.99 | 3.94 | 3.02 | 2.97 | 4.20 | 1.93 | 2.80 | 2.73 |
| Q27 | 2.64 | 1.38 | 1.78 | 2.23 | 1.99 | 2.50 | 2.38 | 1.98 | 1.39 | 1.62 |
| Q28 | 3.02 | 1.61 | 2.00 | 2.09 | 1.90 | 2.28 | 2.25 | 1.96 | 1.21 | 1.35 |
| Q29 | 1.75 | 1.94 | 2.52 | 3.02 | 2.51 | 2.57 | 3.53 | 1.32 | 1.97 | 2.08 |
| Q30 | 2.17 | 1.85 | 2.62 | 2.77 | 2.69 | 2.89 | 3.34 | 0.68 | 1.40 | 1.57 |

| | Q21 | Q22 | Q23 | Q24 | Q25 | Q26 | Q27 | Q28 | Q29 | Q30 |
|---|---|---|---|---|---|---|---|---|---|---|
| Size of Cluster | 944 | 1667 | 1648 | 386 | 882 | 428 | 855 | 473 | 545 | 861 |
| Q1 | 2.41 | 2.31 | 2.31 | 2.84 | 2.37 | 3.86 | 2.37 | 2.12 | 2.96 | 2.40 |
| Q2 | 1.07 | 2.54 | 2.54 | 1.75 | 1.73 | 2.21 | 1.73 | 1.61 | 1.01 | 1.06 |
| Q3 | 1.86 | 3.98 | 3.99 | 2.59 | 2.67 | 1.08 | 2.67 | 2.82 | 1.29 | 1.86 |
| Q4 | 1.55 | 3.16 | 3.16 | 1.85 | 2.21 | 1.40 | 2.21 | 2.41 | 1.55 | 1.55 |
| Q5 | 2.39 | 2.32 | 2.32 | 2.81 | 2.33 | 3.84 | 2.33 | 2.08 | 2.96 | 2.39 |
| Q6 | 2.74 | 1.11 | 1.11 | 2.44 | 2.28 | 4.08 | 2.28 | 1.97 | 2.90 | 2.73 |
| Q7 | 1.44 | 3.12 | 3.12 | 1.99 | 2.15 | 1.45 | 2.15 | 2.30 | 1.61 | 1.44 |
| Q8 | 2.25 | 4.12 | 4.12 | 2.39 | 2.73 | 1.28 | 2.73 | 2.89 | 1.79 | 2.25 |
| Q9 | 2.73 | 2.36 | 2.36 | 2.76 | 2.53 | 4.14 | 2.53 | 2.12 | 3.27 | 2.73 |
| Q10 | 1.98 | 2.64 | 2.65 | 1.06 | 1.60 | 2.09 | 1.59 | 1.47 | 2.13 | 1.99 |
| Q11 | 2.23 | 4.11 | 4.11 | 2.46 | 2.66 | 1.21 | 2.66 | 3.07 | 1.76 | 2.23 |
| Q12 | 1.88 | 2.61 | 2.62 | 1.42 | 1.23 | 2.09 | 1.22 | 1.53 | 2.01 | 1.89 |
| Q13 | 2.63 | 2.13 | 2.13 | 1.93 | 1.82 | 2.97 | 1.82 | 2.00 | 2.50 | 2.63 |
| Q14 | 2.83 | 1.09 | 1.09 | 2.56 | 2.22 | 4.00 | 2.23 | 2.07 | 3.14 | 2.83 |
| Q15 | 2.61 | 2.11 | 2.11 | 1.74 | 2.01 | 2.90 | 2.01 | 1.89 | 2.50 | 2.61 |
| Q16 | 2.86 | 2.51 | 2.51 | 2.39 | 2.36 | 2.96 | 2.36 | 2.28 | 2.57 | 2.86 |
| Q17 | 3.17 | 1.48 | 1.49 | 2.45 | 2.40 | 4.18 | 2.40 | 2.20 | 3.51 | 3.17 |
| Q18 | 0.86 | 2.83 | 2.83 | 2.10 | 2.01 | 1.91 | 2.00 | 1.87 | 1.19 | 0.86 |
| Q19 | 1.46 | 2.11 | 2.11 | 1.76 | 1.47 | 2.75 | 1.47 | 1.20 | 1.96 | 1.46 |
| Q20 | 1.43 | 2.18 | 2.18 | 1.56 | 1.62 | 2.70 | 1.62 | 1.35 | 2.05 | 1.42 |
| Q21 | 0.60 | 2.78 | 2.78 | 2.16 | 2.01 | 1.89 | 2.01 | 1.99 | 1.25 | 0.56 |
| Q22 | 2.68 | 1.07 | 1.07 | 2.72 | 2.24 | 3.92 | 2.25 | 2.09 | 2.93 | 2.07 |
| Q23 | 2.71 | 1.11 | 1.11 | 2.66 | 2.34 | 3.93 | 2.34 | 1.97 | 2.89 | 2.71 |
| Q24 | 2.07 | 2.53 | 2.53 | 0.26 | 1.36 | 2.27 | 1.36 | 1.25 | 1.99 | 2.08 |
| Q25 | 2.02 | 2.27 | 2.27 | 1.20 | 0.71 | 2.72 | 0.68 | 1.17 | 1.94 | 2.02 |
| Q26 | 1.95 | 3.94 | 3.94 | 2.29 | 2.69 | 0.22 | 2.60 | 2.98 | 1.71 | 1.95 |
| Q27 | 1.98 | 2.24 | 2.24 | 1.27 | 0.68 | 2.79 | 0.70 | 1.12 | 1.89 | 1.98 |
| Q28 | 1.98 | 2.09 | 2.09 | 1.24 | 1.28 | 2.96 | 1.27 | 0.28 | 1.91 | 1.98 |
| Q29 | 1.34 | 3.02 | 3.02 | 1.99 | 1.99 | 1.70 | 1.99 | 1.91 | 0.28 | 1.33 |
| Q30 | 0.53 | 2.77 | 2.77 | 2.19 | 2.03 | 1.88 | 2.03 | 2.01 | 1.25 | 0.52 |

TABLE 8

| Method | Family TOL (Å) | TOL (Å) | Sealevel (% peak) | $\Sigma_{i=1}^{30} |C_i|$ | Unique $\Sigma_{i=1}^{30} |C_i|$ | Avg. Intracluster RMSD | Avg. Intercluster RMSD |
|---|---|---|---|---|---|---|---|
| O | 0.25 | 0.25 | 0 | 163 | 160 | 0.31 | 2.46 |
| O | 0.5 | 0.5 | 0 | 2033 | 2033 | 0.23 | 2.58 |
| O | 0.75 | 0.75 | 0 | 4698 | 4698 | 0.29 | 2.59 |
| G | 0.25 | 0.2 | 0.125 | 88 | 88 | 0.35 | 2.48 |
| G | 0.25 | 0.2 | 0.25 | 87 | 87 | 0.35 | 2.48 |
| G | 0.25 | 0.2 | 0.5 | 78 | 78 | 0.35 | 2.48 |
| G | 0.25 | 0.2 | 0.75 | 57 | 57 | 0.20 | 2.48 |
| G | 0.25 | 0.3 | 0.125 | 475 | 322 | 0.23 | 2.45 |
| G | 0.25 | 0.3 | 0.25 | 438 | 307 | 0.23 | 2.45 |
| G | 0.25 | 0.3 | 0.5 | 289 | 223 | 0.25 | 2.46 |
| G | 0.25 | 0.3 | 0.75 | 131 | 114 | 0.28 | 2.46 |
| G | 0.25 | 0.5 | 0.125 | 498 | 342 | 0.23 | 2.45 |
| G | 0.25 | 0.5 | 0.25 | 453 | 319 | 0.23 | 2.45 |
| G | 0.25 | 0.5 | 0.5 | 309 | 237 | 0.24 | 2.45 |
| G | 0.25 | 0.5 | 0.75 | 162 | 135 | 0.28 | 2.46 |
| G | 0.5 | 0.2 | 0.125 | 69 | 69 | 0.23 | 2.59 |
| G | 0.5 | 0.2 | 0.25 | 69 | 69 | 0.23 | 2.59 |
| G | 0.5 | 0.2 | 0.5 | 68 | 68 | 0.23 | 2.59 |
| G | 0.5 | 0.2 | 0.75 | 57 | 57 | 0.22 | 2.59 |
| G | 0.5 | 0.3 | 0.125 | 1970 | 1970 | 0.22 | 2.58 |
| G | 0.5 | 0.3 | 0.25 | 1846 | 1846 | 0.22 | 2.58 |
| G | 0.5 | 0.3 | 0.5 | 1252 | 1252 | 0.21 | 2.58 |
| G | 0.5 | 0.3 | 0.75 | 458 | 458 | 0.27 | 2.58 |
| G | 0.5 | 0.5 | 0.125 | 4258 | 4258 | 0.27 | 2.58 |
| G | 0.5 | 0.5 | 0.25 | 3016 | 3016 | 0.24 | 2.58 |
| G | 0.5 | 0.5 | 0.5 | 1506 | 1506 | 0.21 | 2.58 |
| G | 0.5 | 0.5 | 0.75 | 525 | 525 | 0.22 | 2.58 |
| G | 0.75 | 0.2 | 0.125 | 45 | 45 | 0.15 | 2.58 |
| G | 0.75 | 0.2 | 0.25 | 45 | 45 | 0.15 | 2.58 |
| G | 0.75 | 0.2 | 0.5 | 45 | 45 | 0.15 | 2.58 |
| G | 0.75 | 0.2 | 0.75 | 45 | 45 | 0.15 | 2.58 |
| G | 0.75 | 0.3 | 0.125 | 1864 | 1861 | 0.24 | 2.59 |
| G | 0.75 | 0.3 | 0.25 | 1863 | 1863 | 0.24 | 2.59 |
| G | 0.75 | 0.3 | 0.5 | 1806 | 1806 | 0.34 | 2.59 |
| G | 0.75 | 0.3 | 0.75 | 1205 | 1205 | 0.23 | 2.58 |
| G | 0.75 | 0.5 | 0.125 | 6092 | 5427 | 0.38 | 2.57 |
| G | 0.75 | 0.5 | 0.35 | 3660 | 3660 | 0.34 | 2.58 |
| G | 0.75 | 0.5 | 0.5 | 1607 | 1607 | 0.27 | 2.59 |
| G | 0.75 | 0.5 | 0.75 | 1349 | 1349 | 0.23 | 2.59 |
| G | 0.75 | 0.7 | 0.125 | 10467 | 7852 | 0.56 | 2.55 |
| G | 0.75 | 0.7 | 0.25 | 7799 | 6026 | 0.46 | 2.55 |
| G | 0.75 | 0.7 | 0.5 | 3690 | 3690 | 0.27 | 2.59 |
| G | 0.75 | 0.7 | 0.75 | 1607 | 1607 | 0.23 | 2.59 |

TABLE 9

| | Q1 | Q2 | Q3 | Q4 | Q5 | Q6 | Q7 | Q8 | Q9 | Q10 |
|---|---|---|---|---|---|---|---|---|---|---|
| Size of Cluster | 298 | 238 | 821 | 309 | 245 | 174 | 147 | 168 | 178 | 296 |
| Q1 | 0.69 | 2.02 | 2.04 | 1.47 | 2.67 | 1.96 | 3.14 | 2.08 | 2.18 | 2.71 |
| Q2 | 2.00 | 0.66 | 2.46 | 2.44 | 3.26 | 2.30 | 4.07 | 2.48 | 1.15 | 2.48 |
| Q3 | 1.94 | 2.43 | 0.99 | 1.75 | 2.41 | 2.43 | 3.03 | 2.25 | 2.25 | 2.65 |
| Q4 | 1.14 | 2.42 | 0.83 | 0.78 | 2.70 | 2.17 | 3.03 | 1.98 | 2.32 | 2.67 |
| Q5 | 2.75 | 3.37 | 2.44 | 2.80 | 0.57 | 3.60 | 4.29 | 3.71 | 3.42 | 2.82 |
| Q6 | 2.03 | 2.25 | 2.47 | 2.25 | 3.59 | 0.30 | 2.85 | 7.09 | 2.52 | 3.60 |
| Q7 | 3.20 | 4.06 | 3.01 | 3.11 | 4.32 | 2.86 | 0.26 | 2.84 | 4.15 | 4.93 |
| Q8 | 2.15 | 2.47 | 2.28 | 2.07 | 3.70 | 1.08 | 2.83 | 0.30 | 2.36 | 3.64 |
| Q9 | 2.27 | 1.27 | 2.31 | 2.39 | 3.36 | 2.53 | 4.16 | 2.36 | 0.34 | 2.44 |
| Q10 | 2.65 | 2.46 | 2.67 | 2.75 | 2.80 | 3.72 | 4.93 | 3.72 | 2.40 | 0.71 |
| Q11 | 2.78 | 3.29 | 2.25 | 2.65 | 3.17 | 2.15 | 1.85 | 2.35 | 3.17 | 3.95 |
| Q12 | 2.69 | 2.60 | 2.69 | 2.65 | 2.69 | 3.74 | 4.36 | 3.73 | 2.45 | 1.26 |
| Q13 | 2.16 | 2.39 | 2.31 | 2.22 | 2.62 | 2.67 | 3.56 | 2.69 | 2.29 | 2.54 |
| Q14 | 2.15 | 2.32 | 2.12 | 2.04 | 2.71 | 2.66 | 3.57 | 2.67 | 2.42 | 2.45 |
| Q15 | 2.78 | 3.16 | 2.06 | 2.50 | 3.29 | 2.38 | 1.83 | 2.12 | 3.32 | 3.93 |
| Q16 | 3.25 | 4.02 | 3.06 | 3.28 | 4.44 | 2.48 | 1.32 | 2.64 | 4.03 | 4.91 |
| Q17 | 2.13 | 2.18 | 2.24 | 1.91 | 3.03 | 2.54 | 3.94 | 2.43 | 2.10 | 2.28 |
| Q18 | 3.28 | 3.94 | 2.91 | 3.23 | 4.50 | 2.66 | 1.29 | 2.44 | 4.07 | 4.91 |
| Q19 | 2.49 | 2.80 | 2.05 | 2.52 | 3.87 | 2.25 | 2.25 | 2.06 | 2.65 | 3.52 |
| Q20 | 2.55 | 2.88 | 2.55 | 2.72 | 4.12 | 1.97 | 1.89 | 2.12 | 3.15 | 3.99 |
| Q21 | 2.17 | 2.09 | 2.40 | 2.14 | 2.95 | 2.40 | 3.93 | 2.49 | 2.21 | 2.08 |
| Q22 | 1.98 | 2.61 | 0.95 | 1.81 | 2.32 | 2.48 | 2.91 | 2.28 | 2.37 | 2.61 |
| Q23 | 1.84 | 2.42 | 1.36 | 2.01 | 2.10 | 2.30 | 2.90 | 2.46 | 2.54 | 2.75 |
| Q24 | 2.74 | 2.92 | 2.52 | 2.85 | 4.09 | 2.36 | 1.91 | 2.45 | 3.10 | 4.12 |
| Q25 | 1.80 | 2.34 | 1.38 | 2.00 | 2.10 | 2.16 | 2.37 | 2.33 | 2.45 | 2.74 |

TABLE 9-continued

| | | | | | | | | | | |
|---|---|---|---|---|---|---|---|---|---|---|
| Q26 | 2.87 | 3.07 | 2.50 | 2.88 | 3.95 | 2.45 | 1.91 | 2.39 | 2.91 | 4.10 |
| Q27 | 2.03 | 2.54 | 0.94 | 1.83 | 2.28 | 2.45 | 2.94 | 2.24 | 2.28 | 2.56 |
| Q28 | 2.49 | 2.80 | 2.05 | 2.52 | 3.87 | 2.25 | 2.25 | 2.06 | 2.65 | 3.52 |
| Q29 | 2.35 | 2.63 | 2.53 | 2.37 | 3.83 | 1.81 | 2.44 | 1.81 | 2.70 | 3.47 |
| Q30 | 2.24 | 2.53 | 2.11 | 2.56 | 3.62 | 2.09 | 2.43 | 2.32 | 2.67 | 3.44 |

| | Q11 | Q12 | Q13 | Q14 | Q15 | Q16 | Q17 | Q18 | Q19 | Q20 |
|---|---|---|---|---|---|---|---|---|---|---|
| Size of Cluster | 191 | 587 | 305 | 281 | 185 | 182 | 270 | 185 | 519 | 196 |
| Q1 | 2.72 | 2.59 | 2.24 | 2.24 | 2.80 | 3.19 | 2.25 | 3.22 | 2.45 | 2.49 |
| Q2 | 3.34 | 2.68 | 2.52 | 2.37 | 3.21 | 4.01 | 2.14 | 3.96 | 2.79 | 2.83 |
| Q3 | 2.16 | 2.74 | 2.35 | 2.15 | 2.03 | 2.99 | 2.18 | 2.86 | 1.94 | 2.44 |
| Q4 | 2.58 | 2.63 | 2.16 | 1.98 | 2.12 | 3.25 | 1.97 | 3.16 | 2.48 | 2.67 |
| Q5 | 3.13 | 2.67 | 2.63 | 2.71 | 3.26 | 4.41 | 3.10 | 4.48 | 3.73 | 4.09 |
| Q6 | 2.15 | 3.54 | 2.56 | 2.60 | 2.38 | 2.47 | 2.56 | 2.66 | 2.25 | 1.97 |
| Q7 | 1.86 | 4.74 | 3.61 | 3.62 | 1.84 | 1.33 | 3.96 | 1.29 | 2.24 | 1.89 |
| Q8 | 2.36 | 3.54 | 2.62 | 2.57 | 2.13 | 2.64 | 2.45 | 2.44 | 2.03 | 2.11 |
| Q9 | 3.17 | 2.57 | 2.36 | 2.47 | 3.32 | 4.05 | 2.15 | 4.09 | 2.71 | 3.15 |
| Q10 | 3.95 | 1.44 | 2.01 | 2.44 | 3.91 | 4.90 | 2.28 | 4.91 | 3.51 | 3.99 |
| Q11 | 0.30 | 3.93 | 2.81 | 2.93 | 1.07 | 1.79 | 3.24 | 2.01 | 2.18 | 2.32 |
| Q12 | 3.97 | 1.10 | 2.47 | 2.42 | 3.98 | 4.91 | 2.04 | 4.85 | 3.60 | 3.87 |
| Q13 | 2.84 | 2.28 | 0.64 | 1.20 | 2.96 | 3.74 | 1.82 | 3.66 | 2.67 | 2.73 |
| Q14 | 2.91 | 2.36 | 1.21 | 0.61 | 2.82 | 3.66 | 1.59 | 3.74 | 2.67 | 2.90 |
| Q15 | 1.08 | 3.96 | 2.96 | 2.80 | 0.28 | 2.04 | 3.11 | 1.77 | 2.37 | 2.17 |
| Q16 | 1.79 | 4.83 | 3.79 | 3.70 | 2.06 | 0.27 | 3.98 | 1.06 | 2.14 | 2.01 |
| Q17 | 3.24 | 2.25 | 1.77 | 1.53 | 3.10 | 3.97 | 0.53 | 4.00 | 2.69 | 2.68 |
| Q18 | 2.02 | 4.82 | 3.71 | 3.79 | 1.78 | 1.07 | 4.01 | 0.26 | 2.06 | 1.86 |
| Q19 | 2.29 | 3.63 | 2.70 | 2.69 | 2.45 | 2.24 | 2.66 | 2.16 | 0.70 | 1.28 |
| Q20 | 2.31 | 3.96 | 2.79 | 2.94 | 2.18 | 2.00 | 2.72 | 1.87 | 1.41 | 0.28 |
| Q21 | 3.11 | 2.33 | 1.57 | 1.75 | 3.18 | 4.02 | 1.17 | 3.95 | 2.51 | 2.85 |
| Q22 | 2.21 | 2.73 | 2.36 | 2.16 | 2.20 | 2.93 | 2.38 | 2.76 | 2.01 | 2.58 |
| Q23 | 2.02 | 2.63 | 2.16 | 2.26 | 2.21 | 2.79 | 2.50 | 2.89 | 2.18 | 2.44 |
| Q24 | 1.71 | 4.08 | 2.95 | 2.76 | 1.35 | 1.89 | 3.14 | 1.98 | 2.06 | 2.07 |
| Q25 | 1.94 | 2.64 | 2.14 | 2.24 | 2.14 | 2.79 | 2.39 | 2.90 | 2.22 | 2.53 |
| Q26 | 1.36 | 4.09 | 2.77 | 2.90 | 1.62 | 1.99 | 3.21 | 1.94 | 1.96 | 2.02 |
| Q27 | 2.24 | 2.69 | 2.32 | 2.11 | 2.04 | 2.99 | 2.30 | 2.82 | 2.04 | 2.62 |
| Q28 | 2.29 | 3.64 | 2.70 | 2.69 | 2.45 | 2.24 | 2.67 | 2.15 | 0.70 | 1.27 |
| Q29 | 2.33 | 3.25 | 2.04 | 2.01 | 2.32 | 2.54 | 2.29 | 2.52 | 2.06 | 1.88 |
| Q30 | 3.32 | 3.39 | 2.60 | 2.48 | 2.20 | 2.07 | 2.42 | 2.32 | 1.31 | 1.32 |

| | Q21 | Q22 | Q23 | Q24 | Q25 | Q26 | Q27 | Q28 | Q29 | Q30 |
|---|---|---|---|---|---|---|---|---|---|---|
| Size of Cluster | 303 | 772 | 716 | 232 | 702 | 239 | 650 | 491 | 284 | 298 |
| Q1 | 2.23 | 2.03 | 1.83 | 2.79 | 1.83 | 2.92 | 2.01 | 2.45 | 2.26 | 2.17 |
| Q2 | 2.08 | 2.46 | 2.28 | 2.86 | 2.27 | 3.03 | 2.43 | 2.80 | 2.56 | 2.45 |
| Q3 | 2.36 | 0.98 | 1.37 | 2.38 | 1.30 | 2.53 | 0.95 | 1.95 | 2.63 | 1.90 |
| Q4 | 2.20 | 1.83 | 2.02 | 2.87 | 2.02 | 2.90 | 1.80 | 2.48 | 2.26 | 2.59 |
| Q5 | 3.03 | 2.43 | 2.21 | 4.09 | 2.21 | 3.94 | 2.37 | 3.73 | 3.78 | 3.59 |
| Q6 | 2.44 | 2.47 | 2.27 | 2.35 | 2.27 | 2.45 | 2.51 | 2.25 | 1.77 | 2.08 |
| Q7 | 3.95 | 3.01 | 2.99 | 1.92 | 2.99 | 1.90 | 3.02 | 2.24 | 2.45 | 2.45 |
| Q8 | 2.53 | 2.29 | 2.45 | 2.44 | 2.44 | 2.38 | 2.33 | 2.03 | 1.76 | 2.29 |
| Q9 | 2.22 | 2.31 | 2.48 | 3.09 | 2.48 | 2.90 | 2.29 | 2.71 | 2.69 | 2.67 |
| Q10 | 2.06 | 2.66 | 2.73 | 4.07 | 2.73 | 4.14 | 2.61 | 3.52 | 3.49 | 3.39 |
| Q11 | 3.13 | 2.25 | 2.06 | 1.71 | 2.06 | 1.35 | 2.26 | 2.18 | 2.33 | 2.32 |
| Q12 | 2.21 | 2.68 | 2.68 | 4.15 | 2.68 | 4.09 | 2.64 | 3.60 | 3.38 | 3.27 |
| Q13 | 1.03 | 2.31 | 2.12 | 2.88 | 2.12 | 2.72 | 2.27 | 2.67 | 1.96 | 2.62 |
| Q14 | 1.79 | 2.12 | 2.24 | 2.70 | 2.24 | 2.86 | 2.07 | 2.67 | 1.94 | 2.50 |
| Q15 | 3.21 | 2.06 | 2.25 | 1.35 | 2.25 | 1.62 | 2.06 | 2.37 | 2.33 | 2.20 |
| Q16 | 4.04 | 3.07 | 2.93 | 1.89 | 2.92 | 2.02 | 3.09 | 2.13 | 2.55 | 2.07 |
| Q17 | 1.18 | 2.23 | 2.37 | 3.10 | 2.37 | 3.22 | 2.21 | 2.69 | 2.23 | 2.37 |
| Q18 | 3.97 | 2.91 | 3.02 | 1.99 | 3.02 | 1.92 | 2.93 | 2.05 | 2.53 | 2.32 |
| Q19 | 2.49 | 2.05 | 2.24 | 2.04 | 2.24 | 1.89 | 2.09 | 0.70 | 2.04 | 1.18 |
| Q20 | 2.89 | 2.56 | 2.47 | 2.06 | 2.47 | 2.00 | 2.60 | 1.40 | 1.88 | 1.33 |
| Q21 | 0.57 | 2.39 | 2.26 | 3.26 | 2.26 | 3.11 | 2.37 | 2.52 | 2.22 | 2.58 |
| Q22 | 2.52 | 0.96 | 1.35 | 2.57 | 1.35 | 2.59 | 0.91 | 2.02 | 2.47 | 1.99 |
| Q23 | 2.43 | 1.36 | 0.93 | 2.61 | 0.92 | 2.59 | 1.33 | 2.19 | 2.46 | 1.79 |
| Q24 | 3.26 | 2.52 | 2.51 | 0.27 | 2.50 | 1.08 | 2.54 | 2.06 | 2.20 | 1.85 |
| Q25 | 2.33 | 1.38 | 0.94 | 2.65 | 0.95 | 2.61 | 1.32 | 2.23 | 2.50 | 1.80 |
| Q26 | 3.15 | 2.50 | 2.53 | 1.08 | 2.53 | 0.28 | 2.54 | 1.97 | 2.20 | 2.04 |
| Q27 | 2.44 | 0.93 | 1.36 | 2.61 | 1.35 | 2.68 | 0.87 | 2.04 | 2.51 | 1.98 |
| Q28 | 2.49 | 2.05 | 2.24 | 2.04 | 2.24 | 1.89 | 2.09 | 0.70 | 2.04 | 1.18 |
| Q29 | 2.29 | 2.53 | 2.53 | 2.20 | 2.53 | 2.21 | 2.54 | 2.06 | 0.30 | 2.14 |
| Q30 | 2.63 | 2.11 | 1.95 | 1.86 | 1.95 | 2.05 | 2.11 | 1.31 | 2.14 | 0.31 |

TABLE 10

| Method | Family TOL (Å) | TOL (Å) | Sealevel (% peak) | $\Sigma_{i=1}^{30} |C_i|$ | Unique $\Sigma_{i=1}^{30} |C_i|$ | Avg. Intracluster RMSD | Avg. Intercluster RMSD |
|---|---|---|---|---|---|---|---|
| O | 0.5 | 0.5 | 0 | 886 | 886 | 0.28 | 2.83 |
| O | 0.75 | 0.75 | 0 | 2364 | 2364 | 0.32 | 2.62 |
| G | 0.5 | 0.3 | 0.125 | 203 | 203 | 0.30 | 2.84 |
| G | 0.5 | 0.3 | 0.25 | 201 | 201 | 0.30 | 2.84 |
| G | 0.5 | 0.3 | 0.5 | 188 | 188 | 0.31 | 2.84 |
| G | 0.5 | 0.3 | 0.75 | 108 | 108 | 0.37 | 2.85 |
| G | 0.5 | 0.5 | 0.125 | 1913 | 1913 | 0.31 | 2.83 |
| G | 0.5 | 0.5 | 0.25 | 1197 | 1197 | 0.28 | 2.83 |
| G | 0.5 | 0.5 | 0.5 | 568 | 568 | 0.27 | 2.84 |
| G | 0.5 | 0.5 | 0.75 | 194 | 194 | 0.37 | 2.84 |
| G | 0.5 | 0.7 | 0.125 | 2038 | 1975 | 0.32 | 2.83 |
| G | 0.5 | 0.7 | 0.25 | 1199 | 1199 | 0.28 | 2.83 |
| G | 0.5 | 0.7 | 0.5 | 568 | 568 | 0.27 | 2.84 |
| G | 0.5 | 0.7 | 0.75 | 194 | 194 | 0.37 | 2.84 |
| G | 0.75 | 0.3 | 0.125 | 175 | 175 | 0.33 | 2.65 |
| G | 0.75 | 0.3 | 0.25 | 175 | 175 | 0.33 | 2.65 |
| G | 0.75 | 0.3 | 0.5 | 175 | 175 | 0.33 | 2.65 |
| G | 0.75 | 0.3 | 0.75 | 162 | 162 | 0.34 | 2.65 |
| G | 0.75 | 0.5 | 0.125 | 2759 | 2759 | 0.32 | 2.62 |
| G | 0.75 | 0.5 | 0.25 | 2516 | 2516 | 0.31 | 2.62 |
| G | 0.75 | 0.5 | 0.5 | 1601 | 1601 | 0.28 | 2.62 |
| G | 0.75 | 0.5 | 0.75 | 728 | 728 | 0.26 | 2.62 |
| G | 0.75 | 0.7 | 0.125 | 4067 | 3811 | 0.42 | 2.61 |
| G | 0.75 | 0.7 | 0.25 | 2916 | 2916 | 0.35 | 2.62 |
| G | 0.75 | 0.7 | 0.5 | 1621 | 1621 | 0.28 | 2.62 |
| G | 0.75 | 0.7 | 0.75 | 729 | 729 | 0.26 | 2.62 |

TABLE 11

| | Q1 | Q2 | Q3 | Q4 | Q5 | Q6 | Q7 | Q8 | Q9 | Q10 | Q11 |
|---|---|---|---|---|---|---|---|---|---|---|---|
| Size of Cluster | 101 | 113 | 98 | 112 | 91 | 91 | 115 | 109 | 43 | 95 | 200 |
| Q1 | 0.31 | 3.46 | 3.16 | 2.24 | 2.40 | 1.94 | 2.55 | 2.91 | 2.33 | 2.05 | 3.80 |
| Q2 | 3.40 | 0.37 | 2.11 | 2.88 | 2.27 | 2.99 | 2.97 | 2.73 | 3.06 | 3.85 | 1.94 |
| Q3 | 3.17 | 2.11 | 0.38 | 3.38 | 2.61 | 3.11 | 3.02 | 2.73 | 4.14 | 4.04 | 2.33 |
| Q4 | 2.23 | 2.88 | 3.33 | 0.34 | 2.33 | 1.65 | 1.85 | 2.53 | 2.16 | 2.37 | 3.05 |
| Q5 | 2.40 | 2.26 | 2.60 | 2.33 | 0.37 | 3.09 | 2.53 | 2.56 | 3.12 | 2.90 | 2.74 |
| Q6 | 1.93 | 2.98 | 3.38 | 1.65 | 2.08 | 0.34 | 2.53 | 2.66 | 2.67 | 2.66 | 3.22 |
| Q7 | 2.55 | 2.96 | 2.98 | 1.84 | 2.52 | 2.54 | 0.39 | 1.35 | 3.51 | 3.33 | 2.84 |
| Q8 | 2.93 | 2.73 | 2.72 | 2.55 | 2.55 | 2.67 | 1.35 | 0.39 | 3.83 | 3.89 | 2.65 |
| Q9 | 2.35 | 3.94 | 4.12 | 2.75 | 3.11 | 2.68 | 3.52 | 3.83 | 0.27 | 1.43 | 4.62 |
| Q10 | 2.06 | 3.85 | 4.04 | 2.38 | 2.91 | 2.60 | 3.34 | 3.85 | 1.42 | 0.30 | 4.56 |
| Q11 | 3.75 | 1.85 | 2.24 | 3.00 | 2.70 | 3.16 | 2.85 | 2.56 | 4.58 | 4.51 | 0.75 |
| Q12 | 2.85 | 2.43 | 2.27 | 2.82 | 2.01 | 2.74 | 2.14 | 2.09 | 3.50 | 3.56 | 2.51 |
| Q13 | 2.80 | 2.44 | 2.25 | 2.74 | 2.22 | 2.70 | 2.20 | 2.10 | 3.37 | 3.45 | 2.66 |
| Q14 | 2.41 | 2.96 | 2.97 | 2.14 | 2.36 | 2.62 | 1.11 | 1.37 | 3.58 | 3.48 | 2.75 |
| Q15 | 2.51 | 2.44 | 3.07 | 1.88 | 2.60 | 2.25 | 2.52 | 2.70 | 2.38 | 2.40 | 3.30 |
| Q16 | 2.77 | 4.11 | 4.73 | 3.00 | 3.60 | 2.66 | 3.89 | 4.30 | 1.66 | 1.88 | 5.01 |
| Q17 | 2.31 | 2.52 | 2.84 | 1.32 | 2.16 | 1.15 | 1.86 | 1.82 | 3.04 | 3.00 | 2.57 |
| Q18 | 2.29 | 2.98 | 3.48 | 1.93 | 2.16 | 2.00 | 2.51 | 2.67 | 2.42 | 2.45 | 3.36 |
| Q19 | 2.11 | 2.61 | 2.66 | 2.26 | 2.32 | 3.20 | 2.62 | 2.64 | 2.18 | 2.54 | 3.36 |
| Q20 | 2.64 | 4.11 | 4.72 | 2.96 | 3.48 | 2.60 | 3.86 | 4.29 | 1.35 | 2.08 | 4.95 |
| Q21 | 2.42 | 2.52 | 2.83 | 1.96 | 2.39 | 1.84 | 1.98 | 1.84 | 3.16 | 3.07 | 2.42 |
| Q22 | 2.40 | 2.86 | 3.32 | 1.10 | 2.48 | 1.96 | 2.07 | 2.51 | 2.94 | 2.60 | 2.86 |
| Q23 | 3.16 | 2.19 | 2.02 | 2.77 | 2.49 | 3.02 | 2.25 | 2.14 | 3.55 | 3.83 | 2.41 |
| Q24 | 1.34 | 3.26 | 2.95 | 2.76 | 2.35 | 2.47 | 3.00 | 3.06 | 1.98 | 2.07 | 3.91 |
| Q25 | 3.12 | 2.17 | 2.06 | 2.92 | 2.37 | 3.02 | 2.22 | 2.13 | 3.67 | 3.93 | 2.26 |
| Q26 | 2.11 | 2.61 | 2.65 | 2.27 | 2.32 | 2.21 | 2.63 | 2.64 | 2.18 | 2.55 | 3.37 |
| Q27 | 2.37 | 2.31 | 2.71 | 2.33 | 1.44 | 1.96 | 2.60 | 2.00 | 2.85 | 2.47 | 2.98 |
| Q28 | 3.22 | 2.34 | 2.09 | 2.35 | 1.64 | 2.18 | 2.47 | 2.84 | 2.87 | 2.76 | 2.80 |
| Q29 | 2.36 | 3.16 | 3.80 | 2.44 | 3.00 | 2.18 | 3.37 | 3.49 | 2.12 | 2.03 | 4.08 |
| Q30 | 2.53 | 3.16 | 3.80 | 2.20 | 2.84 | 1.90 | 3.22 | 3.47 | 2.15 | 2.13 | 4.12 |

| | Q12 | Q13 | Q14 | Q15 | Q16 | Q17 | Q18 | Q19 | Q20 | Q21 |
|---|---|---|---|---|---|---|---|---|---|---|
| Size of Cluster | 184 | 154 | 113 | 109 | 97 | 115 | 188 | 270 | 104 | 113 |
| Q1 | 2.86 | 2.73 | 2.43 | 2.52 | 2.76 | 2.32 | 2.33 | 2.13 | 2.63 | 2.43 |
| Q2 | 2.50 | 2.49 | 2.07 | 2.44 | 4.12 | 2.52 | 3.01 | 2.69 | 4.12 | 2.52 |
| Q3 | 2.33 | 2.32 | 2.97 | 3.07 | 4.75 | 2.85 | 3.52 | 2.72 | 4.74 | 2.84 |
| Q4 | 2.80 | 2.73 | 2.15 | 1.88 | 2.99 | 1.32 | 1.93 | 2.31 | 2.95 | 1.70 |
| Q5 | 2.08 | 2.25 | 2.37 | 2.59 | 3.57 | 2.15 | 2.23 | 2.34 | 3.47 | 2.38 |
| Q6 | 2.80 | 2.74 | 2.61 | 2.25 | 2.63 | 1.51 | 2.05 | 2.26 | 2.59 | 1.86 |

TABLE 11-continued

| | | | | | | | | | |
|---|---|---|---|---|---|---|---|---|---|
| Q7 | 2.18 | 2.19 | 1.12 | 2.52 | 3.89 | 1.85 | 2.52 | 2.67 | 3.85 | 1.96 |
| Q8 | 2.14 | 2.17 | 1.39 | 2.70 | 4.32 | 1.82 | 2.72 | 2.70 | 4.30 | 1.83 |
| Q9 | 3.49 | 3.39 | 3.59 | 2.36 | 1.65 | 3.04 | 2.43 | 2.07 | 1.35 | 3.15 |
| Q10 | 3.59 | 3.49 | 3.48 | 2.40 | 1.87 | 2.97 | 2.42 | 2.38 | 2.04 | 3.07 |
| Q11 | 2.48 | 2.61 | 2.69 | 3.24 | 4.99 | 2.49 | 3.34 | 3.31 | 4.91 | 2.33 |
| Q12 | 0.67 | 1.20 | 2.32 | 2.85 | 4.07 | 2.36 | 2.67 | 2.63 | 3.95 | 2.15 |
| Q13 | 1.22 | 0.61 | 2.13 | 2.89 | 3.99 | 2.21 | 2.47 | 2.61 | 4.10 | 2.23 |
| Q14 | 2.31 | 2.16 | 0.40 | 2.58 | 3.90 | 2.01 | 2.34 | 2.66 | 3.93 | 1.87 |
| Q15 | 2.81 | 2.86 | 2.59 | 0.34 | 2.73 | 1.80 | 2.18 | 1.65 | 2.72 | 1.78 |
| Q16 | 4.10 | 4.01 | 3.01 | 2.71 | 0.27 | 3.41 | 2.96 | 2.61 | 1.08 | 3.43 |
| Q17 | 2.40 | 2.24 | 2.00 | 1.80 | 3.41 | 0.36 | 1.92 | 2.01 | 3.40 | 1.09 |
| Q18 | 2.68 | 2.47 | 2.31 | 2.18 | 2.94 | 1.84 | 0.65 | 2.19 | 2.86 | 2.08 |
| Q19 | 2.60 | 2.58 | 2.77 | 1.53 | 2.53 | 1.94 | 2.17 | 0.74 | 2.71 | 2.01 |
| Q20 | 3.99 | 4.12 | 3.93 | 2.70 | 1.08 | 3.41 | 2.90 | 2.71 | 0.27 | 3.41 |
| Q21 | 2.20 | 2.28 | 1.88 | 1.78 | 3.42 | 1.08 | 2.13 | 2.07 | 3.41 | 0.39 |
| Q22 | 2.05 | 2.76 | 1.85 | 1.91 | 2.99 | 1.59 | 2.11 | 2.37 | 3.03 | 1.31 |
| Q23 | 1.78 | 1.55 | 2.20 | 2.81 | 4.22 | 2.26 | 2.79 | 2.53 | 4.24 | 2.28 |
| Q24 | 2.71 | 2.70 | 3.03 | 2.20 | 2.51 | 2.59 | 2.51 | 1.89 | 2.52 | 2.59 |
| Q25 | 1.58 | 1.73 | 2.41 | 2.79 | 4.24 | 2.31 | 2.86 | 2.46 | 4.20 | 2.20 |
| Q26 | 2.60 | 2.56 | 2.78 | 1.53 | 2.57 | 1.95 | 2.18 | 0.72 | 2.73 | 2.02 |
| Q27 | 1.99 | 2.26 | 2.48 | 2.14 | 2.99 | 2.24 | 2.33 | 1.91 | 2.81 | 2.44 |
| Q28 | 2.14 | 1.02 | 2.54 | 2.25 | 2.83 | 2.29 | 2.49 | 2.07 | 3.00 | 2.23 |
| Q29 | 3.27 | 3.14 | 3.27 | 1.95 | 2.02 | 2.82 | 1.87 | 2.28 | 1.77 | 2.69 |
| Q30 | 3.13 | 3.29 | 3.41 | 1.94 | 1.79 | 2.67 | 2.16 | 2.29 | 2.02 | 2.82 |

| | Q22 | Q23 | Q24 | Q25 | Q26 | Q27 | Q28 | Q29 | Q30 |
|---|---|---|---|---|---|---|---|---|---|
| Size of Cluster | 125 | 122 | 125 | 137 | 256 | 198 | 156 | 140 | 143 |
| Q1 | 2.40 | 3.14 | 1.33 | 3.12 | 2.13 | 2.41 | 2.21 | 2.55 | 2.53 |
| Q2 | 2.86 | 2.21 | 3.25 | 2.19 | 2.68 | 2.34 | 2.33 | 3.16 | 3.15 |
| Q3 | 3.33 | 2.02 | 2.94 | 2.06 | 2.71 | 2.78 | 2.70 | 3.85 | 3.86 |
| Q4 | 1.10 | 2.78 | 2.76 | 2.92 | 2.30 | 2.27 | 2.33 | 2.43 | 2.20 |
| Q5 | 2.47 | 2.49 | 2.35 | 2.37 | 2.35 | 1.48 | 1.63 | 2.90 | 2.83 |
| Q6 | 1.96 | 3.01 | 2.43 | 2.98 | 2.26 | 2.00 | 2.18 | 2.17 | 1.89 |
| Q7 | 2.07 | 2.24 | 3.00 | 2.22 | 2.66 | 2.64 | 2.46 | 3.38 | 3.22 |
| Q8 | 2.55 | 2.18 | 3.04 | 2.13 | 2.69 | 2.94 | 2.85 | 3.49 | 3.46 |
| Q9 | 2.94 | 3.57 | 1.95 | 3.68 | 2.07 | 2.80 | 2.87 | 2.11 | 2.16 |
| Q10 | 2.60 | 3.82 | 2.05 | 3.93 | 2.38 | 2.52 | 2.76 | 2.03 | 2.14 |
| Q11 | 2.80 | 2.36 | 3.85 | 2.19 | 3.30 | 2.91 | 2.73 | 4.10 | 4.14 |
| Q12 | 2.64 | 1.72 | 2.66 | 1.49 | 2.63 | 1.98 | 2.06 | 3.21 | 3.07 |
| Q13 | 2.76 | 1.51 | 2.66 | 1.68 | 2.60 | 2.26 | 1.86 | 3.08 | 3.24 |
| Q14 | 1.84 | 2.21 | 3.03 | 2.40 | 2.66 | 2.52 | 2.52 | 3.26 | 3.42 |
| Q15 | 1.93 | 2.83 | 2.20 | 2.80 | 1.64 | 3.20 | 2.27 | 2.00 | 1.94 |
| Q16 | 3.00 | 4.23 | 2.52 | 4.25 | 2.62 | 3.00 | 2.85 | 2.04 | 1.79 |
| Q17 | 1.58 | 2.26 | 2.58 | 2.31 | 2.01 | 2.28 | 2.30 | 2.83 | 2.66 |
| Q18 | 2.07 | 2.80 | 2.44 | 2.86 | 2.19 | 2.37 | 2.44 | 1.79 | 2.09 |
| Q19 | 2.40 | 2.50 | 1.81 | 2.38 | 0.72 | 1.96 | 2.14 | 2.20 | 2.20 |
| Q20 | 3.03 | 4.25 | 3.53 | 4.21 | 2.71 | 2.86 | 3.00 | 1.77 | 2.02 |
| Q21 | 1.29 | 2.29 | 2.57 | 2.21 | 2.00 | 2.43 | 2.23 | 2.68 | 2.83 |
| Q22 | 0.33 | 2.92 | 2.78 | 2.76 | 2.36 | 2.34 | 2.24 | 2.24 | 2.45 |
| Q23 | 2.92 | 0.41 | 3.02 | 1.11 | 2.52 | 2.48 | 2.25 | 3.40 | 3.47 |
| Q24 | 2.77 | 3.03 | 0.32 | 3.02 | 1.89 | 2.29 | 2.24 | 2.26 | 2.24 |
| Q25 | 2.75 | 1.11 | 3.01 | 0.38 | 2.45 | 2.32 | 2.43 | 3.47 | 3.40 |
| Q26 | 2.41 | 2.48 | 1.80 | 2.38 | 0.72 | 1.97 | 2.16 | 2.21 | 2.21 |
| Q27 | 2.30 | 2.47 | 2.22 | 2.30 | 1.91 | 0.56 | 1.12 | 2.52 | 2.30 |
| Q28 | 2.25 | 2.26 | 2.24 | 2.47 | 2.07 | 1.21 | 0.34 | 2.28 | 2.47 |
| Q29 | 2.24 | 3.42 | 2.25 | 3.48 | 2.28 | 2.50 | 2.29 | 0.29 | 1.09 |
| Q30 | 2.46 | 3.48 | 2.23 | 3.41 | 2.29 | 2.27 | 2.47 | 1.08 | 0.31 |

TABLE 12

| Method | Family TOL (Å) | TOL (Å) | Scalevel (% peak) | $\Sigma_{i=1}^{30} |C_i|$ | Unique $\Sigma_{i=1}^{30} |C_i|$ | Avg. Intracluster RMSD | Avg. Intercluster RMSD |
|---|---|---|---|---|---|---|---|
| O | 0.5 | 0.5 | 0 | 414 | 407 | 0.32 | 2.73 |
| O | 0.75 | 0.75 | 0 | 1227 | 1227 | 0.34 | 2.60 |
| G | 0.5 | 0.3 | 0.125 | 75 | 75 | 0.22 | 2.74 |
| G | 0.5 | 0.3 | 0.25 | 75 | 75 | 0.22 | 2.74 |
| G | 0.5 | 0.3 | 0.5 | 73 | 73 | 0.22 | 2.74 |
| G | 0.5 | 0.3 | 0.75 | 57 | 57 | 0.18 | 2.74 |
| G | 0.5 | 0.5 | 0.125 | 799 | 774 | 0.31 | 2.73 |
| G | 0.5 | 0.5 | 0.25 | 626 | 607 | 0.30 | 2.73 |
| G | 0.5 | 0.5 | 0.5 | 336 | 328 | 0.31 | 2.74 |
| G | 0.5 | 0.5 | 0.75 | 132 | 131 | 0.35 | 2.73 |
| G | 0.5 | 0.7 | 0.125 | 1008 | 977 | 0.33 | 2.73 |
| G | 0.5 | 0.7 | 0.25 | 713 | 690 | 0.31 | 2.73 |
| G | 0.5 | 0.7 | 0.5 | 343 | 335 | 0.31 | 2.74 |

TABLE 12-continued

| Method | Family TOL (Å) | TOL (Å) | Scalevel (% peak) | $\Sigma_{i=1}^{30} |C_i|$ | Unique $\Sigma_{i=1}^{30} |C_i|$ | Avg. Intracluster RMSD | Avg. Intercluster RMSD |
|---|---|---|---|---|---|---|---|
| G | 0.5 | 0.7 | 0.75 | 133 | 131 | 0.36 | 2.74 |
| G | 0.75 | 0.3 | 0.125 | 75 | 75 | 0.37 | 2.63 |
| G | 0.75 | 0.3 | 0.25 | 75 | 75 | 0.37 | 2.63 |
| G | 0.75 | 0.3 | 0.5 | 75 | 75 | 0.37 | 2.63 |
| G | 0.75 | 0.3 | 0.75 | 72 | 72 | 0.31 | 2.63 |
| G | 0.75 | 0.5 | 0.125 | 924 | 924 | 0.32 | 2.61 |
| G | 0.75 | 0.5 | 0.25 | 875 | 875 | 0.32 | 2.61 |
| G | 0.75 | 0.5 | 0.5 | 632 | 632 | 0.30 | 2.61 |
| G | 0.75 | 0.5 | 0.75 | 304 | 304 | 0.34 | 2.61 |
| G | 0.75 | 0.7 | 0.125 | 1874 | 1874 | 0.37 | 2.60 |
| G | 0.75 | 0.7 | 0.25 | 1429 | 1429 | 0.34 | 2.60 |
| G | 0.75 | 0.7 | 0.5 | 773 | 773 | 0.31 | 2.61 |
| G | 0.75 | 0.7 | 0.75 | 315 | 315 | 0.34 | 2.61 |
| G | 0.75 | 0.9 | 0.125 | 2042 | 1904 | 0.39 | 2.60 |
| G | 0.75 | 0.9 | 0.25 | 1431 | 1431 | 0.34 | 2.60 |
| G | 0.75 | 0.9 | 0.5 | 773 | 773 | 0.31 | 2.61 |
| G | 0.75 | 0.9 | 0.75 | 315 | 315 | 0.34 | 2.61 |

TABLE 13

| | Q1 | Q2 | Q3 | Q4 | Q5 | Q6 | Q7 | Q8 | Q9 | Q10 | Q11 | Q12 | Q13 | Q14 | Q15 | Q16 |
|---|---|---|---|---|---|---|---|---|---|---|---|---|---|---|---|---|
| Size of Cluster | 52 | 50 | 49 | 45 | 60 | 60 | 53 | 50 | 47 | 60 | 54 | 62 | 71 | 61 | 61 | 72 |
| Q1 | 0.38 | 1.11 | 2.67 | 2.31 | 2.36 | 3.10 | 2.90 | 2.93 | 2.85 | 2.29 | 2.61 | 2.55 | 2.87 | 2.15 | 2.71 | 2.20 |
| Q2 | 1.13 | 0.34 | 2.53 | 2.50 | 2.26 | 2.94 | 3.04 | 2.72 | 2.92 | 2.37 | 2.71 | 2.60 | 2.94 | 2.34 | 2.70 | 2.37 |
| Q3 | 2.67 | 2.51 | 0.41 | 3.65 | 2.28 | 2.82 | 2.79 | 2.63 | 3.98 | 2.57 | 3.22 | 2.72 | 2.17 | 2.97 | 1.92 | 2.54 |
| Q4 | 2.31 | 2.51 | 3.65 | 0.32 | 2.48 | 4.28 | 3.53 | 3.91 | 2.03 | 3.04 | 2.02 | 2.76 | 3.91 | 2.43 | 3.20 | 3.32 |
| Q5 | 2.36 | 2.25 | 2.28 | 2.48 | 0.39 | 3.07 | 2.43 | 2.64 | 2.67 | 2.48 | 2.34 | 2.27 | 2.60 | 2.18 | 1.72 | 2.48 |
| Q6 | 3.10 | 2.94 | 2.83 | 4.27 | 3.07 | 0.37 | 3.14 | 2.56 | 4.65 | 2.73 | 3.90 | 3.59 | 2.05 | 2.93 | 3.09 | 2.42 |
| Q7 | 2.91 | 3.03 | 2.79 | 3.53 | 2.44 | 3.14 | 0.41 | 2.62 | 3.09 | 2.33 | 3.05 | 2.23 | 2.15 | 3.07 | 2.32 | 2.22 |
| Q8 | 2.91 | 2.71 | 2.64 | 3.91 | 2.65 | 2.56 | 2.60 | 0.37 | 4.00 | 2.83 | 3.50 | 2.83 | 1.89 | 3.19 | 2.69 | 2.80 |
| Q9 | 2.87 | 2.93 | 3.98 | 2.05 | 2.67 | 4.66 | 3.10 | 4.01 | 0.34 | 3.35 | 2.37 | 2.78 | 4.10 | 2.79 | 3.30 | 3.50 |
| Q10 | 2.32 | 2.38 | 2.59 | 3.04 | 2.50 | 2.73 | 2.34 | 2.84 | 3.34 | 0.36 | 2.92 | 2.35 | 2.43 | 2.34 | 2.27 | 1.31 |
| Q11 | 2.60 | 2.68 | 3.23 | 2.02 | 2.32 | 3.88 | 3.05 | 3.49 | 2.37 | 2.90 | 0.37 | 2.83 | 3.44 | 2.03 | 2.97 | 3.19 |
| Q12 | 2.55 | 2.62 | 2.72 | 2.75 | 2.26 | 3.59 | 2.22 | 2.83 | 2.79 | 2.34 | 2.84 | 0.40 | 2.88 | 2.79 | 2.02 | 2.29 |
| Q13 | 2.87 | 2.94 | 2.17 | 3.90 | 2.60 | 2.05 | 2.15 | 1.88 | 4.10 | 2.41 | 3.44 | 2.88 | 0.43 | 2.96 | 2.56 | 2.38 |
| Q14 | 2.15 | 2.34 | 2.98 | 2.43 | 2.18 | 2.93 | 3.07 | 3.20 | 2.79 | 2.33 | 2.04 | 2.80 | 2.96 | 0.35 | 2.80 | 2.66 |
| Q15 | 2.71 | 2.68 | 1.91 | 3.20 | 1.72 | 3.09 | 2.32 | 2.70 | 3.30 | 2.28 | 2.98 | 2.03 | 2.55 | 2.80 | 0.42 | 2.09 |
| Q16 | 2.20 | 2.37 | 2.54 | 3.31 | 2.46 | 2.42 | 2.22 | 2.80 | 3.48 | 1.30 | 3.17 | 2.29 | 2.38 | 2.65 | 2.08 | 0.39 |
| Q17 | 1.60 | 1.83 | 2.76 | 2.48 | 1.97 | 2.71 | 2.73 | 2.78 | 2.86 | 2.22 | 2.63 | 2.56 | 2.66 | 1.83 | 2.50 | 2.08 |
| Q18 | 2.03 | 2.51 | 2.13 | 3.55 | 2.39 | 2.64 | 2.56 | 1.97 | 3.84 | 2.50 | 3.29 | 2.65 | 2.36 | 2.88 | 2.13 | 2.38 |
| Q19 | 2.37 | 2.26 | 2.63 | 3.22 | 2.50 | 2.72 | 2.41 | 2.77 | 3.3 | 1.34 | 2.9 | 2.51 | 2.28 | 2.44 | 1.95 | 1.21 |
| Q20 | 1.88 | 2.16 | 3.07 | 1.74 | 2.02 | 3.89 | 2.72 | 3.19 | 2.27 | 2.36 | 2.39 | 2.17 | 3.24 | 2.66 | 2.47 | 2.36 |
| Q21 | 2.14 | 1.90 | 3.25 | 1.97 | 2.19 | 3.74 | 2.93 | 3.07 | 2.47 | 2.58 | 2.28 | 1.94 | 3.12 | 2.60 | 2.43 | 2.60 |
| Q22 | 2.43 | 2.30 | 2.18 | 2.94 | 1.90 | 3.14 | 2.41 | 3.01 | 2.88 | 2.21 | 2.69 | 2.19 | 2.88 | 2.58 | 1.33 | 2.44 |
| Q23 | 2.36 | 2.25 | 2.63 | 3.22 | 2.50 | 2.72 | 2.41 | 2.77 | 3.53 | 1.35 | 2.96 | 2.51 | 2.28 | 2.44 | 1.95 | 1.20 |
| Q24 | 2.75 | 2.77 | 2.93 | 2.15 | 2.12 | 3.82 | 2.71 | 3.17 | 2.7 | 2.95 | 1.30 | 2.58 | 3.07 | 2.30 | 2.63 | 3.02 |
| Q25 | 2.79 | 2.66 | 2.76 | 2.30 | 1.86 | 3.75 | 2.74 | 3.34 | 2.05 | 2.83 | 1.64 | 2.50 | 3.24 | 2.02 | 2.54 | 2.88 |
| Q26 | 1.87 | 1.62 | 2.65 | 2.37 | 2.09 | 2.50 | 2.78 | 2.64 | 2.95 | 1.93 | 2.55 | 2.37 | 2.69 | 2.05 | 2.51 | 1.75 |
| Q27 | 2.96 | 2.94 | 4.08 | 2.13 | 3.05 | 4.95 | 3.86 | 4.70 | 1.89 | 3.77 | 2.42 | 3.37 | 4.46 | 2.92 | 3.66 | 3.90 |
| Q28 | 2.37 | 2.17 | 3.20 | 2.13 | 2.09 | 3.89 | 2.90 | 2.99 | 2.0 | 2.70 | 2.12 | 1.76 | 3.15 | 2.41 | 2.75 | 3.99 |
| Q29 | 2.21 | 2.32 | 3.06 | 1.93 | 1.91 | 3.89 | 2.85 | 3.19 | 1.69 | 2.53 | 2.18 | 2.10 | 3.33 | 2.48 | 2.78 | 2.88 |
| Q30 | 2.00 | 2.89 | 2.86 | 3.12 | 2.28 | 3.94 | 1.35 | 2.63 | 2.0 | 2.40 | 2.73 | 2.39 | 2.30 | 2.74 | 2.15 | 2.37 |

| | Q17 | Q18 | Q19 | Q20 | Q21 | Q22 | Q23 | Q24 | Q25 | Q26 | Q27 | Q28 | Q29 | Q30 |
|---|---|---|---|---|---|---|---|---|---|---|---|---|---|---|
| Size of Cluster | 64 | 63 | 138 | 56 | 55 | 67 | 138 | 78 | 79 | 73 | 67 | 79 | 77 | 101 |
| Q1 | 1.60 | 2.63 | 2.39 | 1.87 | 2.14 | 2.42 | 2.39 | 2.73 | 2.79 | 1.86 | 2.94 | 2.37 | 2.19 | 2.92 |
| Q2 | 1.84 | 2.51 | 2.29 | 2.16 | 1.90 | 2.30 | 2.29 | 2.78 | 2.66 | 1.63 | 2.94 | 2.16 | 2.32 | 2.92 |
| Q3 | 2.74 | 2.14 | 2.66 | 3.07 | 3.25 | 2.17 | 2.66 | 2.93 | 2.75 | 2.64 | 4.07 | 3.19 | 3.06 | 2.83 |
| Q4 | 2.49 | 3.55 | 3.28 | 1.74 | 1.97 | 2.94 | 3.28 | 2.15 | 2.30 | 2.37 | 2.12 | 2.13 | 1.93 | 3.11 |
| Q5 | 1.96 | 2.39 | 2.51 | 2.01 | 2.19 | 1.90 | 2.51 | 2.12 | 1.90 | 2.09 | 3.06 | 2.10 | 1.92 | 2.30 |
| Q6 | 2.70 | 2.64 | 2.63 | 3.89 | 3.75 | 3.14 | 2.63 | 3.86 | 3.75 | 2.50 | 4.95 | 3.91 | 3.88 | 3.05 |
| Q7 | 2.72 | 2.57 | 2.47 | 2.73 | 2.92 | 2.40 | 2.47 | 2.70 | 2.73 | 2.76 | 3.85 | 2.90 | 2.85 | 1.34 |
| Q8 | 2.79 | 1.97 | 2.82 | 3.18 | 3.06 | 3.00 | 2.82 | 3.17 | 3.34 | 2.65 | 4.72 | 2.98 | 3.19 | 2.64 |
| Q9 | 2.88 | 3.86 | 3.53 | 2.28 | 2.48 | 2.89 | 3.53 | 2.28 | 2.06 | 2.96 | 1.87 | 2.01 | 1.71 | 2.83 |
| Q10 | 2.25 | 2.51 | 1.45 | 2.36 | 2.60 | 2.22 | 1.45 | 2.95 | 2.84 | 1.93 | 3.76 | 2.70 | 2.52 | 2.37 |
| Q11 | 2.66 | 3.30 | 3.03 | 2.39 | 2.28 | 2.69 | 3.03 | 1.30 | 1.63 | 2.52 | 2.42 | 2.11 | 2.17 | 2.65 |
| Q12 | 2.54 | 2.66 | 2.48 | 2.17 | 1.93 | 2.17 | 2.48 | 2.58 | 2.49 | 2.37 | 3.36 | 1.76 | 2.09 | 2.38 |
| Q13 | 2.65 | 2.37 | 2.34 | 3.23 | 3.12 | 2.87 | 2.34 | 3.06 | 3.24 | 2.69 | 4.45 | 3.14 | 3.33 | 2.27 |
| Q14 | 1.83 | 2.86 | 2.32 | 2.67 | 2.59 | 2.59 | 2.32 | 2.30 | 2.03 | 2.03 | 2.93 | 2.41 | 2.49 | 2.74 |
| Q15 | 2.50 | 2.13 | 2.04 | 2.45 | 2.41 | 1.31 | 2.04 | 2.61 | 2.52 | 2.51 | 3.64 | 2.74 | 2.78 | 2.16 |
| Q16 | 2.07 | 2.38 | 1.33 | 2.35 | 2.60 | 2.45 | 1.33 | 2.99 | 2.87 | 1.74 | 3.89 | 2.99 | 2.89 | 2.37 |

TABLE 13-continued

| | | | | | | | | | | | | | | |
|---|---|---|---|---|---|---|---|---|---|---|---|---|---|---|
| Q17 | 0.38 | 2.43 | 1.85 | 2.12 | 2.34 | 2.37 | 1.85 | 2.63 | 2.50 | 1.11 | 3.09 | 2.41 | 2.25 | 2.32 |
| Q18 | 2.43 | 0.39 | 2.33 | 3.15 | 3.06 | 2.71 | 2.33 | 3.10 | 3.25 | 2.17 | 4.38 | 2.97 | 3.17 | 2.95 |
| Q19 | 1.76 | 2.39 | 0.73 | 2.45 | 2.30 | 2.17 | 0.73 | 2.84 | 2.93 | 1.95 | 3.93 | 2.72 | 2.92 | 2.28 |
| Q20 | 2.12 | 3.13 | 2.52 | 0.37 | 1.10 | 2.48 | 2.52 | 2.39 | 2.20 | 2.34 | 2.82 | 1.59 | 1.31 | 2.64 |
| Q21 | 2.32 | 3.06 | 2.38 | 1.11 | 0.37 | 2.35 | 2.38 | 2.23 | 2.36 | 2.12 | 2.83 | 1.32 | 1.72 | 2.56 |
| Q22 | 2.35 | 2.73 | 2.20 | 2.48 | 2.35 | 0.37 | 2.20 | 2.38 | 2.13 | 2.33 | 3.45 | 2.72 | 2.62 | 2.13 |
| Q23 | 1.75 | 2.38 | 0.73 | 2.44 | 2.29 | 2.19 | 0.73 | 2.84 | 2.93 | 1.95 | 3.92 | 2.72 | 2.92 | 2.29 |
| Q24 | 2.63 | 3.10 | 2.89 | 2.41 | 2.24 | 2.39 | 2.89 | 0.33 | 1.10 | 2.54 | 2.16 | 2.03 | 2.21 | 2.22 |
| Q25 | 2.49 | 3.24 | 2.99 | 2.22 | 2.36 | 2.14 | 2.99 | 1.10 | 0.35 | 2.54 | 2.14 | 2.24 | 2.24 | 2.24 |
| Q26 | 1.10 | 2.18 | 2.03 | 2.35 | 2.13 | 2.33 | 2.03 | 2.55 | 2.57 | 0.36 | 3.07 | 2.27 | 2.41 | 2.26 |
| Q27 | 3.10 | 4.39 | 3.86 | 2.81 | 2.81 | 3.43 | 3.86 | 2.16 | 2.15 | 3.08 | 0.28 | 2.57 | 2.52 | 3.42 |
| Q28 | 2.40 | 2.98 | 2.74 | 1.60 | 1.32 | 2.71 | 2.74 | 2.03 | 2.24 | 2.27 | 2.55 | 0.32 | 1.10 | 2.62 |
| Q29 | 2.24 | 3.17 | 2.90 | 1.31 | 1.71 | 2.61 | 2.90 | 2.20 | 2.01 | 2.41 | 2.50 | 1.10 | 0.35 | 2.64 |
| Q30 | 2.31 | 2.95 | 2.35 | 2.64 | 2.55 | 2.10 | 2.35 | 2.23 | 2.20 | 2.24 | 3.42 | 2.60 | 2.63 | 0.47 |

TABLE 14

| | |
|---|---|
| H: | α-helix |
| B: | residue in isolated beta-bridge |
| E: | extended strand, participates in beta ladder |
| G: | 3-helix (3/10 helix) |
| I: | 5 helix (π helix) |
| T: | hydrogen bonded turn |
| S: | bend |
| U: | no assignment |

TABLE 15

| Cluster | $|C_i|$ | H | B | E | G | I | T | S | U |
|---|---|---|---|---|---|---|---|---|---|
| C1 | 616 | 0.96 | 0.00 | 0.00 | 0.00 | 0.00 | 0.02 | 0.01 | 0.01 |
| C2 | 682 | 0.01 | 0.03 | 0.56 | 0.01 | 0.00 | 0.03 | 0.05 | 0.32 |
| C3 | 278 | 0.80 | 0.00 | 0.00 | 0.06 | 0.00 | 0.09 | 0.01 | 0.03 |
| C4 | 258 | 0.94 | 0.00 | 0.00 | 0.00 | 0.00 | 0.03 | 0.00 | 0.02 |
| C5 | 609 | 0.96 | 0.00 | 0.00 | 0.00 | 0.00 | 0.02 | 0.01 | 0.01 |
| C6 | 1809 | 0.96 | 0.00 | 0.00 | 0.00 | 0.00 | 0.03 | 0.00 | 0.01 |
| C7 | 255 | 0.92 | 0.00 | 0.00 | 0.00 | 0.00 | 0.06 | 0.01 | 0.01 |
| C8 | 264 | 0.94 | 0.00 | 0.00 | 0.01 | 0.00 | 0.03 | 0.01 | 0.01 |
| C9 | 300 | 0.97 | 0.00 | 0.00 | 0.00 | 0.00 | 0.02 | 0.00 | 0.01 |
| C10 | 274 | 0.95 | 0.00 | 0.00 | 0.00 | 0.00 | 0.03 | 0.00 | 0.01 |
| C11 | 266 | 0.93 | 0.00 | 0.00 | 0.01 | 0.00 | 0.04 | 0.01 | 0.01 |
| C12 | 423 | 0.95 | 0.00 | 0.00 | 0.00 | 0.00 | 0.02 | 0.01 | 0.01 |
| C13 | 303 | 0.97 | 0.00 | 0.00 | 0.00 | 0.00 | 0.01 | 0.01 | 0.01 |
| C14 | 1750 | 0.96 | 0.00 | 0.00 | 0.00 | 0.00 | 0.02 | 0.00 | 0.01 |
| C15 | 310 | 0.96 | 0.00 | 0.00 | 0.00 | 0.00 | 0.03 | 0.00 | 0.01 |
| C16 | 304 | 0.96 | 0.00 | 0.00 | 0.00 | 0.00 | 0.02 | 0.00 | 0.01 |
| C17 | 476 | 0.96 | 0.00 | 0.00 | 0.00 | 0.00 | 0.02 | 0.01 | 0.01 |
| C18 | 1262 | 0.96 | 0.00 | 0.00 | 0.00 | 0.00 | 0.02 | 0.00 | 0.01 |
| C19 | 345 | 0.96 | 0.00 | 0.00 | 0.00 | 0.00 | 0.02 | 0.01 | 0.01 |
| C20 | 340 | 0.97 | 0.00 | 0.00 | 0.00 | 0.00 | 0.02 | 0.00 | 0.01 |
| C21 | 944 | 0.96 | 0.00 | 0.00 | 0.00 | 0.00 | 0.02 | 0.00 | 0.01 |
| C22 | 1667 | 0.97 | 0.00 | 0.00 | 0.00 | 0.00 | 0.02 | 0.00 | 0.01 |
| C23 | 1648 | 0.97 | 0.00 | 0.00 | 0.00 | 0.00 | 0.02 | 0.00 | 0.01 |
| C24 | 386 | 0.96 | 0.00 | 0.00 | 0.00 | 0.00 | 0.02 | 0.01 | 0.01 |
| C25 | 882 | 0.96 | 0.00 | 0.00 | 0.00 | 0.00 | 0.02 | 0.00 | 0.01 |
| C26 | 428 | 0.96 | 0.00 | 0.00 | 0.00 | 0.00 | 0.02 | 0.00 | 0.01 |
| C27 | 855 | 0.96 | 0.00 | 0.00 | 0.00 | 0.00 | 0.02 | 0.00 | 0.01 |
| C28 | 473 | 0.96 | 0.00 | 0.00 | 0.00 | 0.00 | 0.02 | 0.00 | 0.01 |
| C29 | 515 | 0.91 | 0.00 | 0.00 | 0.00 | 0.00 | 0.03 | 0.01 | 0.01 |
| C30 | 861 | 0.97 | 0.00 | 0.00 | 0.00 | 0.00 | 0.02 | 0.00 | 0.01 |

TABLE 16

| Cluster | $|C_i|$ | H | B | E | G | I | T | S | U |
|---|---|---|---|---|---|---|---|---|---|
| C1 | 298 | 0.97 | 0.00 | 0.00 | 0.00 | 0.00 | 0.02 | 0.01 | 0.01 |
| C2 | 238 | 0.97 | 0.00 | 0.00 | 0.00 | 0.00 | 0.02 | 0.00 | 0.01 |
| C3 | 821 | 0.96 | 0.00 | 0.00 | 0.00 | 0.00 | 0.02 | 0.00 | 0.01 |
| C4 | 309 | 0.97 | 0.00 | 0.00 | 0.00 | 0.00 | 0.02 | 0.01 | 0.00 |
| C5 | 245 | 0.97 | 0.00 | 0.00 | 0.00 | 0.00 | 0.02 | 0.00 | 0.00 |
| C6 | 174 | 0.97 | 0.00 | 0.00 | 0.00 | 0.00 | 0.02 | 0.00 | 0.01 |
| C7 | 147 | 0.96 | 0.00 | 0.00 | 0.00 | 0.00 | 0.03 | 0.01 | 0.00 |
| C8 | 168 | 0.97 | 0.00 | 0.00 | 0.00 | 0.00 | 0.02 | 0.00 | 0.01 |
| C9 | 178 | 0.97 | 0.00 | 0.00 | 0.00 | 0.00 | 0.02 | 0.00 | 0.01 |
| C10 | 296 | 0.98 | 0.00 | 0.00 | 0.00 | 0.00 | 0.01 | 0.00 | 0.01 |
| C11 | 191 | 0.97 | 0.00 | 0.00 | 0.00 | 0.00 | 0.01 | 0.00 | 0.01 |
| C12 | 587 | 0.97 | 0.00 | 0.00 | 0.00 | 0.00 | 0.02 | 0.00 | 0.00 |
| C13 | 305 | 0.97 | 0.00 | 0.00 | 0.00 | 0.00 | 0.02 | 0.00 | 0.01 |
| C14 | 281 | 0.98 | 0.00 | 0.00 | 0.00 | 0.00 | 0.02 | 0.00 | 0.00 |
| C15 | 185 | 0.97 | 0.00 | 0.00 | 0.00 | 0.00 | 0.02 | 0.00 | 0.01 |
| C16 | 182 | 0.95 | 0.00 | 0.00 | 0.00 | 0.00 | 0.04 | 0.00 | 0.01 |
| C17 | 270 | 0.97 | 0.00 | 0.00 | 0.00 | 0.00 | 0.02 | 0.00 | 0.01 |
| C18 | 185 | 0.97 | 0.00 | 0.00 | 0.00 | 0.00 | 0.02 | 0.00 | 0.01 |
| C19 | 519 | 0.96 | 0.00 | 0.00 | 0.00 | 0.00 | 0.02 | 0.01 | 0.01 |
| C20 | 196 | 0.97 | 0.00 | 0.00 | 0.00 | 0.00 | 0.02 | 0.00 | 0.01 |
| C21 | 308 | 0.98 | 0.00 | 0.00 | 0.00 | 0.00 | 0.01 | 0.00 | 0.01 |
| C22 | 772 | 0.97 | 0.00 | 0.00 | 0.00 | 0.00 | 0.02 | 0.00 | 0.01 |
| C23 | 716 | 0.97 | 0.00 | 0.00 | 0.00 | 0.00 | 0.02 | 0.00 | 0.01 |
| C24 | 232 | 0.96 | 0.00 | 0.00 | 0.00 | 0.00 | 0.02 | 0.00 | 0.01 |
| C25 | 702 | 0.97 | 0.00 | 0.00 | 0.00 | 0.00 | 0.02 | 0.00 | 0.01 |
| C26 | 239 | 0.97 | 0.00 | 0.00 | 0.00 | 0.00 | 0.02 | 0.00 | 0.01 |
| C27 | 650 | 0.97 | 0.00 | 0.00 | 0.00 | 0.00 | 0.02 | 0.00 | 0.01 |
| C28 | 491 | 0.97 | 0.00 | 0.00 | 0.00 | 0.00 | 0.02 | 0.00 | 0.01 |
| C29 | 284 | 0.97 | 0.00 | 0.00 | 0.00 | 0.00 | 0.01 | 0.00 | 0.01 |
| C30 | 298 | 0.97 | 0.00 | 0.00 | 0.00 | 0.00 | 0.02 | 0.00 | 0.00 |

TABLE 17

| Cluster | $|C_i|$ | H | B | E | G | I | T | S | U |
|---|---|---|---|---|---|---|---|---|---|
| C1 | 101 | 0.97 | 0.00 | 0.00 | 0.00 | 0.00 | 0.02 | 0.00 | 0.01 |
| C2 | 113 | 0.97 | 0.00 | 0.00 | 0.00 | 0.00 | 0.02 | 0.00 | 0.00 |
| C3 | 98 | 0.98 | 0.00 | 0.00 | 0.00 | 0.00 | 0.01 | 0.01 | 0.01 |
| C4 | 112 | 0.97 | 0.00 | 0.00 | 0.00 | 0.00 | 0.02 | 0.00 | 0.01 |
| C5 | 91 | 0.98 | 0.00 | 0.00 | 0.00 | 0.00 | 0.01 | 0.00 | 0.01 |
| C6 | 91 | 0.98 | 0.00 | 0.00 | 0.00 | 0.00 | 0.01 | 0.00 | 0.01 |
| C7 | 115 | 0.98 | 0.00 | 0.00 | 0.00 | 0.00 | 0.01 | 0.00 | 0.00 |
| C8 | 109 | 0.98 | 0.00 | 0.00 | 0.00 | 0.00 | 0.01 | 0.00 | 0.01 |
| C9 | 93 | 0.97 | 0.00 | 0.00 | 0.00 | 0.00 | 0.02 | 0.00 | 0.01 |
| C10 | 95 | 0.96 | 0.00 | 0.00 | 0.00 | 0.00 | 0.03 | 0.01 | 0.01 |
| C11 | 200 | 0.98 | 0.00 | 0.00 | 0.00 | 0.00 | 0.01 | 0.00 | 0.01 |
| C12 | 184 | 0.98 | 0.00 | 0.00 | 0.00 | 0.00 | 0.02 | 0.00 | 0.01 |
| C13 | 154 | 0.98 | 0.00 | 0.00 | 0.00 | 0.00 | 0.02 | 0.00 | 0.00 |
| C14 | 113 | 0.97 | 0.00 | 0.00 | 0.00 | 0.00 | 0.01 | 0.01 | 0.01 |
| C15 | 109 | 0.98 | 0.00 | 0.00 | 0.00 | 0.00 | 0.02 | 0.00 | 0.01 |
| C16 | 97 | 0.97 | 0.00 | 0.00 | 0.00 | 0.00 | 0.02 | 0.00 | 0.01 |
| C17 | 115 | 0.97 | 0.00 | 0.00 | 0.00 | 0.00 | 0.03 | 0.00 | 0.01 |
| C18 | 188 | 0.98 | 0.00 | 0.00 | 0.00 | 0.00 | 0.02 | 0.00 | 0.00 |
| C19 | 270 | 0.97 | 0.00 | 0.00 | 0.00 | 0.00 | 0.02 | 0.00 | 0.00 |
| C20 | 104 | 0.96 | 0.00 | 0.00 | 0.00 | 0.00 | 0.02 | 0.00 | 0.01 |
| C21 | 113 | 0.98 | 0.00 | 0.00 | 0.00 | 0.00 | 0.01 | 0.00 | 0.01 |
| C22 | 125 | 0.97 | 0.00 | 0.00 | 0.00 | 0.00 | 0.02 | 0.01 | 0.01 |
| C23 | 122 | 0.98 | 0.00 | 0.00 | 0.00 | 0.00 | 0.01 | 0.00 | 0.01 |
| C24 | 125 | 0.98 | 0.00 | 0.00 | 0.00 | 0.00 | 0.02 | 0.00 | 0.00 |
| C25 | 137 | 0.98 | 0.00 | 0.00 | 0.00 | 0.00 | 0.01 | 0.01 | 0.01 |
| C26 | 256 | 0.98 | 0.00 | 0.00 | 0.00 | 0.00 | 0.01 | 0.00 | 0.00 |
| C27 | 198 | 0.98 | 0.00 | 0.00 | 0.00 | 0.00 | 0.01 | 0.00 | 0.01 |
| C28 | 156 | 0.98 | 0.00 | 0.00 | 0.00 | 0.00 | 0.01 | 0.00 | 0.01 |

TABLE 17-continued

| Cluster | $|C_i|$ | H | B | E | G | I | T | S | U |
|---|---|---|---|---|---|---|---|---|---|
| C29 | 140 | 0.98 | 0.00 | 0.00 | 0.00 | 0.00 | 0.01 | 0.00 | 0.00 |
| C30 | 143 | 0.98 | 0.00 | 0.00 | 0.00 | 0.00 | 0.01 | 0.00 | 0.01 |

TABLE 18

| Cluster | $|C_i|$ | H | B | E | G | I | T | S | U |
|---|---|---|---|---|---|---|---|---|---|
| C1 | 52 | 0.97 | 0.00 | 0.00 | 0.01 | 0.00 | 0.01 | 0.00 | 0.01 |
| C2 | 50 | 0.98 | 0.00 | 0.00 | 0.00 | 0.00 | 0.01 | 0.00 | 0.01 |
| C3 | 49 | 0.99 | 0.00 | 0.00 | 0.00 | 0.00 | 0.01 | 0.00 | 0.01 |
| C4 | 45 | 0.98 | 0.00 | 0.00 | 0.00 | 0.00 | 0.01 | 0.00 | 0.01 |
| C5 | 60 | 0.98 | 0.00 | 0.00 | 0.00 | 0.00 | 0.02 | 0.00 | 0.00 |
| C6 | 60 | 0.99 | 0.00 | 0.00 | 0.00 | 0.00 | 0.01 | 0.00 | 0.00 |
| C7 | 53 | 0.99 | 0.00 | 0.00 | 0.00 | 0.00 | 0.01 | 0.00 | 0.00 |
| C8 | 50 | 0.99 | 0.00 | 0.00 | 0.00 | 0.00 | 0.01 | 0.00 | 0.01 |
| C9 | 47 | 0.97 | 0.00 | 0.00 | 0.00 | 0.00 | 0.02 | 0.01 | 0.00 |
| C10 | 60 | 1.00 | 0.00 | 0.00 | 0.00 | 0.00 | 0.00 | 0.00 | 0.00 |
| C11 | 54 | 0.98 | 0.00 | 0.00 | 0.00 | 0.00 | 0.02 | 0.00 | 0.00 |
| C12 | 62 | 0.97 | 0.00 | 0.00 | 0.00 | 0.00 | 0.02 | 0.01 | 0.00 |
| C13 | 71 | 0.99 | 0.00 | 0.00 | 0.00 | 0.00 | 0.01 | 0.00 | 0.01 |
| C14 | 61 | 0.98 | 0.00 | 0.00 | 0.00 | 0.00 | 0.02 | 0.00 | 0.00 |
| C15 | 61 | 0.99 | 0.00 | 0.00 | 0.00 | 0.00 | 0.00 | 0.00 | 0.01 |
| C16 | 72 | 0.98 | 0.00 | 0.00 | 0.00 | 0.00 | 0.01 | 0.00 | 0.01 |
| C17 | 64 | 0.97 | 0.00 | 0.00 | 0.00 | 0.00 | 0.03 | 0.00 | 0.01 |
| C18 | 63 | 0.98 | 0.00 | 0.00 | 0.00 | 0.00 | 0.01 | 0.00 | 0.00 |
| C19 | 138 | 0.99 | 0.00 | 0.00 | 0.00 | 0.00 | 0.01 | 0.00 | 0.01 |
| C20 | 56 | 0.98 | 0.00 | 0.00 | 0.00 | 0.00 | 0.01 | 0.00 | 0.01 |
| C21 | 55 | 0.98 | 0.00 | 0.00 | 0.00 | 0.00 | 0.01 | 0.00 | 0.01 |
| C22 | 67 | 0.97 | 0.00 | 0.00 | 0.00 | 0.00 | 0.01 | 0.01 | 0.00 |
| C23 | 138 | 0.99 | 0.00 | 0.00 | 0.00 | 0.00 | 0.01 | 0.00 | 0.01 |
| C24 | 78 | 0.98 | 0.00 | 0.00 | 0.00 | 0.00 | 0.01 | 0.01 | 0.01 |
| C25 | 79 | 0.98 | 0.00 | 0.00 | 0.00 | 0.00 | 0.02 | 0.00 | 0.00 |
| C26 | 73 | 0.97 | 0.00 | 0.00 | 0.00 | 0.00 | 0.02 | 0.00 | 0.01 |
| C27 | 67 | 0.98 | 0.00 | 0.00 | 0.00 | 0.00 | 0.01 | 0.00 | 0.01 |
| C28 | 79 | 0.97 | 0.00 | 0.00 | 0.00 | 0.00 | 0.02 | 0.01 | 0.01 |
| C29 | 77 | 0.99 | 0.00 | 0.00 | 0.00 | 0.00 | 0.01 | 0.00 | 0.01 |
| C30 | 101 | 0.98 | 0.00 | 0.00 | 0.00 | 0.00 | 0.01 | 0.00 | 0.00 |

TABLE 19

| Motif size | 4 | 5 | 6 | 7 |
|---|---|---|---|---|
| C1 | 0.08 | 0.07 | 0.09 | 0.06 |
| C2 | 0.99 | 0.03 | 0.04 | 0.04 |
| C3 | 0.21 | 0.08 | 0.05 | 0.04 |
| C4 | 0.07 | 0.06 | 0.04 | 0.00 |
| C5 | 0.08 | 0.06 | 0.03 | 0.03 |
| C6 | 0.07 | 0.03 | 0.02 | 0.00 |
| C7 | 0.09 | 0.05 | 0.04 | 0.02 |
| C8 | 0.05 | 0.04 | 0.05 | 0.02 |
| C9 | 0.06 | 0.05 | 0.04 | 0.09 |
| C10 | 0.05 | 0.04 | 0.05 | 0.00 |
| C11 | 0.06 | 0.07 | 0.04 | 0.09 |
| C12 | 0.08 | 0.06 | 0.06 | 0.10 |
| C13 | 0.06 | 0.07 | 0.05 | 0.03 |
| C14 | 0.06 | 0.02 | 0.06 | 0.00 |
| C15 | 0.03 | 0.03 | 0.02 | 0.08 |
| C16 | 0.03 | 0.05 | 0.05 | 0.03 |
| C17 | 0.06 | 0.04 | 0.04 | 0.06 |
| C18 | 0.05 | 0.02 | 0.03 | 0.05 |
| C19 | 0.06 | 0.07 | 0.07 | 0.03 |
| C20 | 0.05 | 0.03 | 0.05 | 0.05 |
| C21 | 0.06 | 0.04 | 0.05 | 0.07 |
| C22 | 0.06 | 0.07 | 0.07 | 0.07 |
| C23 | 0.05 | 0.07 | 0.05 | 0.03 |
| C24 | 0.03 | 0.03 | 0.09 | 0.05 |
| C25 | 0.05 | 0.06 | 0.05 | 0.06 |
| C26 | 0.02 | 0.07 | 0.06 | 0.04 |
| C27 | 0.05 | 0.06 | 0.03 | 0.03 |
| C28 | 0.03 | 0.06 | 0.04 | 0.09 |
| C29 | 0.04 | 0.02 | 0.03 | 0.03 |
| C30 | 0.05 | 0.02 | 0.02 | 0.05 |

TABLE 20

| Size of motif | 4 | 5 | 6 | 7 |
|---|---|---|---|---|
| C1 | UTBU | UUUUU | UUUUUU | HHHHHHS |
| C2 | UUUU | UUUUU | UUUUUU | HHHHHHT |
| C3 | UUUU | UUUUU | UUUUUU | HHHHHHS |
| C4 | UUUU | UUUUU | UUUUUU | HHHHHHU |
| C5 | HHHU | UUUUU | UUUUUU | UUUUUUU |
| C6 | EEEE | UUUUU | UUUUUU | UUUUUUU |
| C7 | UUUH | UUUUU | UUUUUU | UUUUUUU |
| C8 | UTUH | UUUUU | UUUUUU | UUUUUUU |
| C9 | SUUU | UUUUU | UUUUUU | UUUUUUU |
| C10 | UUUU | UUUUU | UUUUUU | UUUUUUU |
| C11 | UUUB | UUUUU | UUUUUU | UUUUUUU |
| C12 | UUUU | UUUUU | UUUUUU | UUUUUUU |
| C13 | UUEE | UUUUU | UUUUUU | UUUUUUU |
| C14 | EUUG | UUUUU | UUUUUU | UUUUUUU |
| C15 | UUUU | UUUUU | UUUUUU | UUUUUUU |
| C16 | UUUU | UUUUU | UUUUUU | UUUUUUU |
| C17 | HHHS | HHHHU | UUUUUU | UUUUUUU |
| C18 | EEEE | UUUUU | UUUUUU | UUUUUUU |
| C19 | GGSU | HHHHS | UUUUUU | UUUUUUU |
| C20 | EEEU | UUUUU | UUUUUU | UUUUUUU |
| C21 | EEEE | UUUUU | HHHHHU | UUUUUUU |
| C22 | EEEE | UUUUU | UUUUUU | UUUUUUU |
| C23 | EEEE | HHHHS | UUUUUU | UUUUUUU |
| C24 | SEEE | EEEEE | UUUUUU | UUUUUUU |
| C25 | HHHS | EEEEE | UUUUUU | UUUUUUU |
| C26 | EEEE | HHHHU | UUUUUU | UUUUUUU |
| C27 | EEEE | EEEEE | UUUUUU | UUUUUUU |
| C28 | EEES | EEEEE | HHHHHS | UUUUUUU |
| C29 | EEEE | HHHHU | HHHHHU | UUUUUUU |
| C30 | EEEE | EEEEE | EEEEEE | UUUUUUU |

TABLE 21

| Method | Size of motif | TOL | Sealevel (% peak) | $\Sigma_{i=1}^{30} |C_i|$ | Unique $\Sigma_{i=1}^{30} |C_i|$ | Avg. Intracluster RMSD | Avg. Intercluster RMSD |
|---|---|---|---|---|---|---|---|
| O | 4 | 0.75 | 0 | 1625 | 1573 | 0.54 | 2.69 |
| G | 4 | 0.5 | 0.25 | 6671 | 3770 | 0.52 | 2.69 |
| O | 5 | 0.75 | 0 | 712 | 712 | 0.29 | 2.72 |
| G | 5 | 0.7 | 0.125 | 1264 | 1264 | 0.37 | 2.72 |
| G | 5 | 0.9 | 0.125 | 2298 | 2298 | 0.43 | 2.74 |
| O | 6 | 0.75 | 0 | 591 | 591 | 0.25 | 2.50 |
| G | 6 | 0.7 | 0.125 | 680 | 680 | 0.26 | 2.50 |
| G | 6 | 0.9 | 0.125 | 771 | 771 | 0.27 | 2.49 |
| G | 6 | 1.1 | 0.125 | 771 | 771 | 0.27 | 2.49 |
| O | 7 | 0.75 | 0 | 479 | 479 | 0.26 | 2.33 |

TABLE 21-continued

| Method | Size of motif | TOL | Sealevel (% peak) | $\Sigma_{i=1}^{30} |C_i|$ | Unique $\Sigma_{i=1}^{30} |C_i|$ | Avg. Intracluster RMSD | Avg. Intercluster RMSD |
|---|---|---|---|---|---|---|---|
| G | 7 | 0.9 | 0.125 | 532 | 532 | 0.26 | 2.33 |
| G | 7 | 1.1 | 0.125 | 532 | 532 | 0.26 | 2.33 |

Legend
O: One-pass algorithm
G: Greedy algorithm

TABLE 22

| | Q1 | Q2 | Q3 | Q4 | Q5 | Q6 | Q7 | Q8 | Q9 | Q10 | Q11 | Q12 | Q13 | Q14 | Q15 | Q16 |
|---|---|---|---|---|---|---|---|---|---|---|---|---|---|---|---|---|
| Size of Cluster | 3 | 20 | 20 | 19 | 38 | 55 | 23 | 3 | 1 | 19 | 2 | 20 | 110 | 474 | 31 | 26 |
| Q1 | 0.50 | 3.29 | 2.50 | 2.93 | 3.05 | 1.53 | 3.68 | 1.61 | 1.20 | 2.52 | 3.18 | 1.92 | 4.12 | 3.29 | 2.99 | 3.12 |
| Q2 | 3.32 | 0.20 | 1.70 | 2.61 | 2.33 | 3.14 | 4.13 | 3.56 | 5.19 | 1.98 | 3.87 | 2.88 | 5.05 | 3.70 | 4.02 | 2.77 |
| Q3 | 2.53 | 1.70 | 0.33 | 1.78 | 1.57 | 2.25 | 3.30 | 2.99 | 3.99 | 2.04 | 2.85 | 1.80 | 3.90 | 2.50 | 2.88 | 2.05 |
| Q4 | 2.93 | 2.65 | 1.80 | 0.30 | 2.45 | 2.70 | 2.55 | 3.80 | 3.36 | 3.16 | 2.21 | 2.89 | 3.34 | 2.05 | 2.68 | 1.57 |
| Q5 | 3.00 | 2.35 | 1.52 | 2.39 | 0.41 | 2.43 | 3.66 | 3.08 | 1.37 | 2.36 | 3.28 | 1.84 | 4.15 | 2.98 | 3.02 | 2.79 |
| Q6 | 1.41 | 3.12 | 2.22 | 2.71 | 2.46 | 0.49 | 3.27 | 2.18 | 3.80 | 2.80 | 2.99 | 2.28 | 3.69 | 2.94 | 2.28 | 2.00 |
| Q7 | 3.68 | 4.12 | 3.29 | 2.59 | 3.66 | 3.28 | 0.24 | 4.86 | 1.57 | 4.61 | 0.93 | 3.83 | 1.65 | 1.66 | 1.78 | 1.70 |
| Q8 | 1.67 | 3.55 | 2.95 | 3.81 | 3.08 | 2.16 | 4.89 | 0.51 | 5.50 | 2.18 | 4.68 | 1.96 | 5.33 | 4.40 | 1.04 | 4.27 |
| Q9 | 1.24 | 5.10 | 4.00 | 3.39 | 4.40 | 3.83 | 1.62 | 5.50 | 0.00 | 5.51 | 1.61 | 4.48 | 0.86 | 1.95 | 1.91 | 2.70 |
| Q10 | 2.51 | 1.94 | 2.04 | 3.12 | 2.37 | 2.76 | 4.00 | 2.22 | 5.49 | 0.35 | 4.49 | 1.07 | 5.29 | 4.02 | 4.15 | 3.51 |
| Q11 | 3.42 | 1.17 | 3.07 | 2.28 | 3.44 | 2.94 | 1.12 | 4.03 | 1.13 | 4.58 | 0.83 | 3.82 | 1.45 | 1.31 | 1.31 | 1.94 |
| Q12 | 1.97 | 2.88 | 1.82 | 2.80 | 1.89 | 2.23 | 3.84 | 2.03 | 1.48 | 1.66 | 3.76 | 0.15 | 4.33 | 3.27 | 3.30 | 3.24 |
| Q13 | 4.11 | 5.06 | 3.92 | 3.40 | 4.21 | 3.67 | 1.61 | 5.32 | 0.66 | 5.37 | 1.57 | 4.35 | 0.57 | 1.84 | 1.70 | 2.79 |
| Q14 | 3.26 | 3.64 | 2.13 | 1.94 | 2.96 | 2.88 | 1.58 | 4.37 | 1.82 | 4.00 | 0.99 | 3.24 | 1.72 | 0.72 | 1.57 | 1.51 |
| Q15 | 2.08 | 4.01 | 2.86 | 2.70 | 3.04 | 2.28 | 1.76 | 4.03 | 1.84 | 4.18 | 1.11 | 3.28 | 1.74 | 1.67 | 0.03 | 2.35 |
| Q16 | 3.13 | 2.74 | 2.00 | 1.52 | 2.76 | 2.90 | 1.69 | 4.22 | 2.74 | 3.50 | 1.51 | 3.26 | 2.77 | 1.61 | 2.31 | 0.38 |
| Q17 | 1.38 | 3.27 | 2.72 | 2.92 | 3.12 | 1.65 | 3.64 | 2.08 | 1.29 | 2.56 | 3.51 | 2.03 | 4.26 | 3.47 | 3.12 | 3.11 |
| Q18 | 2.15 | 3.17 | 2.10 | 1.52 | 2.56 | 2.40 | 2.32 | 3.40 | 2.98 | 3.27 | 1.06 | 2.64 | 2.88 | 1.87 | 2.16 | 1.86 |
| Q19 | 4.14 | 4.96 | 3.88 | 3.35 | 4.18 | 3.70 | 1.62 | 3.38 | 0.96 | 5.21 | 1.57 | 4.19 | 1.05 | 1.78 | 1.81 | 2.70 |
| Q20 | 3.27 | 2.22 | 1.51 | 1.38 | 2.32 | 2.92 | 2.36 | 4.12 | 3.23 | 3.13 | 2.01 | 2.92 | 3.15 | 1.81 | 2.50 | 1.19 |
| Q21 | 1.94 | 2.77 | 1.78 | 1.94 | 2.31 | 2.09 | 2.85 | 2.72 | 3.53 | 2.17 | 2.68 | 1.49 | 3.39 | 2.26 | 2.51 | 2.21 |
| Q22 | 3.25 | 2.16 | 1.60 | 1.50 | 2.33 | 2.87 | 2.29 | 4.09 | 3.30 | 3.16 | 1.90 | 2.96 | 3.20 | 1.03 | 2.55 | 1.18 |
| Q23 | 1.84 | 2.74 | 1.85 | 1.89 | 2.45 | 2.00 | 2.75 | 2.74 | 3.15 | 2.25 | 2.51 | 1.77 | 3.32 | 2.25 | 2.41 | 2.06 |
| Q24 | 4.08 | 4.93 | 3.79 | 3.19 | 4.12 | 3.59 | 1.50 | 5.30 | 0.86 | 5.25 | 1.32 | 4.40 | 0.86 | 1.67 | 1.69 | 2.65 |
| Q25 | 3.30 | 3.41 | 2.67 | 2.01 | 2.87 | 2.74 | 1.02 | 4.20 | 2.13 | 4.16 | 1.56 | 3.33 | 2.63 | 2.05 | 1.98 | 1.79 |
| Q26 | 2.49 | 4.15 | 2.85 | 2.71 | 2.98 | 2.61 | 2.36 | 3.47 | 2.78 | 3.49 | 2.52 | 2.28 | 2.57 | 2.05 | 2.15 | 2.67 |
| Q27 | 2.30 | 4.15 | 2.86 | 2.77 | 3.01 | 2.63 | 2.40 | 3.48 | 2.78 | 3.48 | 2.53 | 2.30 | 2.58 | 2.08 | 2.15 | 2.68 |
| Q28 | 3.25 | 3.59 | 2.36 | 1.00 | 2.88 | 2.88 | 1.65 | 4.35 | 1.90 | 3.94 | 1.04 | 3.18 | 1.79 | 0.72 | 1.61 | 1.51 |
| Q29 | 3.19 | 3.59 | 2.38 | 1.98 | 2.91 | 2.88 | 1.68 | 4.33 | 2.01 | 3.88 | 1.09 | 3.16 | 1.82 | 0.80 | 1.62 | 1.51 |
| Q30 | 4.04 | 4.83 | 3.69 | 3.08 | 3.98 | 3.52 | 1.48 | 5.22 | 0.94 | 5.16 | 1.31 | 4.31 | 0.91 | 1.60 | 1.31 | 2.60 |

| | Q17 | Q18 | Q19 | Q20 | Q21 | Q22 | Q23 | Q24 | Q25 | Q26 | Q27 | Q28 | Q29 | Q30 |
|---|---|---|---|---|---|---|---|---|---|---|---|---|---|---|
| Size of Cluster | 50 | 99 | 1687 | 136 | 111 | 102 | 107 | 1649 | 79 | 236 | 228 | 342 | 299 | 682 |
| Q1 | 1.37 | 2.47 | 4.13 | 3.28 | 1.99 | 3.25 | 1.86 | 4.12 | 3.28 | 2.53 | 2.53 | 3.27 | 3.22 | 4.05 |
| Q2 | 3.24 | 3.17 | 4.95 | 2.31 | 2.81 | 2.22 | 2.78 | 4.94 | 3.42 | 4.07 | 4.08 | 3.63 | 3.60 | 4.85 |
| Q3 | 2.68 | 2.18 | 3.82 | 1.64 | 1.78 | 1.70 | 1.86 | 3.82 | 2.74 | 2.82 | 2.82 | 2.42 | 2.45 | 3.71 |
| Q4 | 2.86 | 1.52 | 3.23 | 1.56 | 2.01 | 1.60 | 1.94 | 3.23 | 1.98 | 2.71 | 2.72 | 1.99 | 2.08 | 3.10 |
| Q5 | 3.11 | 2.54 | 4.03 | 2.38 | 2.30 | 2.37 | 2.44 | 4.03 | 2.85 | 2.96 | 2.97 | 2.91 | 2.94 | 3.96 |
| Q6 | 1.62 | 2.42 | 3.66 | 2.96 | 2.13 | 2.89 | 2.02 | 3.66 | 2.73 | 2.60 | 2.61 | 2.91 | 2.92 | 3.54 |
| Q7 | 1.63 | 2.34 | 1.64 | 2.40 | 2.87 | 2.31 | 2.75 | 1.63 | 2.37 | 2.37 | 1.69 | 1.74 | 1.53 |  |
| Q8 | 2.08 | 3.47 | 5.31 | 4.12 | 2.74 | 4.09 | 2.75 | 5.31 | 4.27 | 3.19 | 3.49 | 4.37 | 4.34 | 5.23 |
| Q9 | 4.30 | 3.03 | 1.21 | 3.30 | 3.54 | 3.35 | 3.48 | 1.20 | 2.73 | 2.72 | 2.72 | 1.99 | 2.10 | 1.12 |
| Q10 | 2.53 | 3.30 | 5.19 | 3.15 | 2.24 | 3.17 | 2.32 | 5.19 | 4.18 | 3.52 | 3.52 | 3.96 | 3.89 | 5.14 |
| Q11 | 3.46 | 1.91 | 1.11 | 2.41 | 2.74 | 2.37 | 2.59 | 1.40 | 1.70 | 2.32 | 2.33 | 1.32 | 1.42 | 1.19 |
| Q12 | 2.05 | 2.64 | 4.28 | 2.92 | 1.57 | 2.97 | 1.83 | 4.28 | 3.34 | 2.36 | 2.36 | 3.22 | 3.19 | 4.26 |
| Q13 | 4.24 | 2.87 | 1.11 | 3.20 | 3.45 | 3.21 | 3.35 | 1.11 | 2.59 | 2.57 | 2.58 | 1.88 | 1.91 | 0.95 |
| Q14 | 3.40 | 1.82 | 1.67 | 1.82 | 2.23 | 1.91 | 2.30 | 1.66 | 2.04 | 2.01 | 2.01 | 0.65 | 0.76 | 1.52 |
| Q15 | 3.11 | 2.18 | 1.74 | 2.65 | 2.56 | 2.58 | 2.43 | 1.73 | 1.96 | 2.04 | 2.05 | 1.68 | 1.72 | 1.54 |
| Q16 | 3.10 | 1.83 | 2.70 | 1.37 | 2.24 | 1.21 | 2.08 | 2.70 | 1.77 | 2.66 | 2.66 | 1.55 | 1.56 | 2.61 |
| Q17 | 0.35 | 2.74 | 4.24 | 3.37 | 2.17 | 3.35 | 2.15 | 4.24 | 3.12 | 2.68 | 2.67 | 3.45 | 3.41 | 4.19 |
| Q18 | 2.72 | 0.57 | 2.87 | 2.04 | 1.89 | 1.96 | 1.75 | 2.86 | 1.87 | 2.21 | 2.21 | 1.82 | 1.82 | 2.72 |
| Q19 | 4.19 | 3.09 | 1.23 | 3.15 | 3.32 | 3.21 | 3.31 | 0.99 | 2.69 | 2.42 | 2.41 | 1.82 | 1.84 | 0.97 |
| Q20 | 3.34 | 1.07 | 4.06 | 0.70 | 2.12 | 0.73 | 2.08 | 3.06 | 2.11 | 2.87 | 2.87 | 1.73 | 1.79 | 2.93 |
| Q21 | 2.12 | 1.84 | 3.30 | 2.12 | 0.61 | 2.23 | 0.79 | 3.30 | 2.68 | 1.65 | 1.65 | 2.22 | 2.18 | 3.24 |
| Q22 | 3.31 | 1.93 | 4.11 | 0.81 | 2.23 | 0.57 | 2.11 | 3.11 | 1.89 | 2.96 | 2.97 | 1.86 | 1.89 | 2.97 |
| Q23 | 2.12 | 1.74 | 3.26 | 2.10 | 0.78 | 2.11 | 0.63 | 3.26 | 2.66 | 1.77 | 1.77 | 2.21 | 2.17 | 3.18 |
| Q24 | 4.18 | 2.82 | 1.86 | 3.08 | 3.34 | 3.09 | 3.26 | 0.89 | 2.44 | 2.55 | 2.55 | 1.71 | 1.76 | 0.66 |
| Q25 | 3.12 | 1.92 | 2.54 | 2.13 | 2.69 | 1.93 | 2.60 | 3.53 | 0.31 | 2.61 | 2.62 | 2.05 | 2.10 | 2.38 |
| Q26 | 2.63 | 2.19 | 2.54 | 2.89 | 1.65 | 2.99 | 1.79 | 2.54 | 2.66 | 0.65 | 0.63 | 2.05 | 2.00 | 2.57 |
| Q27 | 2.63 | 2.19 | 2.55 | 2.91 | 1.69 | 3.00 | 1.79 | 2.55 | 2.69 | 0.66 | 0.65 | 2.08 | 2.00 | 2.58 |
| Q28 | 3.41 | 1.80 | 1.74 | 1.76 | 2.21 | 1.86 | 2.18 | 1.73 | 2.06 | 2.02 | 2.02 | 0.64 | 0.75 | 1.59 |

TABLE 22-continued

| | | | | | | | | | | | | | |
|---|---|---|---|---|---|---|---|---|---|---|---|---|---|
| Q29 | 3.36 | 1.79 | 1.77 | 1.80 | 2.18 | 1.87 | 2.15 | 1.76 | 2.10 | 1.97 | 1.97 | 0.73 | 0.65 | 1.65 |
| Q30 | 4.16 | 2.72 | 0.87 | 2.96 | 3.26 | 2.98 | 3.18 | 0.87 | 2.34 | 2.53 | 2.53 | 1.63 | 1.71 | 0.61 |

TABLE 23

| Cluster | $|C_i|$ | H | B | E | G | I | T | S | U |
|---|---|---|---|---|---|---|---|---|---|
| C1 | 3 | 0.67 | 0.08 | 0.00 | 0.00 | 0.00 | 0.08 | 0.00 | 0.17 |
| C2 | 20 | 0.00 | 0.00 | 0.00 | 0.00 | 0.00 | 0.00 | 0.00 | 1.00 |
| C3 | 20 | 0.00 | 0.00 | 0.00 | 0.00 | 0.00 | 0.00 | 0.00 | 1.00 |
| C4 | 19 | 0.00 | 0.00 | 0.00 | 0.00 | 0.00 | 0.00 | 0.00 | 1.00 |
| C5 | 38 | 0.93 | 0.00 | 0.00 | 0.01 | 0.00 | 0.03 | 0.01 | 0.02 |
| C6 | 55 | 0.01 | 0.01 | 0.83 | 0.00 | 0.00 | 0.00 | 0.03 | 0.12 |
| C7 | 23 | 0.01 | 0.00 | 0.01 | 0.00 | 0.00 | 0.00 | 0.00 | 0.98 |
| C8 | 3 | 0.25 | 0.00 | 0.00 | 0.17 | 0.00 | 0.25 | 0.00 | 0.33 |
| C9 | 1 | 0.00 | 0.00 | 0.00 | 0.00 | 0.00 | 0.25 | 0.00 | 0.75 |
| C10 | 19 | 0.00 | 0.00 | 0.00 | 0.00 | 0.00 | 0.00 | 0.00 | 1.00 |
| C11 | 2 | 0.00 | 0.12 | 0.00 | 0.00 | 0.00 | 0.00 | 0.00 | 0.88 |
| C12 | 20 | 0.00 | 0.00 | 0.00 | 0.00 | 0.00 | 0.00 | 0.00 | 1.00 |
| C13 | 110 | 0.00 | 0.03 | 0.50 | 0.00 | 0.00 | 0.08 | 0.07 | 0.30 |
| C14 | 474 | 0.01 | 0.02 | 0.63 | 0.01 | 0.00 | 0.02 | 0.04 | 0.26 |
| C15 | 31 | 0.01 | 0.05 | 0.04 | 0.02 | 0.00 | 0.02 | 0.02 | 0.85 |
| C16 | 26 | 0.01 | 0.01 | 0.01 | 0.00 | 0.00 | 0.00 | 0.01 | 0.96 |
| C17 | 50 | 0.95 | 0.00 | 0.00 | 0.00 | 0.00 | 0.03 | 0.01 | 0.02 |
| C18 | 99 | 0.01 | 0.00 | 0.81 | 0.00 | 0.00 | 0.09 | 0.03 | 0.16 |
| C19 | 1687 | 0.03 | 0.03 | 0.39 | 0.02 | 0.00 | 0.06 | 0.11 | 0.35 |
| C20 | 136 | 0.01 | 0.01 | 0.74 | 0.00 | 0.00 | 0.01 | 0.04 | 0.19 |
| C21 | 111 | 0.00 | 0.00 | 0.80 | 0.00 | 0.00 | 0.00 | 0.02 | 0.16 |
| C22 | 102 | 0.01 | 0.01 | 0.73 | 0.00 | 0.00 | 0.01 | 0.03 | 0.20 |
| C23 | 107 | 0.00 | 0.00 | 0.82 | 0.00 | 0.00 | 0.01 | 0.03 | 0.12 |
| C24 | 1649 | 0.07 | 0.03 | 0.35 | 0.02 | 0.00 | 0.07 | 0.10 | 0.35 |
| C25 | 79 | 0.94 | 0.00 | 0.00 | 0.00 | 0.00 | 0.04 | 0.00 | 0.01 |
| C26 | 236 | 0.02 | 0.01 | 0.73 | 0.01 | 0.00 | 0.01 | 0.02 | 0.19 |
| C27 | 228 | 0.02 | 0.01 | 0.73 | 0.01 | 0.00 | 0.01 | 0.03 | 0.19 |
| C28 | 342 | 0.00 | 0.02 | 0.09 | 0.01 | 0.00 | 0.02 | 0.03 | 0.24 |
| C29 | 209 | 0.00 | 0.01 | 0.71 | 0.00 | 0.00 | 0.01 | 0.03 | 0.23 |
| C30 | 682 | 0.01 | 0.03 | 0.56 | 0.01 | 0.00 | 0.03 | 0.05 | 0.32 |

TABLE 24

| Motif size | 4 | 5 | 6 | 7 |
|---|---|---|---|---|
| C1 | 0.33 | 1.00 | 1.00 | 0.14 |
| C2 | 1.00 | 1.00 | 1.00 | 0.14 |
| C3 | 1.00 | 1.00 | 1.00 | 0.14 |
| C4 | 1.00 | 1.00 | 1.00 | 1.00 |
| C5 | 0.16 | 1.00 | 1.00 | 1.00 |
| C6 | 1.00 | 1.00 | 1.00 | 1.00 |
| C7 | 1.00 | 1.00 | 1.00 | 1.00 |
| C8 | 1.00 | 1.00 | 1.00 | 1.00 |
| C9 | 1.00 | 1.00 | 1.00 | 1.00 |
| C10 | 1.00 | 1.00 | 1.00 | 1.00 |
| C11 | 1.00 | 1.00 | 1.00 | 1.00 |
| C12 | 1.00 | 1.00 | 1.00 | 1.00 |
| C13 | 0.99 | 1.00 | 1.00 | 1.00 |
| C14 | 0.99 | 1.00 | 1.00 | 1.00 |
| C15 | 1.00 | 1.00 | 1.00 | 1.00 |
| C16 | 1.00 | 1.00 | 1.00 | 1.00 |
| C17 | 0.12 | 0.17 | 1.00 | 1.00 |
| C18 | 1.00 | 1.00 | 1.00 | 1.00 |
| C19 | 0.96 | 0.08 | 1.00 | 1.00 |
| C20 | 1.00 | 1.00 | 1.00 | 1.00 |
| C21 | 1.00 | 1.00 | 0.15 | 1.00 |
| C22 | 0.99 | 1.00 | 1.00 | 1.00 |
| C23 | 1.00 | 0.08 | 1.00 | 1.00 |
| C24 | 0.92 | 0.99 | 1.00 | 1.00 |
| C25 | 0.11 | 1.00 | 1.00 | 1.00 |
| C26 | 0.99 | 0.13 | 1.00 | 1.00 |
| C27 | 0.99 | 1.00 | 1.00 | 1.00 |
| C28 | 1.00 | 1.00 | 0.13 | 1.00 |
| C29 | 0.99 | 0.18 | 0.11 | 1.00 |
| C30 | 0.99 | 0.99 | 1.00 | 1.00 |

TABLE 25

| Cluster | $|C_i|$ | H | B | E | G | I | T | S | U |
|---|---|---|---|---|---|---|---|---|---|
| C1 | 28 | 0.97 | 0.00 | 0.00 | 0.00 | 0.00 | 0.02 | 0.01 | 0.01 |
| C2 | 29 | 0.96 | 0.00 | 0.00 | 0.00 | 0.00 | 0.02 | 0.00 | 0.01 |
| C3 | 35 | 0.97 | 0.00 | 0.00 | 0.00 | 0.00 | 0.01 | 0.01 | 0.01 |
| C4 | 14 | 0.00 | 0.00 | 0.00 | 0.00 | 0.00 | 0.00 | 0.00 | 1.00 |
| C5 | 14 | 0.00 | 0.00 | 0.00 | 0.00 | 0.00 | 0.00 | 0.00 | 1.00 |
| C6 | 14 | 0.00 | 0.00 | 0.00 | 0.00 | 0.00 | 0.00 | 0.00 | 1.00 |
| C7 | 14 | 0.00 | 0.00 | 0.00 | 0.00 | 0.00 | 0.00 | 0.00 | 1.00 |
| C8 | 14 | 0.00 | 0.00 | 0.00 | 0.00 | 0.00 | 0.00 | 0.00 | 1.00 |
| C9 | 15 | 0.00 | 0.00 | 0.00 | 0.00 | 0.00 | 0.00 | 0.00 | 1.00 |
| C10 | 15 | 0.00 | 0.00 | 0.00 | 0.00 | 0.00 | 0.00 | 0.00 | 1.00 |
| C11 | 15 | 0.00 | 0.00 | 0.00 | 0.00 | 0.00 | 0.00 | 0.00 | 1.00 |
| C12 | 15 | 0.00 | 0.00 | 0.00 | 0.00 | 0.00 | 0.00 | 0.00 | 1.00 |
| C13 | 15 | 0.00 | 0.00 | 0.00 | 0.00 | 0.00 | 0.00 | 0.00 | 1.00 |
| C14 | 15 | 0.00 | 0.00 | 0.00 | 0.00 | 0.00 | 0.00 | 0.00 | 1.00 |
| C15 | 15 | 0.00 | 0.00 | 0.00 | 0.00 | 0.00 | 0.00 | 0.00 | 1.00 |
| C16 | 15 | 0.00 | 0.00 | 0.00 | 0.00 | 0.00 | 0.00 | 0.00 | 1.00 |
| C17 | 15 | 0.00 | 0.00 | 0.00 | 0.00 | 0.00 | 0.00 | 0.00 | 1.00 |
| C18 | 15 | 0.00 | 0.00 | 0.00 | 0.00 | 0.00 | 0.00 | 0.00 | 1.00 |
| C19 | 17 | 0.00 | 0.00 | 0.00 | 0.00 | 0.00 | 0.00 | 0.00 | 1.00 |
| C20 | 18 | 0.00 | 0.00 | 0.00 | 0.00 | 0.00 | 0.00 | 0.00 | 1.00 |
| C21 | 18 | 0.00 | 0.00 | 0.00 | 0.00 | 0.00 | 0.00 | 0.00 | 1.00 |
| C22 | 18 | 0.00 | 0.00 | 0.00 | 0.00 | 0.00 | 0.00 | 0.00 | 1.00 |
| C23 | 18 | 0.00 | 0.00 | 0.00 | 0.00 | 0.00 | 0.00 | 0.00 | 1.00 |
| C24 | 18 | 0.00 | 0.00 | 0.00 | 0.00 | 0.00 | 0.00 | 0.00 | 1.00 |
| C25 | 18 | 0.00 | 0.00 | 0.00 | 0.00 | 0.00 | 0.00 | 0.00 | 1.00 |
| C26 | 19 | 0.00 | 0.00 | 0.00 | 0.00 | 0.00 | 0.00 | 0.00 | 1.00 |
| C27 | 19 | 0.00 | 0.00 | 0.00 | 0.00 | 0.00 | 0.00 | 0.00 | 1.00 |
| C28 | 19 | 0.00 | 0.00 | 0.00 | 0.00 | 0.00 | 0.00 | 0.00 | 1.00 |
| C29 | 19 | 0.00 | 0.00 | 0.00 | 0.00 | 0.00 | 0.00 | 0.00 | 1.00 |
| C30 | 19 | 0.00 | 0.00 | 0.00 | 0.00 | 0.00 | 0.00 | 0.00 | 1.00 |

TABLE 26

| | | $C_\alpha$ | | | $C_\beta$ | | |
|---|---|---|---|---|---|---|---|
| Type of motif | | x | y | z | x | y | z |
| B-turns | 4-residues | 1.9 | 45.1 | 23.2 | 2.0 | 45.8 | 22.0 |
| | | 4.4 | 43.0 | 25.2 | 4.3 | 42.9 | 26.7 |
| | | 3.5 | 39.7 | 23.5 | 2.3 | 39.0 | 23.9 |
| | | 3.8 | 41.0 | 19.9 | 3.4 | 42.3 | 19.4 |
| Loops | 4-residues | 35.6 | 40.1 | 67.8 | 35.3 | 40.3 | 69.0 |
| | | 33.3 | 40.2 | 64.9 | 32.5 | 41.5 | 64.6 |
| | | 34.6 | 38.2 | 61.9 | 35.1 | 36.9 | 62.2 |
| | | 31.6 | 38.5 | 59.7 | 30.4 | 38.3 | 59.9 |
| Mostly single α-helix surface | 4-residues | 49.4 | 26.0 | 67.5 | 50.3 | 25.6 | 68.7 |
| | | 46.5 | 23.9 | 66.1 | 45.5 | 23.8 | 67.2 |
| | | 50.4 | 21.1 | 68.6 | 51.5 | 20.0 | 68.7 |
| | | 47.0 | 20.9 | 70.2 | 47.2 | 20.9 | 71.7 |
| | 5-residues | 9.8 | 2.9 | 30.7 | 10.4 | 2.3 | 31.8 |
| | | 6.1 | 2.0 | 30.7 | 5.1 | 2.4 | 31.7 |
| | | 8.4 | 2.5 | 25.8 | 9.8 | 2.5 | 26.2 |
| | | 7.1 | −1.0 | 26.7 | 6.9 | −1.5 | 28.1 |
| | | 7.1 | −1.9 | 21.6 | 8.2 | −2.4 | 22.5 |
| | 6-residues | 14.2 | 11.6 | 49.2 | 13.9 | 11.1 | 50.6 |
| | | 14.1 | 10.7 | 44.2 | 15.1 | 10.1 | 45.2 |
| | | 10.9 | 8.9 | 44.7 | 10.0 | 8.9 | 46.0 |
| | | 11.6 | 6.8 | 40.2 | 11.9 | 6.0 | 41.5 |
| | | 7.9 | 6.8 | 39.8 | 6.9 | 7.5 | 40.7 |
| | | 9.5 | 4.5 | 35.6 | 9.8 | 4.0 | 36.6 |
| | 7-residues | 23.8 | 10.2 | 60.4 | 22.4 | 10.7 | 60.1 |
| | | 23.3 | 6.7 | 61.9 | 22.8 | 5.5 | 61.1 |
| | | 24.6 | 8.8 | 66.3 | 23.1 | 8.6 | 66.0 |
| | | 26.1 | 5.4 | 67.2 | 26.3 | 4.3 | 66.2 |
| | | 26.0 | 6.8 | 72.0 | 25.0 | 5.9 | 71.4 |
| | | 28.4 | 8.5 | 76.3 | 27.0 | 9.0 | 75.9 |
| | | 28.2 | 4.9 | 77.4 | 27.8 | 3.8 | 76.6 |

TABLE 26-continued

| Type of motif | | Cα | | | Cβ | | |
|---|---|---|---|---|---|---|---|
| | | x | y | z | x | y | z |
| Mostly non-singleα-helix surface | 4-residues | 80.5 | 4.4 | 21.7 | 81.1 | 4.4 | 20.7 |
| | | 78.2 | 7.2 | 22.7 | 78.1 | 7.3 | 24.1 |
| | | 73.6 | 11.8 | 21.6 | 74.0 | 12.2 | 23.0 |
| | | 70.4 | 13.1 | 20.3 | 70.0 | 12.6 | 19.3 |
| | 5-residues | 14.8 | −1.5 | 24.2 | 13.5 | −0.7 | 24.1 |
| | | 15.5 | −2.5 | 20.6 | 15.9 | −1.6 | 19.4 |
| | | 18.8 | −4.1 | 21.7 | 20.0 | −3.4 | 22.3 |
| | | 15.1 | −13.2 | 19.9 | 14.9 | −12.3 | 18.8 |
| | | 15.8 | −18.6 | 20.1 | 15.4 | −17.9 | 19.4 |
| | 6-residues | 5.1 | −10.3 | 1.7 | 6.2 | −10.1 | 0.9 |
| | | 3.2 | −7.1 | 2.3 | 3.6 | −6.3 | 3.5 |
| | | 2.2 | −4.8 | −0.6 | 3.0 | −3.7 | −0.5 |
| | | 4.0 | −1.6 | −1.6 | 4.2 | −1.5 | −3.0 |
| | | 3.2 | 1.8 | −0.1 | 4.3 | 2.6 | 0.4 |
| | | 0.5 | 3.9 | −1.7 | 1.1 | 5.1 | −2.3 |
| | 7-residues | −2.9 | 30.2 | −0.9 | −3.8 | 31.4 | −1.2 |
| | | −4.9 | 33.4 | −0.3 | −5.3 | 33.7 | 1.1 |
| | | −4.1 | 36.7 | −2.1 | −5.3 | 37.5 | −2.7 |
| | | −2.5 | 42.3 | 1.4 | −1.8 | 42.6 | 2.7 |
| | | −3.0 | 45.6 | −0.4 | −4.2 | 46.5 | −0.1 |
| | | 0.1 | 48.1 | −0.9 | −0.1 | 49.2 | 0.0 |
| | | 0.7 | 50.9 | 1.0 | 2.1 | 51.1 | 1.4 |

The invention claimed is:

1. A method using a computer to produce a library of molecules matching a descriptor of a common three-dimensional protein surface shape, comprising:
   (i) identifying a three-dimensional surface shape of each of three or more non-homologous proteins;
   (ii) creating one or more descriptors wherein each said descriptor represents a common surface shape derived from said three-dimensional surface shapes of said three or more non-homologous proteins;
   (iii) creating a query using one or more of said one or more descriptors;
   (iv) using said query to search a database and thereby identify one or more entries in said database that correspond to one or more molecules that each match said one or more descriptors; and
   (iv) (v) using at least one of the one or more molecules identified at step (iv) to create a library of molecules.

2. The method of claim 1, wherein each three-dimensional surface shape identified at step (i) is represented by a side-chain location and orientation of two or more amino acids of each said three-dimensional surface shape.

3. The method of claim 2, wherein at step (ii) each said descriptor represents a common location and orientation of respective side chains of two or more amino acids of each of said three or more proteins.

4. The method of claim 3, wherein each said descriptor represents a common location and orientation of respective side chains of three or more amino acids of each of said three or more proteins.

5. The method of claim 2, wherein the location and orientation of each said amino acid side chain is in three-dimensional (3D) space.

6. The method of claim 5, wherein each amino acid side chain used to produce said descriptor is represented as a Cα-Cβ vector.

7. The method of claim 1, wherein each three-dimensional surface shape identified at step (i) is represented as a charged surface region of each of said plurality of proteins.

8. The method of claim 7, wherein at step (ii) each said descriptor represents a common charged surface region of said three or more non-homologous proteins.

9. The method of claim 8, wherein each charged surface region is represented by at least four grid points.

10. The method of claim 9, wherein respective said grid points are 0.2 to 2.0 angstrom apart in three dimensional (3D) space.

11. The method of claim 10, wherein respective said grid points are 0.5-1.5 angstrom apart in three dimensional (3D) space.

12. The method of claim 1, wherein said three-dimensional surface shape is of at least part of a structural feature of each of said two or more proteins.

13. The method of claim 12, wherein said structural feature is, or comprises, a β-turn, a loop or a contact surface.

14. The method of claim 12, wherein said structural feature is, or comprises, a loop or a contact surface.

15. The method of claim 13, wherein the contact surface comprises one or more discontinuous and/or continuous surfaces.

16. The method of claim 3, wherein each said descriptor represents side-chain location and orientation of four β-turn or loop amino acids.

17. The method of claim 3, wherein each said descriptor represents side-chain location and orientation of at least three amino acids of a contact surface.

18. The method of claim 17, wherein said descriptor represents side-chain location and orientation of four, live, six or seven amino acid side-chains of a contact surface.

19. The method of claim 6, wherein the Cα-Cβ vectors are represented as a distance matrix.

20. The method of claim 1, wherein said library of molecules is a virtual library.

21. The method of claim 1, wherein said library of molecules is a synthetic chemical library.

22. The method of claim 1, wherein the library of molecules comprises molecules engineered to comprise one or more structural features according to each descriptor produced at step (ii).

23. A method using a computer to produce a molecule matching a descriptor of a common three-dimensional protein surface shape, comprising:
   (i) providing a computer searchable database that returns one or more molecules when provided a descriptor of a three dimensional protein surface shape;
   (ii) creating a common three-dimensional protein surface shape from three-dimensional surface shapes of each of three or more non-homologous proteins;
   (iii) deriving one or more descriptors of said common surface shape;
   (iv) searching the computer-searchable database using a query generated from the one or more descriptors to thereby identify one or more molecules that each match said descriptor; and
   (vi) producing a molecule identified at step (iv).

* * * * *